United States Patent
Schoenberg et al.

(10) Patent No.: US 8,714,472 B2
(45) Date of Patent: May 6, 2014

(54) WINDER REGISTRATION AND INSPECTION SYSTEM

(75) Inventors: Brett Schoenberg, Evans, GA (US); Mark Gary Dollevoet, Freedom, WI (US); Jeffrey George Skarda, Appleton, WI (US); Matthew Robert Wilson, Oshkosh, WI (US); Kevin B. Sartain, Evans, GA (US); Gregory Michael Bixler, Appleton, WI (US); Daniel Mark Heinz, Greenville, WI (US); Vivek Moreshwar Karandikar, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1072 days.

(21) Appl. No.: 12/750,331

(22) Filed: Mar. 30, 2010

(65) Prior Publication Data
US 2011/0240789 A1  Oct. 6, 2011

(51) Int. Cl.
*B65H 26/02* (2006.01)
(52) U.S. Cl.
USPC .................. 242/534.1; 242/413.1; 242/420.5
(58) Field of Classification Search
USPC ............... 242/534, 534.1, 534.2, 563, 563.1, 242/563.2, 412.1, 412.2, 412.3, 413, 413.1, 242/420, 420.5
See application file for complete search history.

(56) References Cited

U.S. PATENT DOCUMENTS

| | | | |
|---|---|---|---|
| 125,597 A | 4/1872 | Mayall | |
| 1,648,990 A | 11/1927 | Little | |
| 1,894,253 A | 1/1933 | McCarthy et al. | |
| 2,326,173 A | 8/1943 | Russell | |
| 2,328,582 A | 9/1943 | Ratchford et al. | |
| 2,979,278 A | 4/1961 | Jones | |
| 3,123,315 A | 3/1964 | Couzens | |
| 3,148,843 A | 9/1964 | Turner et al. | |
| 3,157,371 A | 11/1964 | Billingsley | |
| 3,315,908 A | 4/1967 | Wetzler | |
| 3,430,881 A | 3/1969 | Ebneter | |

(Continued)

FOREIGN PATENT DOCUMENTS

| | | |
|---|---|---|
| CH | 476620 | 9/1969 |
| DE | 3920659 A1 | 1/1999 |

(Continued)

OTHER PUBLICATIONS

PCT/IB2011/050704 Written Opinion and Search Report dated Dec. 9, 2011.

(Continued)

*Primary Examiner* — William A Rivera
(74) *Attorney, Agent, or Firm* — Dority & Manning, P.A.

(57) ABSTRACT

Registration and inspection systems and methods for use on a winder are disclosed. The systems and methods include scanning a region proximate a winding module with one or more sensors to determine a product defect. The product defect is then associated with a winding process parameter, such as percent roll build information or the identity of the particular sensor to first detect the defect. The winding process parameter is used to classify the defect into one or more defect profiles. The defect profiles can be based at least in part on segmenting the roll build of a web onto a winding module into a plurality of inspection windows and segmenting a plurality of sensors into a plurality of inspection sensor segments.

25 Claims, 37 Drawing Sheets

(56) References Cited

U.S. PATENT DOCUMENTS

| | | | |
|---|---|---|---|
| 3,519,214 A | 7/1970 | Konrad et al. | |
| 3,733,035 A | 5/1973 | Schott, Jr. | |
| RE28,353 E | 3/1975 | Nytsrand et al. | |
| 3,869,095 A | 3/1975 | Diltz | |
| 4,034,928 A | 7/1977 | McDonald et al. | |
| 4,087,319 A | 5/1978 | Linkletter | |
| 4,133,495 A | 1/1979 | Dowd | |
| 4,139,164 A | 2/1979 | Alfio | |
| 4,143,828 A | 3/1979 | Braun et al. | |
| 4,191,341 A | 3/1980 | Looser | |
| 4,283,023 A | 8/1981 | Braun et al. | |
| 4,327,876 A | 5/1982 | Kuhn | |
| 4,486,843 A | 12/1984 | Spongh et al. | |
| 4,529,141 A | 7/1985 | McClenathan | |
| 4,541,583 A | 9/1985 | Forman et al. | |
| 4,583,698 A | 4/1986 | Nistri et al. | |
| 4,588,138 A | 5/1986 | Spencer | |
| 4,723,724 A | 2/1988 | Bradley | |
| 4,782,354 A * | 11/1988 | Gregoris | 396/622 |
| 4,856,725 A | 8/1989 | Bradley | |
| 4,930,711 A | 6/1990 | Morizzo | |
| 4,962,897 A | 10/1990 | Bradley | |
| 4,988,052 A | 1/1991 | Urban | |
| 5,054,708 A | 10/1991 | Wiggers | |
| 5,169,084 A | 12/1992 | Pötter et al. | |
| 5,226,612 A | 7/1993 | Mülfarth | |
| 5,346,150 A | 9/1994 | Volin | |
| 5,379,964 A | 1/1995 | Pretto et al. | |
| 5,402,960 A | 4/1995 | Oliver et al. | |
| 5,421,536 A | 6/1995 | Hertel et al. | |
| 5,433,253 A * | 7/1995 | Toda et al. | 139/1 B |
| 5,437,417 A | 8/1995 | Kammann | |
| 5,497,959 A | 3/1996 | Johnson et al. | |
| 5,505,402 A | 4/1996 | Vigneau | |
| 5,518,200 A | 5/1996 | Kaji et al. | |
| 5,531,396 A | 7/1996 | Kinnunen et al. | |
| 5,593,545 A | 1/1997 | Rugowski et al. | |
| 5,694,979 A * | 12/1997 | Toda | 139/1 B |
| 5,746,379 A | 5/1998 | Shimizu | |
| 5,832,696 A | 11/1998 | Nagy et al. | |
| 5,839,688 A | 11/1998 | Hertel et al. | |
| 5,901,918 A | 5/1999 | Klerelid et al. | |
| 5,918,830 A | 7/1999 | Verajankorva et al. | |
| 5,944,273 A | 8/1999 | Lin et al. | |
| 5,979,818 A | 11/1999 | Perini | |
| 6,050,469 A | 4/2000 | Brabant et al. | |
| 6,056,229 A | 5/2000 | Blume et al. | |
| 6,062,507 A | 5/2000 | Summey, III | |
| 6,142,407 A | 11/2000 | McNeil et al. | |
| 6,264,132 B1 | 7/2001 | Menz et al. | |
| 6,283,402 B1 | 9/2001 | Fordham | |
| 6,308,909 B1 | 10/2001 | McNeil et al. | |
| 6,311,921 B1 | 11/2001 | Moller et al. | |
| 6,332,589 B1 | 12/2001 | Leitenberger et al. | |
| 6,404,910 B1 | 6/2002 | Ungpiyakul et al. | |
| 6,523,775 B2 | 2/2003 | Fan | |
| 6,595,458 B1 | 7/2003 | Biagiotti | |
| 6,729,572 B2 | 5/2004 | Baggot et al. | |
| 6,845,278 B2 | 1/2005 | Popp et al. | |
| 6,966,521 B2 | 11/2005 | White | |
| 7,000,864 B2 | 2/2006 | McNeil et al. | |
| 7,082,347 B2 | 7/2006 | Popp et al. | |
| 7,171,283 B2 | 1/2007 | Popp et al. | |
| 7,175,127 B2 | 2/2007 | Butterworth et al. | |
| 2003/0037725 A1 | 2/2003 | Daul et al. | |
| 2003/0100961 A1 | 5/2003 | Monse et al. | |
| 2003/0160127 A1 | 8/2003 | Wojcik et al. | |
| 2004/0061021 A1 | 4/2004 | Butterworth | |
| 2005/0273652 A1 | 12/2005 | Okawa et al. | |
| 2005/0278707 A1 | 12/2005 | Guilford | |
| 2007/0241160 A1 | 10/2007 | Kenney | |
| 2008/0061182 A1 | 3/2008 | Wojcik et al. | |
| 2008/0098260 A1 | 4/2008 | Okawa et al. | |
| 2008/0105776 A1 | 5/2008 | Wojcik et al. | |
| 2008/0169373 A1 * | 7/2008 | Andrews et al. | 242/554.2 |

FOREIGN PATENT DOCUMENTS

| | | |
|---|---|---|
| EP | 0118384 A1 | 9/1984 |
| EP | 0198495 A2 | 10/1986 |
| EP | 0313859 A2 | 5/1989 |
| EP | 0408526 B1 | 1/1991 |
| EP | 0658504 A2 | 6/1995 |
| EP | 1006066 A2 | 11/1999 |
| EP | 1076130 A2 | 2/2001 |
| EP | 1262434 | 12/2002 |
| EP | 1273540 | 1/2003 |
| FR | 2669013 | 5/1992 |
| GB | 886774 | 1/1962 |
| JP | 6032501 A | 2/1994 |
| JP | 6166951 A | 6/1994 |
| JP | 7037362 A | 2/1995 |
| JP | 8103976 A | 4/1996 |
| JP | 2003-44144 | 2/2003 |
| WO | WO 9852857 A1 | 11/1998 |
| WO | WO 9855384 | 12/1998 |
| WO | WO 0047503 | 8/2000 |
| WO | WO 0066470 | 11/2000 |
| WO | WO 02055420 A1 | 7/2002 |

OTHER PUBLICATIONS

Intelligent Motion Unites Diverse Worlds, Frank J. Bartos, Dec. 1, 2004, http://www.controleng.com.

Rockwell's ControlLogix TM Controller Pending Cam Function: A-B Journal, Kinetix: the new science of motion control, Jan./Feb. 2002, vol. 9, No. 1, p. 40, http://www.ab.com/abjournal/Feb2002/pdfs/ABJ0202.pdf.

Related US Applications Form.

* cited by examiner

| CULL NO. | PHOTOEYE NAME | CURRENT SHIFT COUNT (INDIV.) | PREVIOUS SHIFT COUNT (INDIV.) | TEMP. COUNT (INDIV.) | ENABLE / DISABLE | STATUS | TEACH FUNCTION | |
|---|---|---|---|---|---|---|---|---|
| 0 | WINDING DEFECT – POSITION 1 | 0 | 0 | 0 | ENABLED | O | TEACH | DISABLED |
| 1 | WINDING DEFECT – POSITION 2 | 0 | 0 | 0 | ENABLED | O | | |
| 2 | WINDING DEFECT – POSITION 3 | 0 | 0 | 0 | ENABLED | O | TEACH | DISABLED |
| 3 | WINDING DEFECT – POSITION 4 | 0 | 0 | 0 | ENABLED | O | | |
| 4 | WINDING DEFECT – POSITION 5 | 0 | 0 | 0 | ENABLED | O | TEACH | DISABLED |
| 5 | WINDING DEFECT – POSITION 6 | 0 | 0 | 0 | ENABLED | O | | |
| 6 | WINDING DEFECT – POSITION 7 | 0 | 0 | 0 | ENABLED | O | TEACH | DISABLED |
| 7 | WINDING DEFECT – POSITION 8 | 0 | 1 | 0 | ENABLED | O | | |
| 8 | WINDING DEFECT – POSITION 9 | 0 | 0 | 0 | ENABLED | O | TEACH | DISABLED |
| 9 | MODULE 1 – MANDREL NIP BUILD UP | | | | ENABLED | O | | |
| 10 | MODULE 1 – CD WINDING DEFECT | | | | ENABLED | O | | |

RESET  } 3510  3520

NOTE: TEACH EYES WITH LIFT AT XXX mm

| INSPECTION | | LAST 10 RIS CULLS | | | |
|---|---|---|---|---|---|
| UPSTREAM OF MODULES | CURRENT CULL | RIS CULL NAME | HOUR | MIN | SEC |
| MODULE 1 | -1 | MODULE DRIVE SIDE DOWN STREAM CULL EVENT | 23 | 45 | 17 |
| MODULE 2 | -2 | MODULE DRIVE SIDE TRANSFER DEFECT | 21 | 54 | 29 |
| MODULE 3 | -3 | MODULE DRIVE SIDE TRANSFER DEFECT | 13 | 20 | 45 |
| MODULE 4 | -4 | MODULE CROSS DIRECTION TRANSFER DEFECT | 15 | 26 | 3 |
| MODULE 5 | -5 | MODULE CROSS DIRECTION TRANSFER DEFECT | 13 | 12 | 10 |
| MODULE 6 | -6 | MODULE CROSS DIRECTION TRANSFER DEFECT | 12 | 44 | 22 |
| DOWNSTREAM OF MODULES | -7 | MODULE CROSS DIRECTION TRANSFER DEFECT | 11 | 10 | 8 |
| SUMMARY | -8 | MODULE CROSS DIRECTION TRANSFER DEFECT | 8 | 25 | 11 |
| REGISTRATION | -9 | MODULE CROSS DIRECTION TRANSFER DEFECT | 7 | 30 | 19 |
| ... | | MODULE CROSS DIRECTION TRANSFER DEFECT | 7 | 12 | 4 |
| ... | | CLOSE | | | |

3710

WINDER REGISTRATION AND INSPECTION SYSTEM

BACKGROUND

Winders and rewinders are machines that roll lengths of paper, commonly known as paper webs into rolls. These machines are capable of rolling lengths of web into rolls at high speeds through an automated process. A winder is typically known as an apparatus that performs the very first wind of the web, forming what is generally known as a parent roll. A rewinder, on the other hand, is typically known as an apparatus that winds the web from the parent roll onto a log that is essentially a finished product. For instance, the paper web is unwound from a parent roll in a continuous fashion, and the rewinder winds the paper web onto cores supported on mandrels to provide individual, relatively small diameter logs. The rolled product log is then cut to designated lengths into the final product. Final products typically created by these machines and processes are toilet tissue rolls, paper towel rolls, paper rolls, and the like.

Various different types of winders exist. For instance, turret winders comprise a rotating turret assembly which support a plurality of mandrels for rotation about a turret axis. The mandrels travel in a circular path at a fixed distance from the turret axis. Hollow cores are loaded onto the winding mandrels upon which paper can be wound. The winding technique used in turret winders/rewinders is known as center winding. A center winding apparatus, for instance, is disclosed in U.S. Pat. Reissue No. 28,353 to Nystrand, which is incorporated herein by reference. In center winding, a mandrel is rotated in order to wind a web into a log, either with or without a core. Typically, the core is loaded and supported on a mandrel that rotates at high speeds at the beginning of a winding cycle and then slows down as the size of the rolled product being wound increases, in order to maintain a constant surface speed, approximately matching web speed. Also, typically, center winders can be preferable for efficiently producing soft-wound, higher bulk rolled products.

A second type of winding is known in the art as surface winding. A machine that uses the technique of surface winding is disclosed in U.S. Pat. No. 4,583,698 which is incorporated herein by reference. Typically, in surface winding, the web is wound onto the core via contact and friction developed with rotating rollers. A nip is typically formed between two or more co-acting roller systems. In surface winding, the core and the web that is wound around the core are usually driven by rotating rollers that operate at approximately the same speed as the web speed. Surface winding is preferable for efficiently producing hard-wound, lower bulk rolled products.

Another type of winder, known as a flex winder, can perform both center winding and surface winding or a combination of center winding and surface winding. Such an exemplary winding apparatus is disclosed in U.S. Patent Application Publication No. 2008/0105776, which is incorporated herein by reference. The winder includes a web transport apparatus that is used for conveying the web. Also included can be a plurality of independent winding modules. The winding modules can be independently positioned to independently engage the web as the web is conveyed by the web transport apparatus. The winding modules may be configured to wind the web to form a rolled product by center winding, surface winding, and combinations of center and surface winding. The winding modules are structurally and operationally independent of one another where if one module is disabled, another may still operate to produce the rolled product without shutting down the winder.

Registration and inspection systems can be used in connection with winders for a variety of purposes, including quality control purposes, process control purposes, material control purposes, and other suitable purposes. For instance, it can desirable to monitor and detect breaks in the webs, defects in the winding process (such as roll build defects, web transfer defects to the mandrel at the start of log wind, etc.), and to detect other parameters. It can also be desirable to gather data concerning web transfer and roll build during the winding process and determine the presence of defects warranting cull events. As used herein, a cull event is intended to refer to an event in which a rolled product is culled from a group of saleable products due to a defect in the rolled product.

Various methods of break detection and web inspection systems exist for monitoring web transfer, roll build, and other parameters of a winding process. Such inspection systems may use one or more photo-eyes or other sensors for basic web break detection and to trigger faults on winders. For instance, winders can have a photo-eye or sensor on both ends of the web at several locations in the machine direction that indicate on which side of the web transport apparatus a break in the web occurs. A photo-eye that shoots across the cross direction of logs on a turret style winder can also be used to detect winding disruptions.

Existing break detection and inspection systems, however, lack robustness in terms of sensitivity, configurability and integration necessary for application to winders that provide for greater toleration and masking of winding defects. For instance, certain inspection systems require a web break or large winding defect to trigger a cull event. Applicability of such inspection systems to winders with increased defect toleration and masking, such as flex winders, can result in the culling of saleable products, leading to waste, or in the providing of products with rejectable defects to consumers. Moreover, existing inspection systems provide limited defect profiling and scan capabilities for associating winding defect types with defect locations during the winding process.

Thus, there is a need for a registration and inspection system that can be used in conjunction with winders that provide for increased toleration and masking of winding defects that overcomes the above-mentioned disadvantages.

SUMMARY

Aspects and advantages of the invention will be set forth in part in the following description, or may be obvious from the description, or may be learned from practice of one or more embodiments the present invention.

As used herein, "winder" is generic to a machine for forming a parent roll, and a machine (rewinder) for forming a roll/log from a parent roll. In other words, the word "winder" is broad enough to cover both a "winder" and "rewinder."

One exemplary embodiment of the present disclosure is directed to an inspection method suitable for use in connection with a winder producing a rolled product from a web. The winder can include a web transport apparatus for conveying a web and at least one winding module onto which the web is rolled to form the rolled product during a winding process. The winder can define a cross-direction that is generally perpendicular to the direction the web is conveyed by the web transport apparatus. The method includes scanning with at least one sensor in a region proximate to the winding module and detecting a defect with the at least one sensor. The method further includes associating a winding process parameter with the defect and classifying the defect into at least one of a plurality of defect profiles based on the winding process parameter associated with the defect.

For instance, in a particular variation of this exemplary embodiment, the winding process parameter associated with the defect can be the percent roll build of the web on the winding module when the defect is detected. The percent roll build can be measured as web distance with zero distance being the point at which the web is transferred to the winding module. Classifying the defect into at least one of a plurality of defect profiles can include segmenting a roll build of the web onto the winding module into a plurality of inspection windows, such as a roll transfer inspection window, a roll build inspection window, and a post roll build inspection window. The method can include classifying the defect into one of the plurality of inspection windows based at least in part on the percent roll build associated with the defect. In a particular embodiment, the roll transfer inspection window can be defined to exclude a period of the roll build following the initiation of the winding process. Similarly, in another embodiment, the post roll build inspection window can be defined to exclude a period of the roll build immediately preceding the termination of the winding process.

In another variation of this exemplary embodiment, the at least one sensor can include a cross-direction winding sensor positioned to scan across the cross-direction of the winding module at a location proximate the winding module, such as proximate upstream to the winding module or proximate downstream to the winding module. In another variation of this exemplary embodiment, the at least one sensor can include a plurality of leading edge sensors positioned upstream of the at least one winding module used to phase the leading edge of web on the transport conveyor to the downstream winding module for improved transfer registration to the winding mandrel.

In yet another variation of this exemplary embodiment, the at least one sensor can include a plurality of winding defect array sensors positioned to scan a region across a width of the web traveling on the web transport apparatus at a location downstream of the winding module. In this exemplary embodiment, the winding process parameter associated with the defect can include the identity of the particular winding defect array sensor to first detect the defect, in addition to other sensor(s) that detected the defect. Classifying the defect into at least one of the plurality of defect profiles can include segmenting the plurality of winding defect array sensors into a plurality of inspection sensor segments, such as, for instance, an operator side sensor segment, a middle sensor segment, and a drive side sensor segment. The method can include classifying the defect into one of the plurality of inspection sensor segments based on the identity of the winding defect array sensor associated with the defect.

In still another variation of this exemplary embodiment, the at least one sensor can include one of a photo-eye sensor, proximity switch, photo eye array, camera, or laser. The sensor can be configured with a controller to detect a defect based on sensing the presence of the web in one or more scans performed by the sensor. The method can include adjusting the sensitivity of the sensor in response to various process parameters. For instance, the sensor can have a scan filter count that defines the number of scans for the controller/sensor to detect the presence of the web before detecting a defect and possibly triggering a cull event. The scan filter count can be defined in number of scans or a precise web distance to trigger a cull event for each window segment based on the scan rate of the controller and winder speed. The sensitivity of the sensor can be adjusted by varying the scan filter count for the sensor.

In a particular embodiment, the method can further include adjusting the sensitivity for the sensor based at least in part on the roll build of the web onto the winding module. For instance, the roll build of the web can be segmented into a roll transfer inspection window segment, a roll build inspection window segment, and post roll build inspection segment. The scan filter count for the sensor during the roll build inspection window segment can be adjusted independently to be higher or lower than the scan filter count for the sensor during the roll transfer and post roll build inspection window segments.

In yet another variation of this exemplary embodiment, the method can further include controlling the at least one winding module based at least in part on the defect. For instance, the method can include using any of the asynchronous control methods or techniques disclosed herein to control the winding module or other aspects of the winder in response to detecting a defect during the winding process.

Another exemplary embodiment of the present disclosure is directed to a system for monitoring defects suitable for use in connection with a winder producing a rolled product from a web. The winder can include a web transport apparatus for conveying a web and at least one winding module onto which the web is rolled to form the rolled product during the winding process. The winding modules can define a cross-direction that is generally perpendicular to the direction the web is conveyed on the web transport apparatus. The system can include a plurality of sensors configured to scan a region proximate the winding module. Each of the plurality of sensors can be configured to detect a defect during the winding process. The system can further include a controller coupled to the plurality of sensors. The controller can be configured to associate a winding process parameter with the defect and to classify the defect into at least one of the plurality of defect profiles based at least in part on the winding process parameter associated with the defect.

For instance, in a particular variation of this exemplary embodiment, the winding process parameter can include at least one of the percent roll build of the web onto the winding module when the defect is detected or the identity of the sensor to first detect the defect. The plurality of defect profiles can be based at least in part on segmenting the roll build of the web into a roll transfer inspection window, a roll build inspection window, and a post roll build inspection window. Alternatively or in addition, the plurality of defect profiles can be based at least in part on segmenting the plurality of sensors into an operator side sensor segment, a middle sensor segment, and a drive side sensor segment.

In particular implementations of this exemplary embodiment, the plurality of sensors can include a cross-direction winding sensor positioned to scan across the cross-direction of the winding module at a location proximate to the winding module. In another implementation of this exemplary embodiment, the plurality of sensors can include a plurality of winding defect array sensors positioned to scan across a width of the web transport apparatus at a location downstream of the winding module. In another implementation of this exemplary embodiment, the plurality of sensors can include a plurality of leading edge sensors positioned upstream of the at least one winding module used to phase the leading edge of web on the transport conveyor to the downstream winding module for improved transfer registration to the winding mandrel. In yet a further implementation of this exemplary embodiment, the plurality of sensors can further include a plurality of downstream module array sensors positioned to scan across a width of the web transport apparatus at a location downstream of the plurality of winding defect array sensors. The plurality of sensors can be photo-eye sensors, proximity switches, photo eye arrays, cameras, lasers, or other suitable sensors. Each of the plurality of sensors can have scan filter counts and/or sensing windows that can be adjusted based at least in part on the roll build of the web onto the winding module.

In other variations of this exemplary embodiment, the system can be coupled to a user interface that allows a user or operator to manipulate and control the system and that provides information to a user or operator of the system. Manipulation may include optimization of sensor position relative to the moving web, teaching the sensor, configuring cull characteristics for the sensor, enabling/disabling the sensor, and troubleshooting operation of the sensor.

In still other variations of this exemplary embodiment, the controller can be programmed or configured to control various aspects of the winding process to reduce waste or delay or to improve winding performance. The controller can also be coupled to or part of a master control system for the winder to control the winding module or other aspects of the winder in response to detecting a defect to reduce waste or delay outcomes associated with specific types of cull events. In a particular embodiment, the controller can also control the winding process to abort winding a full roll once a defect is detected.

In still further variations of this exemplary embodiment, the controller can be coupled to leading edge sensors. For instance, the leading edge sensors can be used to verify the presence of a web, leading edge position relative to downstream module for increased transfer precision and detection of leading edge defects on the web transport apparatus.

A further exemplary embodiment of the present disclosure is directed to a system for monitoring defects suitable for use in connection with a winder producing a rolled product from a web. The winder can include a web transport apparatus and a plurality of independent winding modules onto which the web is rolled to form the rolled product during the winding process. The independent winding modules can define a cross-direction generally perpendicular to the direction the web is conveyed on the web transport apparatus.

The system can include a plurality of first sensors associated with at least one of the plurality of independent winding modules. The first sensors can be positioned to scan across a width of the transport apparatus at discrete points across the width at a location downstream of the winding module. Each of the plurality of first sensors can be configured to detect a defect during the winding process.

The system can further include a second sensor associated with at least one of the plurality of independent winding modules. The second sensor can be positioned to scan across the cross-direction of the transport apparatus at a location proximate downstream of the winding module. The second sensor can be configured to detect a defect during the winding process.

The system can further include a controller coupled to the plurality of the first sensors and the second sensor for each independent winding module. In variations of this exemplary embodiment, the controller can be configured to classify a defect detected by one of the first sensors or the second sensor into one of a plurality of defect profiles. For instance, in a particular embodiment, the controller can be configured to classify a defect into a plurality of defect profiles that are based at least in part on segmenting a roll build of the web onto one of the independent winding modules into a plurality of inspection windows and segmenting the plurality of first sensors into a plurality of inspection sensor segments.

In a variation of this exemplary embodiment, the system can further include a third sensor associated with at least one of the plurality of independent winding modules. The third sensor can be positioned to scan across the cross-direction of the transport apparatus at a location proximate upstream to the winding module. The third sensor can also be configured to detect a defect during the winding process.

In another variation of this exemplary embodiment, the system can further include a plurality of fourth sensors positioned to scan across a width of the web transport apparatus at a location downstream of all winding modules. The plurality of fourth sensors can be positioned to scan a width of the web transport apparatus at a location downstream of the first sensors. The controller can be configured to classify a defect detected by one of the fourth sensors into a defect profile based at least in part on segmenting the fourth sensors into a plurality of inspection sensor segments.

Yet a further exemplary embodiment of the present disclosure is directed to a method suitable for use in connection with a winder producing a rolled product from a web. The winder includes a web transport apparatus for conveying a web and a plurality of independent winding modules onto which the web is rolled to form the rolled product during a winding process. Each of the plurality of independent winding modules defines a cross direction generally perpendicular to the direction the web is conveyed by the web transport apparatus. The method includes scanning with at least one sensor a region proximate each of the plurality of independent winding modules; detecting a defect associated with at least one of the plurality of independent winding modules with the at least one sensor; initiating a cut-off for the winding module when a defect is detected; culling the rolled product from the winding module; and transferring the web to a different winding module while the rolled product is being culled from the winding module.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

FIGS. 34-37 illustrate exemplary display information for display on a user interface associated with an exemplary embodiment of the present disclosure.

DETAILED DESCRIPTION

Figure 1:
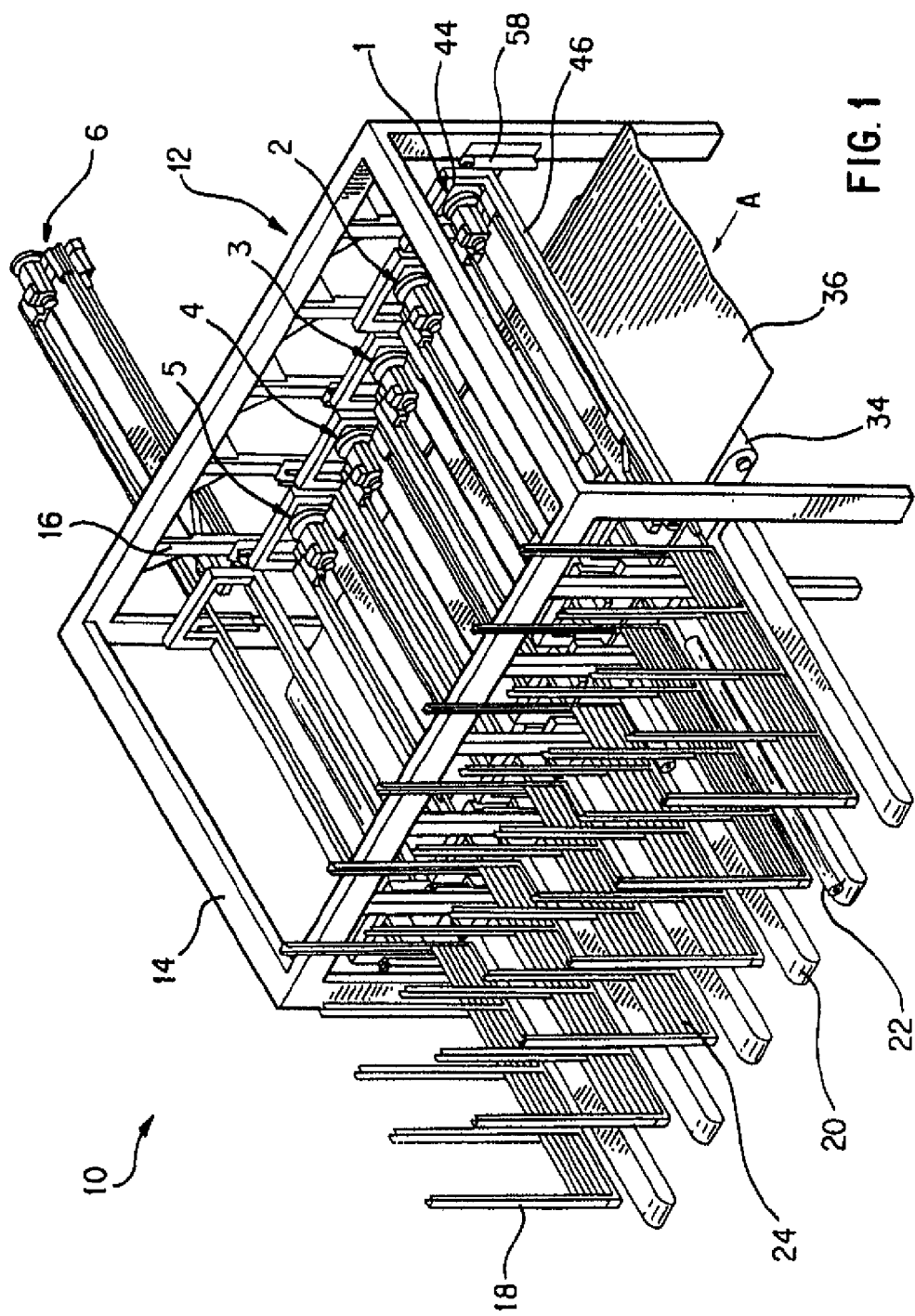
FIG. 1 is a perspective view of one exemplary embodiment of a winder. This winder includes a plurality of independent winding modules that are positioned in the web direction with respect to one another and substantially contained within a modular frame.

Reference will now be made in detail to exemplary embodiments of the invention, one or more examples of which are illustrated in the drawings. Each example is provided by way of explanation of the invention, and not meant as a limitation of the invention. For example, features illustrated or described as part of one exemplary embodiment can be used with another exemplary embodiment to yield still a third exemplary embodiment. It is intended that the present invention include these and other modifications and variations. The terms "including" and "comprising" are used interchangeably and are both meant as open-ended terms.

In several examples herein, registration and inspection methods and systems are discussed in the context of controlling a winder that is capable of winding web from a parent roll to form a rolled product. However, before discussing the structural and operational details of exemplary embodiments of winders, it is important to note that the discussion of particular types and arrangements of machines and functions and tasks performed by such machines is for purposes of example only. Namely, the desired operation of an exemplary winder and exemplary components used to obtain such operation is initially discussed. Further discussion pertaining to exemplary embodiments of winder/rewinders can be found in U.S. patent application Ser. No. 10/085,813, filed on Feb. 28, 2002 and Ser. No. 11/799,043, filed on Apr. 30, 2007, both of which are hereby incorporated by reference. The specification will then set forth asynchronous control principles that can be used to obtain the desired operation of the winders are discussed in more detail. Later in the specification, registration and inspection systems and methods that can be used in accordance with embodiments of the present disclosure will be set forth. It is to be understood that the subject matter set forth herein may be applied to any type or types of machinery or process, regardless of size, arrangement, intended function, and the like, and is not limited to use only with winders/re-winders.

I. Discussion of Exemplary Aspects of a Modular Winding Machine

A winder may comprise a winding module that has a rotating mandrel that engages the leading edge of a moving web. Upon transfer of the leading edge of the web to the core, the winding mandrel is disengaged from the transport apparatus removing any nip pressure for the remainder of the wind. The web may be wound about the core through the rotation of the center driven mandrel. This type of winding is known as center winding. Additionally, the mandrel may be placed onto the web to form and maintain nip pressure between the winding mandrel and the web. The web may be wound about the core through the rotation of the surface driven mandrel. This type of winding is a form of surface winding. As such, the winding module may wind web into a rolled product by center winding, surface winding, and combinations of center and surface winding. This allows for the production of rolled products with varying degrees of softness and hardness.

Also, in several examples, the control system is used to control a winder that has a plurality of independent winding and other modules. Each individual winding module may wind the web such that if one or more modules are disabled, the remaining modules may continue to wind without interruption. This allows for operator servicing and routine maintenance or repairs of a module to be made without shutting down the winder. This configuration has particular advantages in that waste is eliminated and efficiency and speed of the production of the rolled product is improved.

A winding module 12 as shown in FIG. 1 can be used to wind a web 36 and form a rolled product 22. Although a plurality of independent winding modules 12 may be used to produce rolled products 22, the explanation of the functioning of only one winding module 12 is necessary in order to understand the building process of the rolled product 22.

Figure 5:
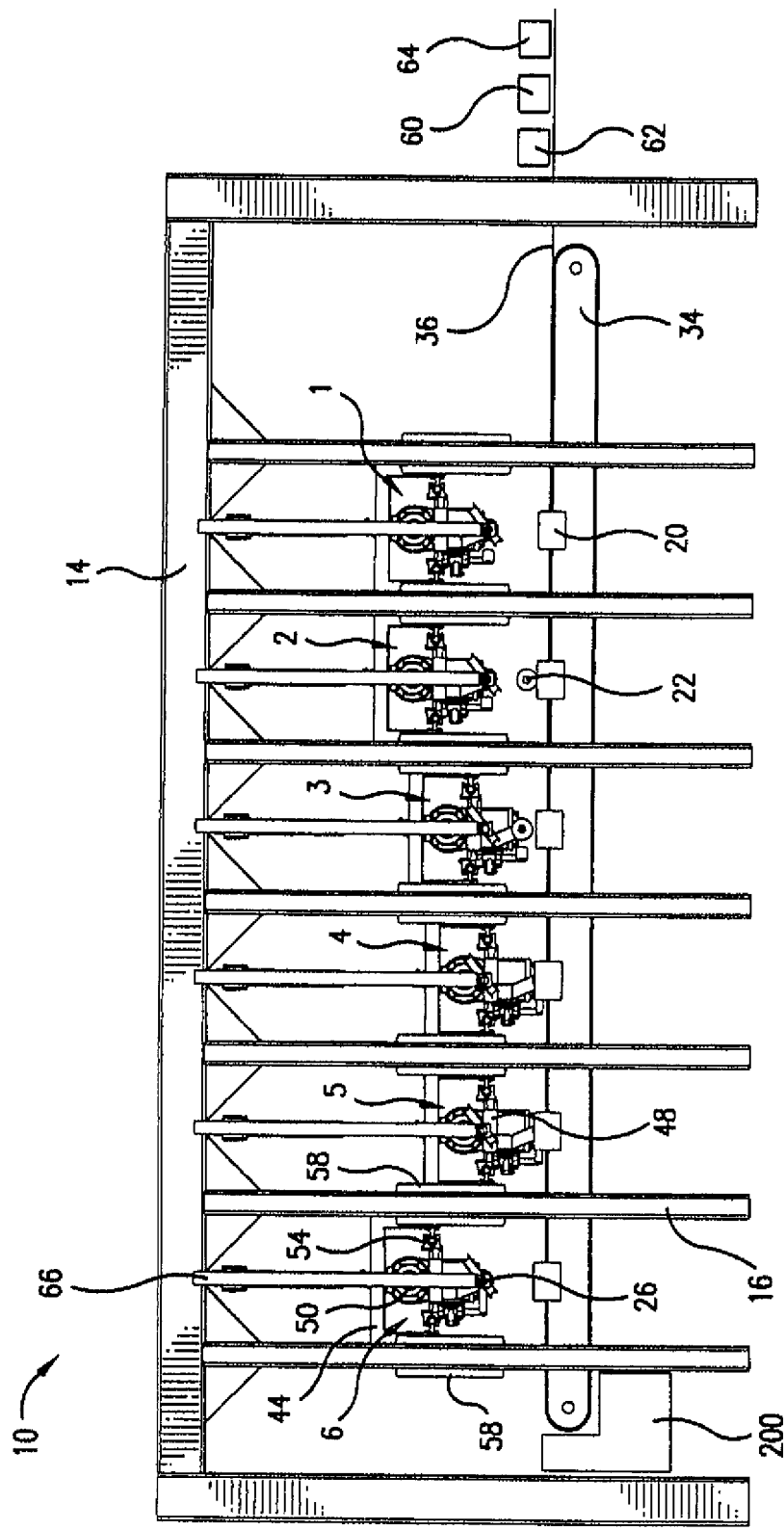
FIG. 5 is a side elevation view of an exemplary embodiment of a winder. The drawing shows winding modules in addition to other modules, which perform functions on a web.
Figure 10:
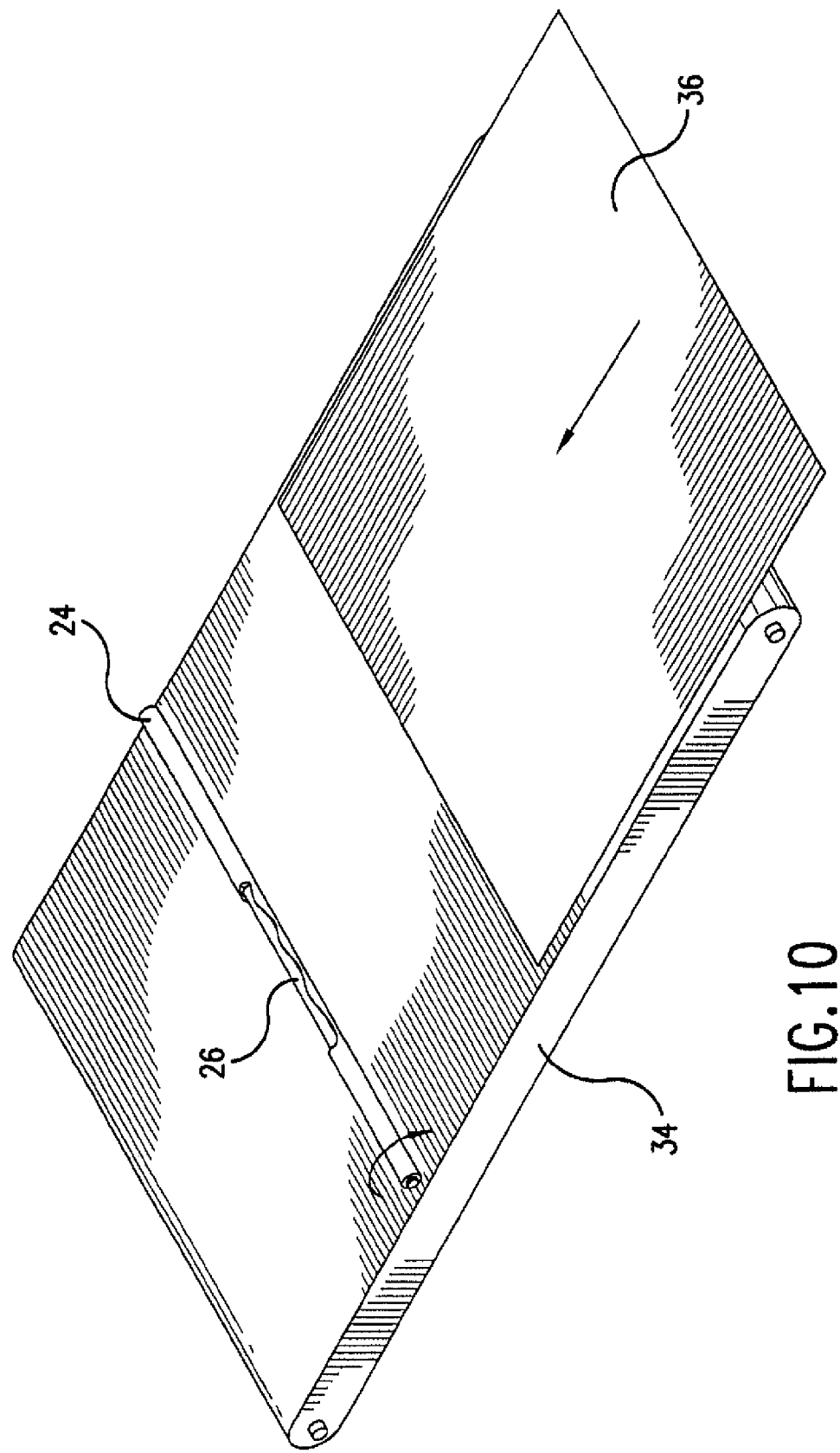
FIG. 10 is a perspective view of a web being transported by a web transport apparatus into proximity with a mandrel having a core.
Figure 15:
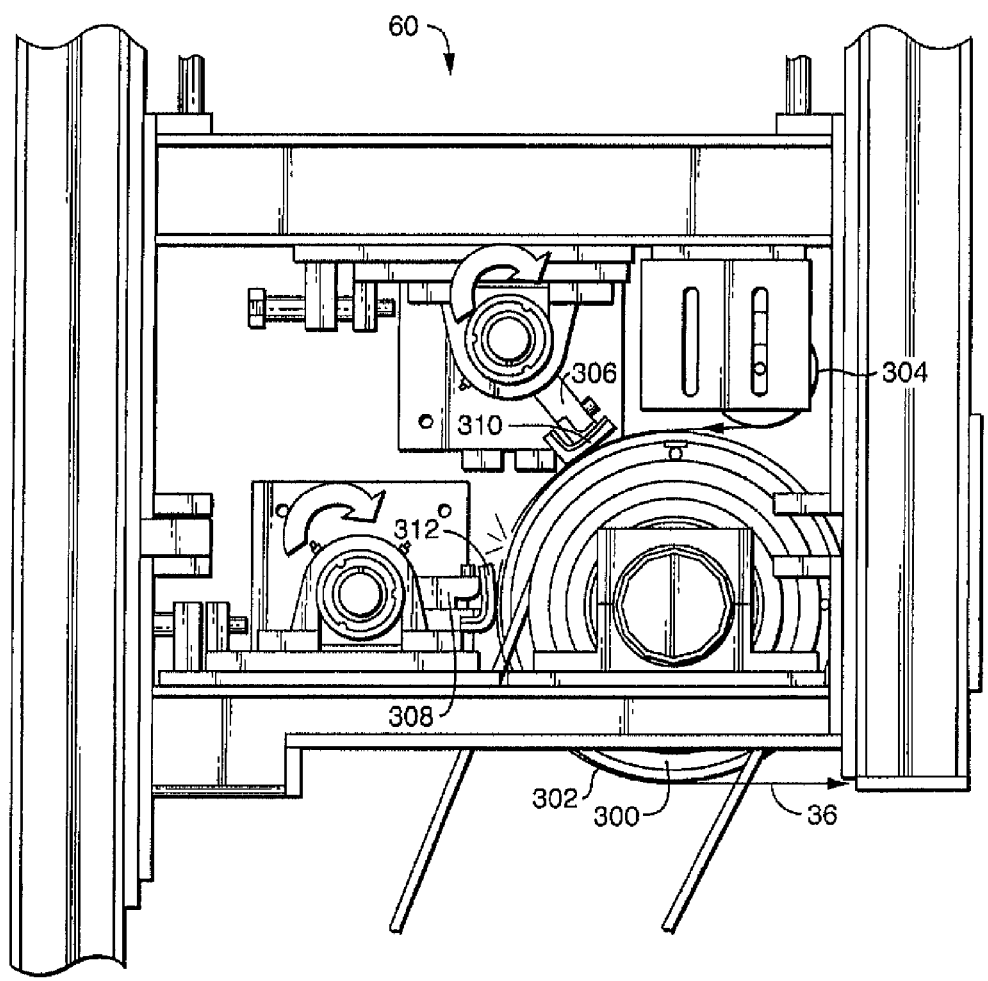
FIG. 15 is a side view of one embodiment of an apparatus for breaking a moving web.
Figure 16:
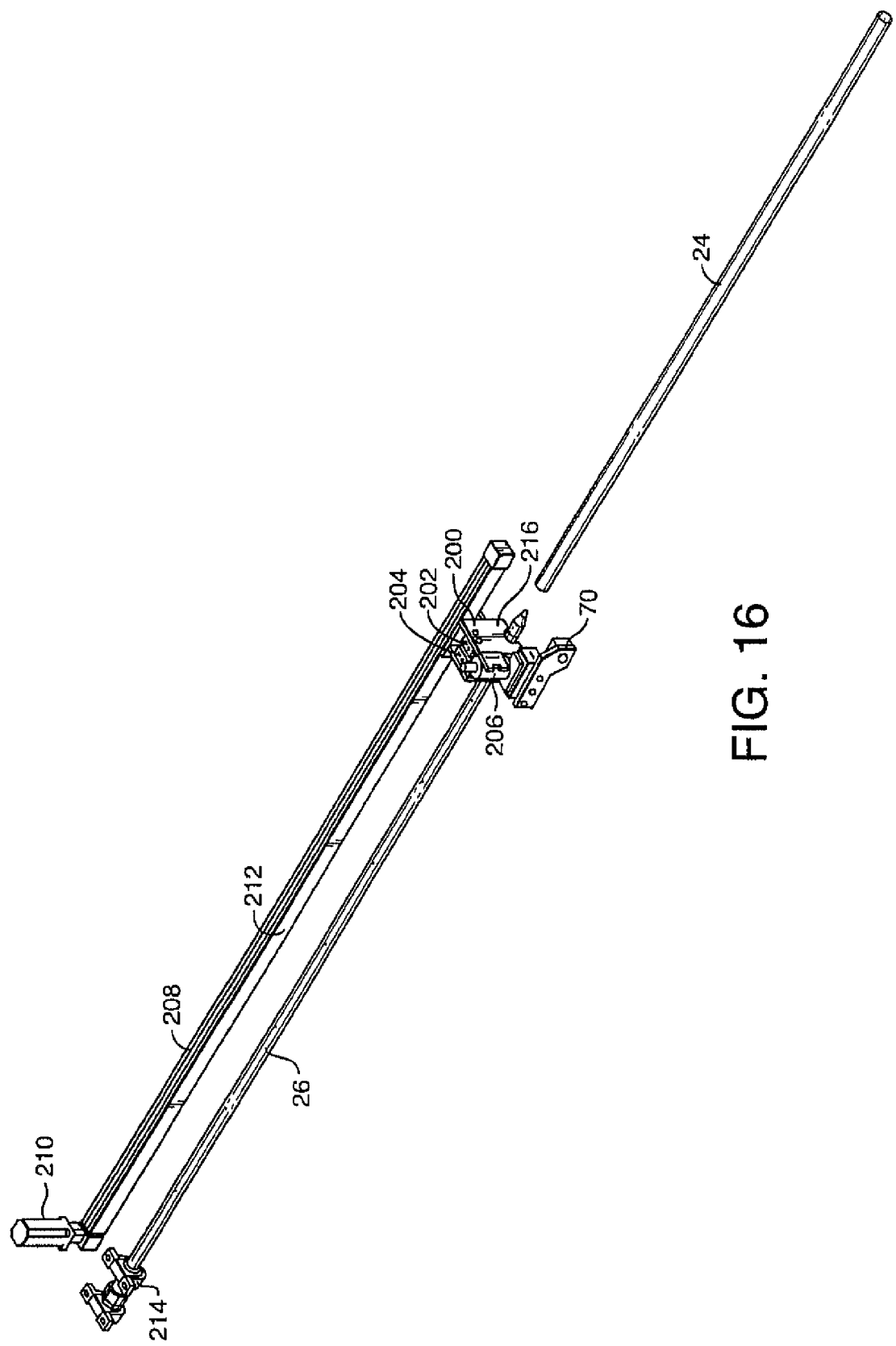
FIGS. 16 through 23 are perspective views of an alternative embodiment of a core loading apparatus showing sequentially a core being loaded onto a mandrel and then a finished product log being stripped from the mandrel.
Figure 17:
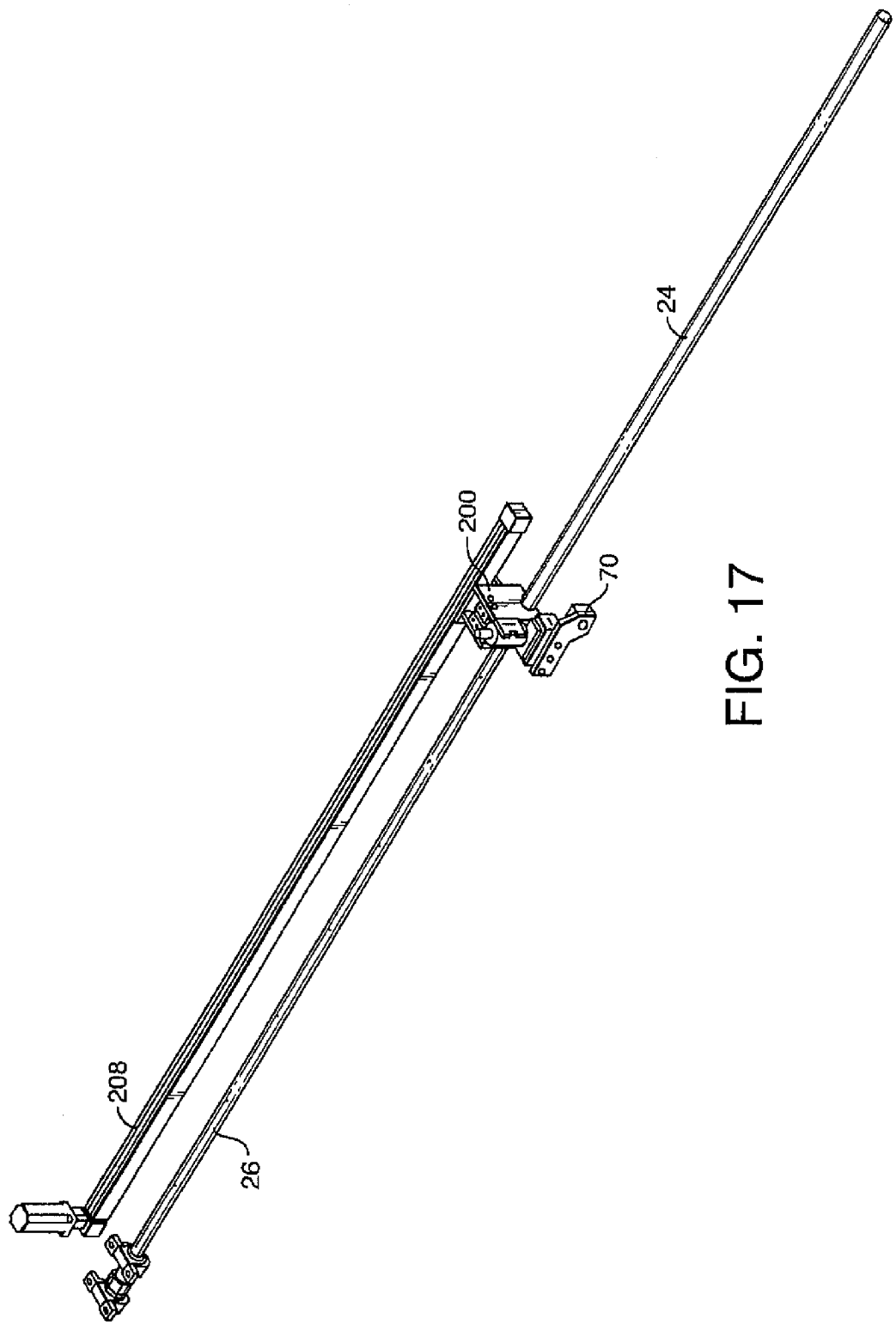
Figure 18:
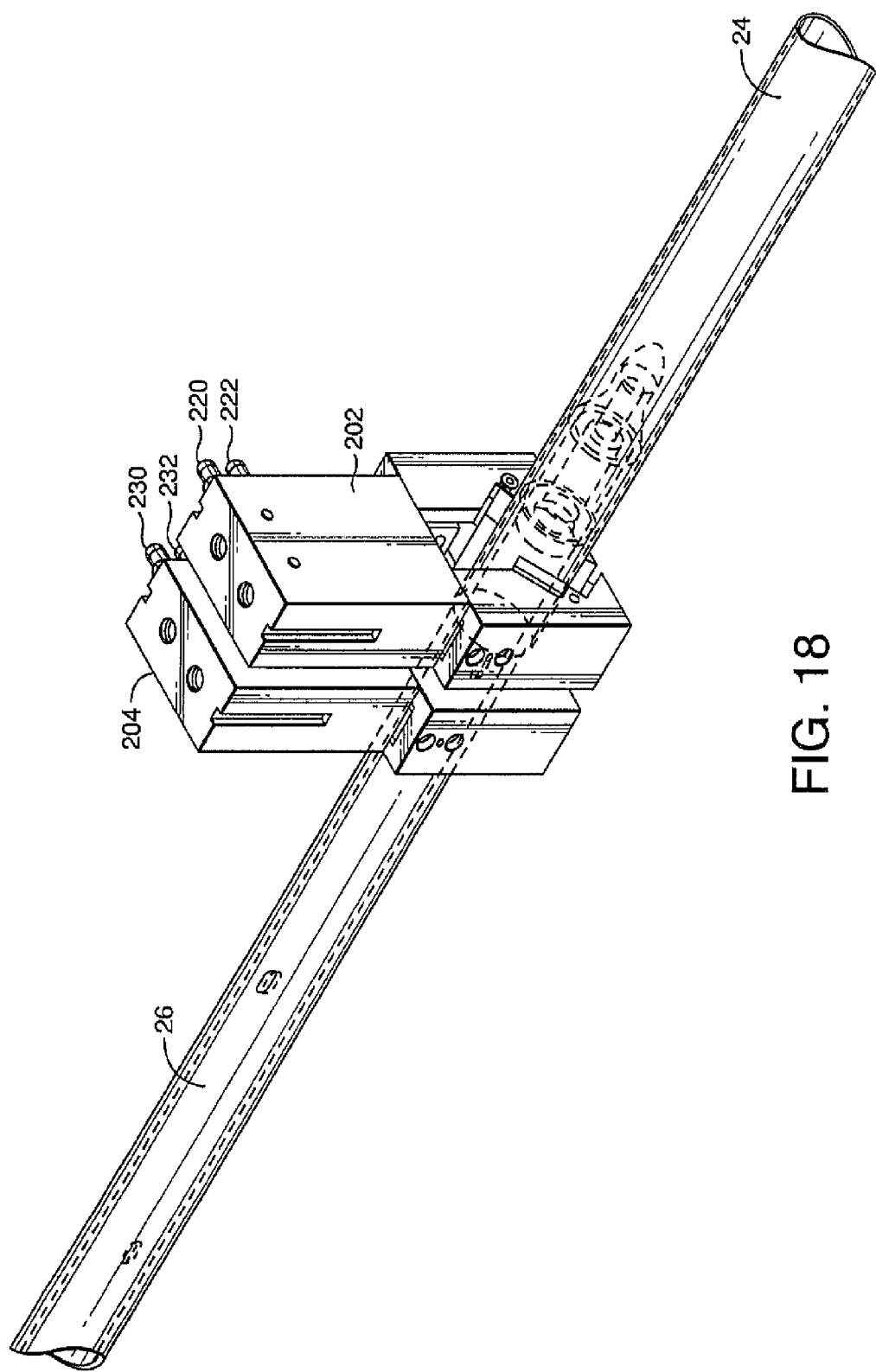

Referring to FIG. 5, a web 36 is transported by a web transport apparatus 34 as shown. The web 36 is cut to a predetermined length by use of, for instance, a cut-off module 60 may be configured as a pinch bar as is disclosed in U.S. Pat. No. 6,056,229. However, any other suitable way to cut the web 36 to a desired length may be employed. For example, another embodiment of a cut-off module 60 is shown in FIG. 15 which will be described in more detail below. Additionally, the web 36 may be perforated by a perforation module 64 and have adhesive applied thereto by a transfer/tail seal adhesive applicator module 62 as also shown in FIG. 5. Additionally, in other exemplary embodiments, adhesion may be applied to the core 24 as opposed to the web 36. Referring back to FIG. 10, the mandrel 26 is lowered into a ready to wind position and awaits the web 36. During, prior to, or after lowering, the mandrel 26 is accelerated so that the speed of the mandrel 26 matches the speed of the web 36. Mandrel 26 has a core 24 located thereon. The core 24 is moved into contact with the leading edge of the web 36. The web 36 is then wound onto core 24 and is attached to core 24 by, for instance, the adhesive previously applied or and by the contact between the core 24 and the web 36.

Figure 11:
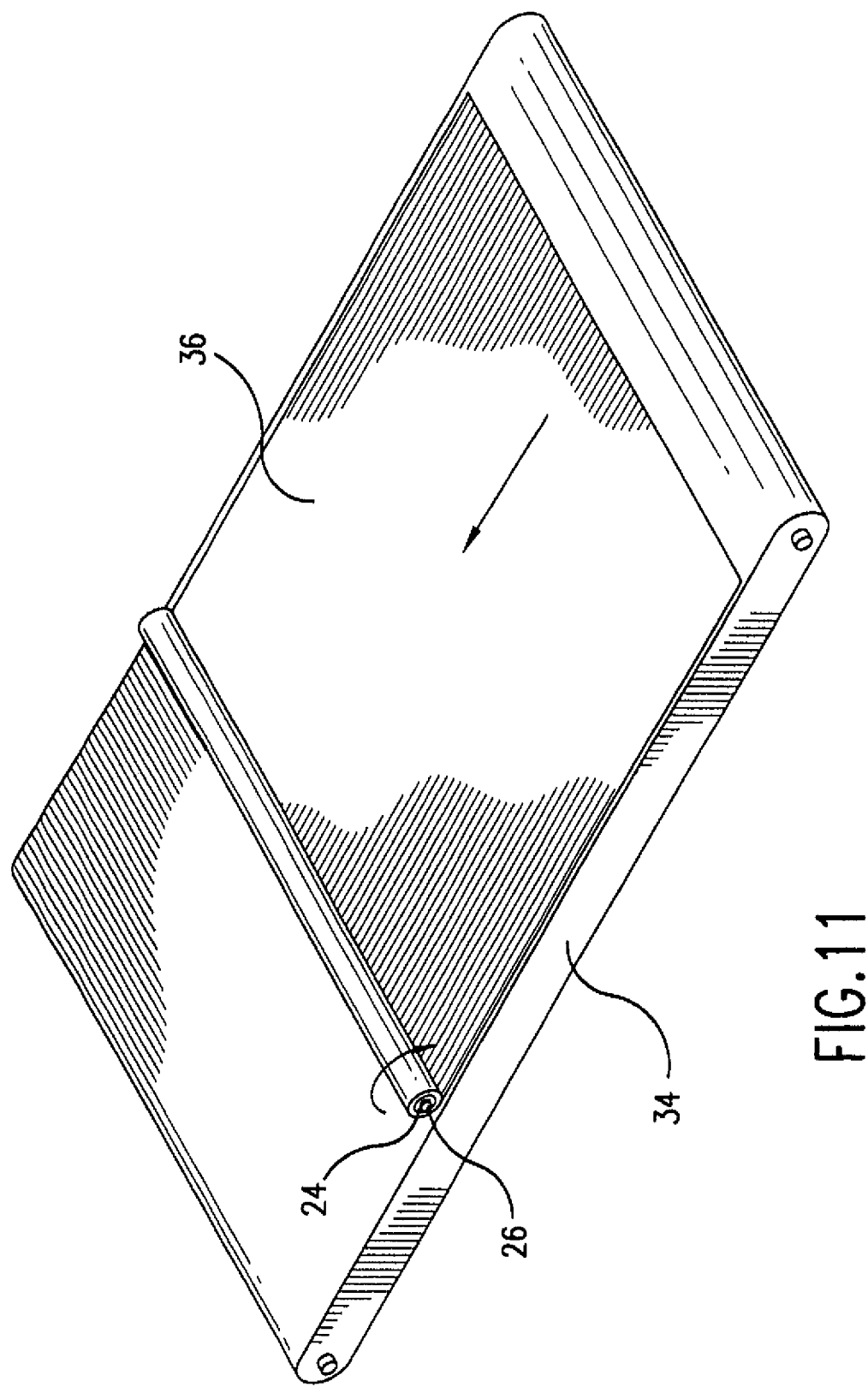
FIG. 11 is a perspective view of a rotating mandrel and core that are winding a web.

FIG. 11 shows the web 36 being wound onto the core 24. The winding of the web 36 onto core 24 may be controlled by the pressing of the core 24 onto the web transport apparatus 34 to form a nip. The magnitude with which the core 24 is pressed onto the web transport apparatus 34 creates a nip pressure that can control the winding of the web 36 onto the core 24. Additionally, the incoming tension of the web 36 can be controlled in order to effect the winding of the web 36 onto the core 24. Another control that is possible to wind the web 36 onto the core 24 involves the torque of the mandrel 26. Varying the torque on the mandrel 26 will cause a variance in the winding of the web 36 onto the core 24. Some or all of these types of winding controls, "nip, tension, and torque differential", can be employed, either alone or in combination. As will be discussed below, these and other controls can be achieved in multiple ways, including by varying cam and other motion profiles, and/or by varying the relative timing of virtual master signals.

If not done before, the web 36 may be cut once the desired length of web 36 has been wound onto the core 24. At this point, the leading edge of the next web 36 will be moved by the web transport apparatus 34 into contact with another winding module 12 (not shown in FIG. 11).

Figure 2:
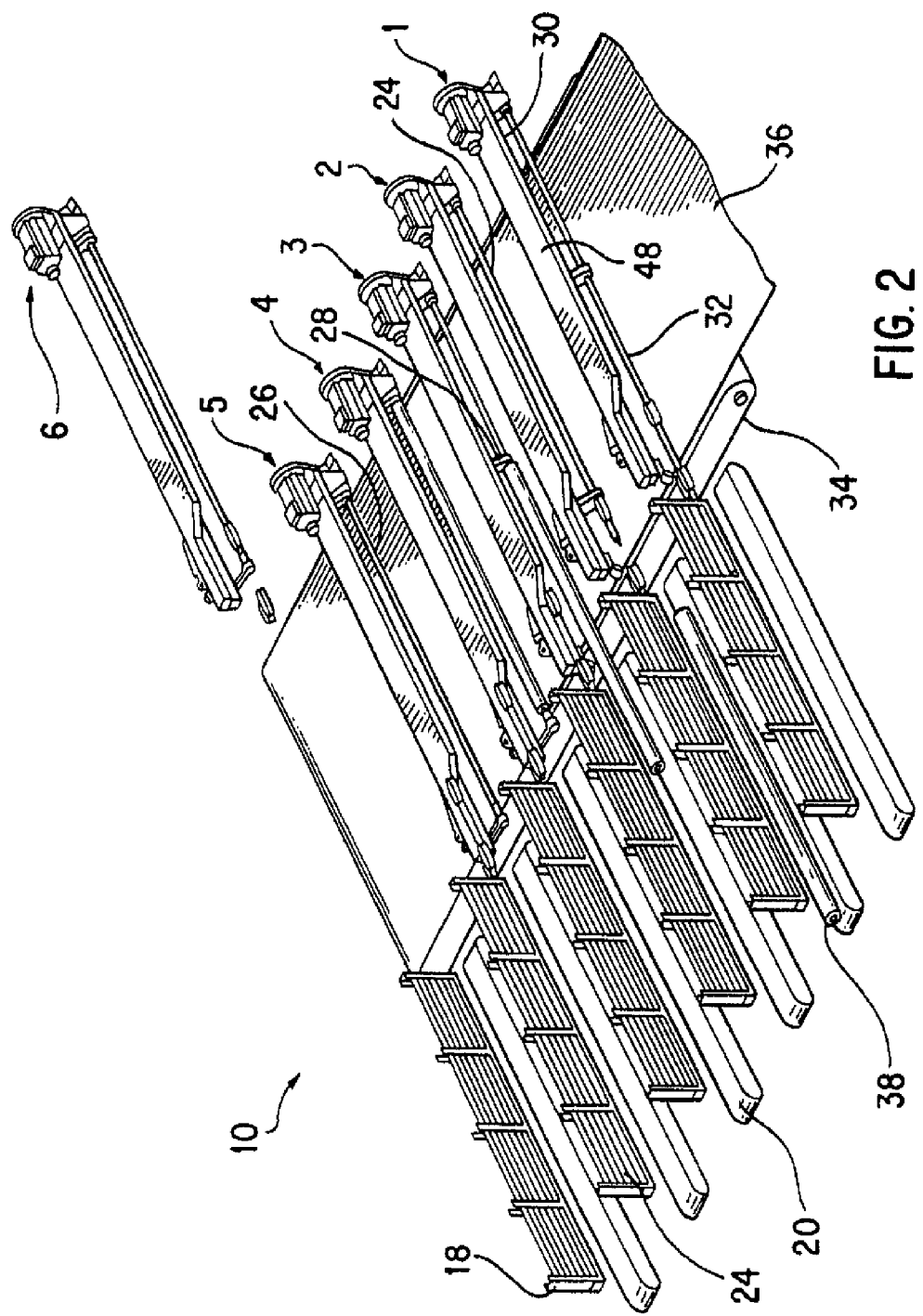
FIG. 2 is a perspective view of an exemplary embodiment of a winder. This drawing shows a plurality of independent winding modules, which are performing the various functions of a log winding cycle.
Figure 12:
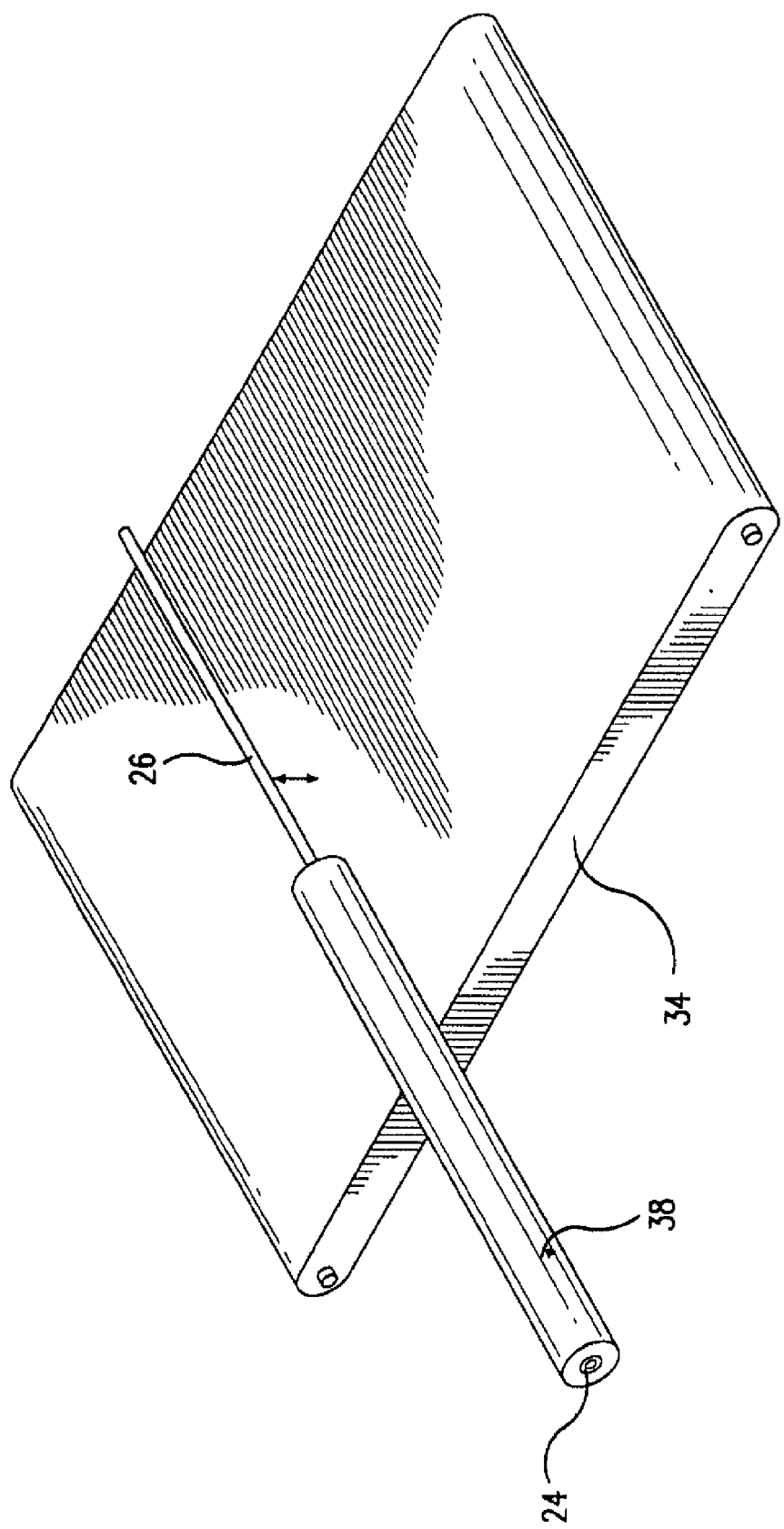
FIG. 12 is a perspective view of a rolled product with a core that is shown being stripped from a mandrel.

FIG. 12 shows the mandrel 26 being moved from a winding position to a position above the web transport apparatus 34 for a log-stripping and core loading operation. The wound length of web 36 is shown in FIG. 12 as being a rolled product 38 with a core 24. Now, a stripping function is carried out that moves the rolled product 38 with a core 24, known in the art as a "log," off of the mandrel 26. This mechanism is shown as a product stripping apparatus 28 in FIG. 2. The rolled product 38 with a core 24 is moved onto a rolled product transport apparatus 20 as shown in FIGS. 1 and 2. In other embodiments, the log does not include a core 24.

Figure 13:
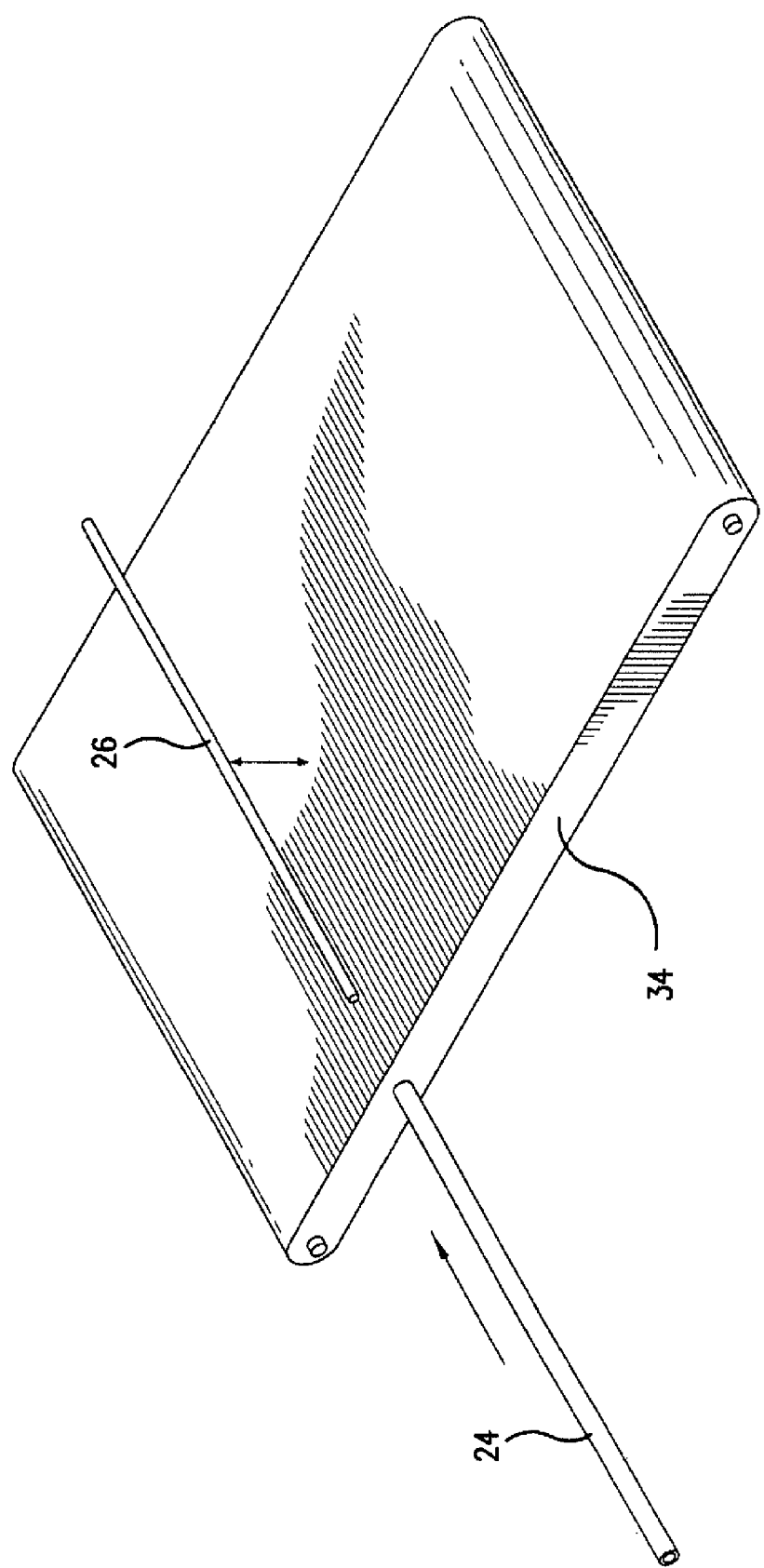
FIG. 13 is a perspective view of a mandrel that is in position to load a core.

Once the rolled product 38 with a core 24 is stripped from the mandrel 26, the mandrel 26 is moved into a core loading position as shown in FIG. 13. The product stripping apparatus 28 is shown in more detail in FIG. 2. Once the product stripping apparatus 28 finishes stripping the rolled product 38 with a core 24, the product stripping apparatus 28 is located at the end of the mandrel 26, which stabilizes the mandrel and the core loading/log stripping apparatus. In addition, the product stripping apparatus 28 helps to properly locate the end point of mandrel 26 for the loading of a core 24.

Figure 14:
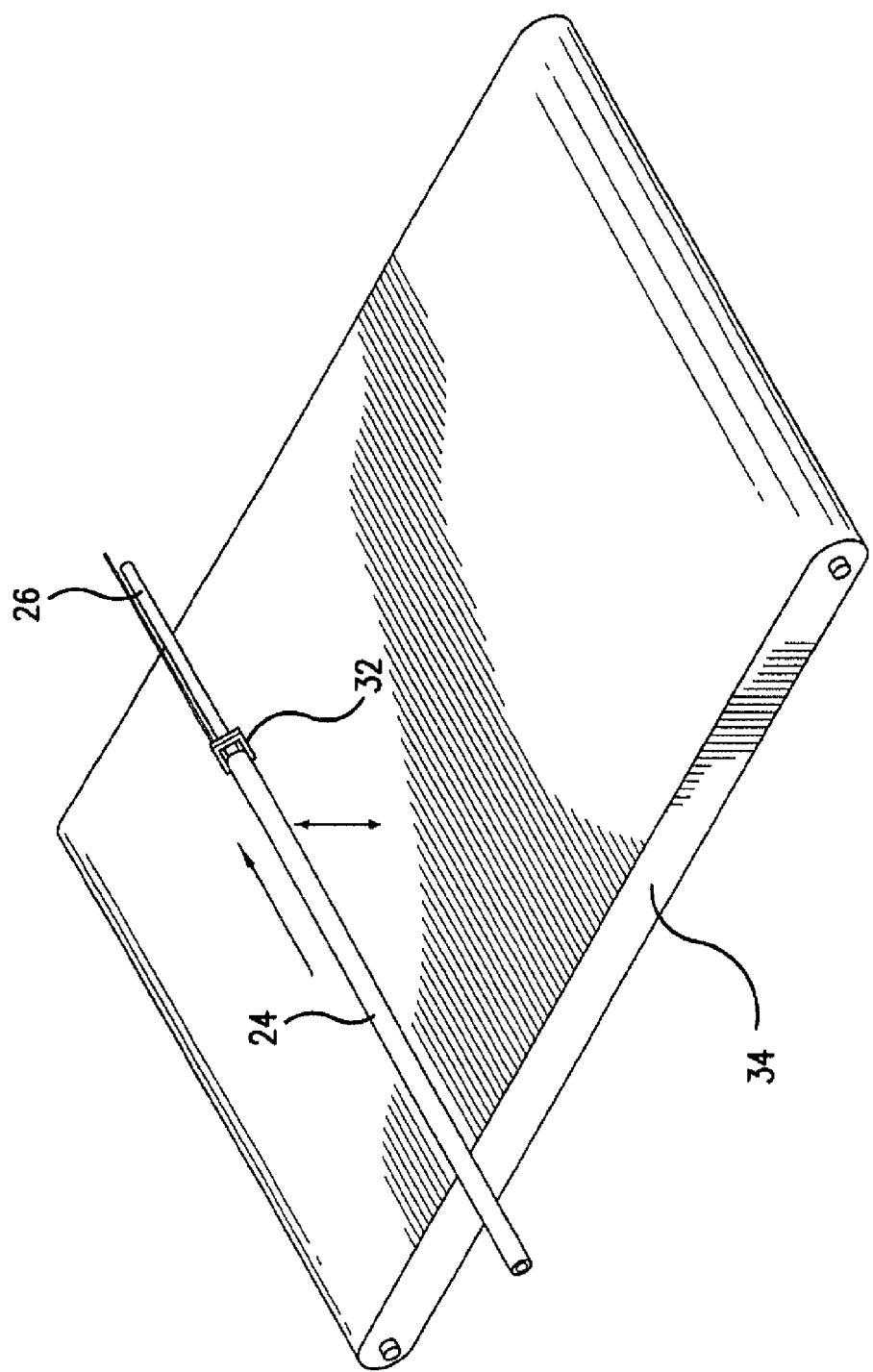
FIG. 14 is a perspective view that shows a core being loaded onto a mandrel via a core loading apparatus.

FIG. 14 shows one embodiment of a core 24 being loaded onto the mandrel 26. The loading of the core 24 is affected by a core loading apparatus 32. The product stripping apparatus may also serve as a core loading apparatus. The core loading apparatus 32 may be simply a frictional engagement between the core loading apparatus 32 and the core 24. However, the core loading apparatus 32 can be configured in other ways known in the art.

FIG. 1 shows an exemplary embodiment of a winder as a "rewinder" 10 with a plurality of independent winding modules 12 arranged in a linear fashion with respect to one another. A frame 14 supports the plurality of independent winding modules 12. A web transport apparatus 34 is present which transports the web 36 for eventual contact with the plurality of independent winding modules 12. The frame 14 comprises a plurality of posts 16 onto which the plurality of independent winding modules 12 are (in this example) slidably engaged and supported. The frame 14 may also be comprised of modular frame sections that would engage each other to form a rigid structure. The number of modular frame sections would coincide with number of winding modules utilized.

Situated adjacent to the frame 14 are a series of core supplying apparatuses 18. A plurality of cores 24 may be included within each core supplying apparatus 18. These cores 24 may be used by the plurality of independent winding modules 12 to form rolled products 22. Once formed, the rolled products 22 may be removed from the plurality of independent winding modules 12 and placed onto a rolled product transport apparatus 20. The rolled product transport apparatus 20 is located proximate to the frame 14 and web transport apparatus 34.

FIG. 2 shows a rewinder 10 as substantially disclosed in FIG. 1 but having the frame 14 and other parts removed for clarity. In this exemplary embodiment, the plurality of independent winding modules 12 are composed of six winding modules 1-6. However, it is to be understood that more or fewer independent winding modules 12 may be used in other embodiments.

Each winding module 1-6 is shown performing a different function. Winding module 1 is shown in the process of loading a core 24 thereon. The plurality of independent winding modules 12 are provided with a core loading apparatus for placing a core 24 onto a mandrel 26 of the plurality of independent winding modules 12. Any number of variations of a core loading apparatus may be utilized. For instance, the core loading apparatus may be a combination of a rod that extends into the core supplying apparatus 18 and pushes a core 24 partially onto the mandrel 26 and a mechanism attached to the linear actuator of the product stripping apparatus 28 that frictionally engages and pulls the core 24 the remaining distance onto the mandrel 26. As shown in FIG. 2, winding module 1 is in the process of pulling a core 24 from the core supplying apparatus 18 and placing the core 24 on mandrel 26.

FIGS. 16-24, show one embodiment of a core loading apparatus. In particular, FIGS. 16-23 illustrate a sequence of loading a core 24 onto a mandrel 26 in order to form a rolled product 22 which is then stripped off the mandrel 26.

The mandrel 26 as shown is supported on one end by a bearing assembly 214. On the opposite end, the mandrel 26 is engagable with a cupping arm 70. The cupping arm 70 is in communication with an actuator (such as a motor) 206. The actuator 206 causes the cupping arm to rotate thereby engaging and disengaging the end of the mandrel 26. For example, in FIG. 20, the cupping arm 70 is shown in the engaged position for supporting the end of the mandrel 26. The cupping arm 70 is used to engage and support the end of the mandrel 26 during winding. When loading the core 24 or when stripping a rolled product from the mandrel 26, on the other hand, the cupping arm 70 disengages the mandrel 26. When the cupping arm 70 is disengaged from the mandrel 26, the stabilizer 204 of the core loading assembly engages the mandrel for supporting the mandrel while a core is being loaded.

The core loading assembly 200 and the actuator 208 can be placed in communication with a controller, such as a microprocessor that is capable of actuating a sequence for loading a core onto the mandrel at a desired position and then stripping a rolled product from the mandrel. As will be noted below, in some embodiments, each independent winding module 12 may be associated with a respective module controller that comprises the microprocessor actuating the loading/stripping sequence. One sequence for loading a core onto the mandrel is illustrated in FIGS. 16-23.

Figure 19:
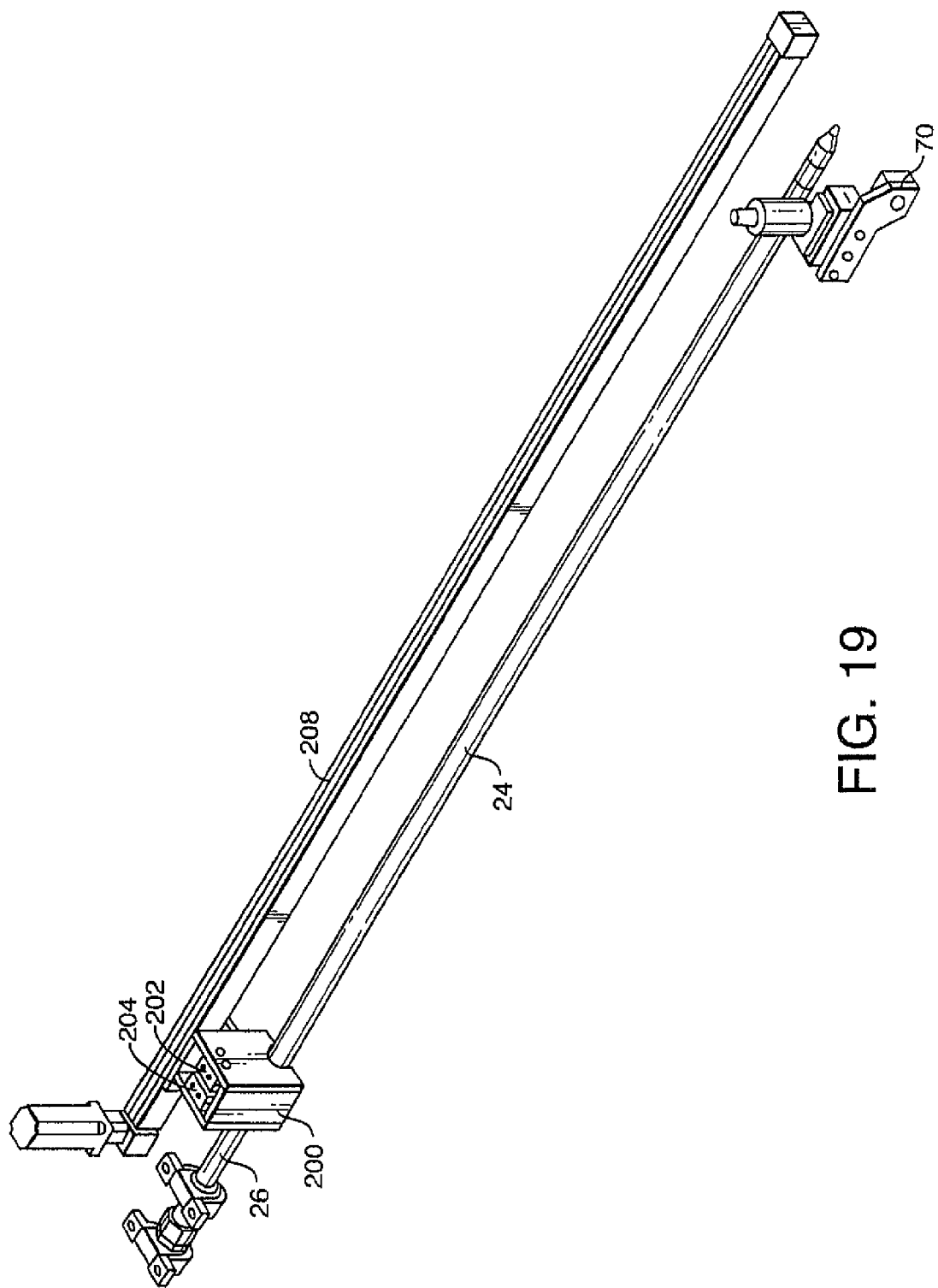
Figure 20:
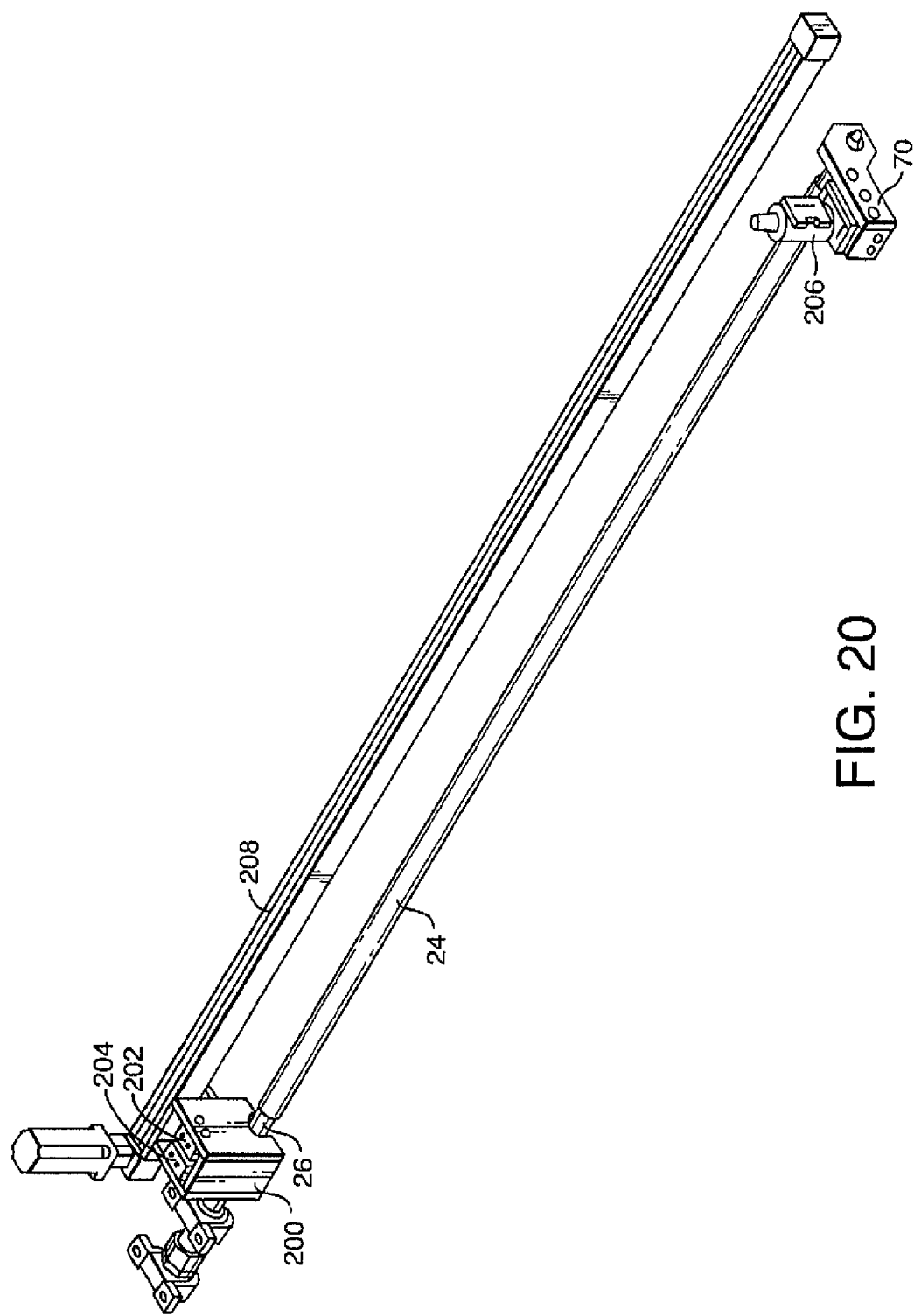

Once the core is engaged, the core 24 is pulled onto the mandrel 26 as shown in FIG. 19 using the actuator 208. The actuator 208 can be configured to place the core 24 at a particular position on the mandrel 26. Once the core 24 is positioned into a particular position, the gripping device 202 can release the core as shown in FIG. 20. The core loading assembly 200 is then moved further to the end of the mandrel to prevent interference with the core 24 as a web of material is wound onto the core. Also, as shown in FIG. 20, the cupping arm 70 is moved back into engagement with the mandrel 26.

Figure 21:
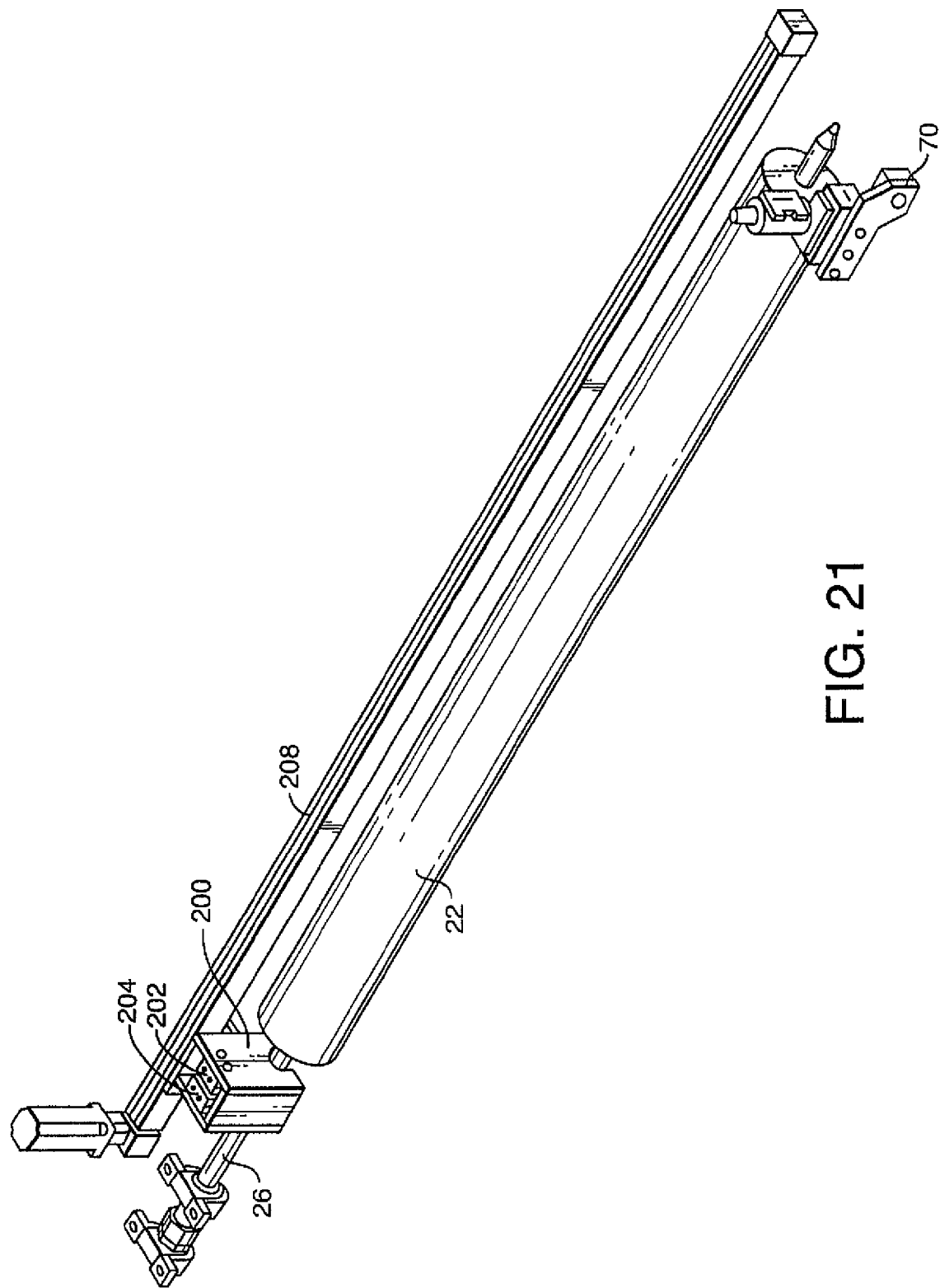
Figure 22:
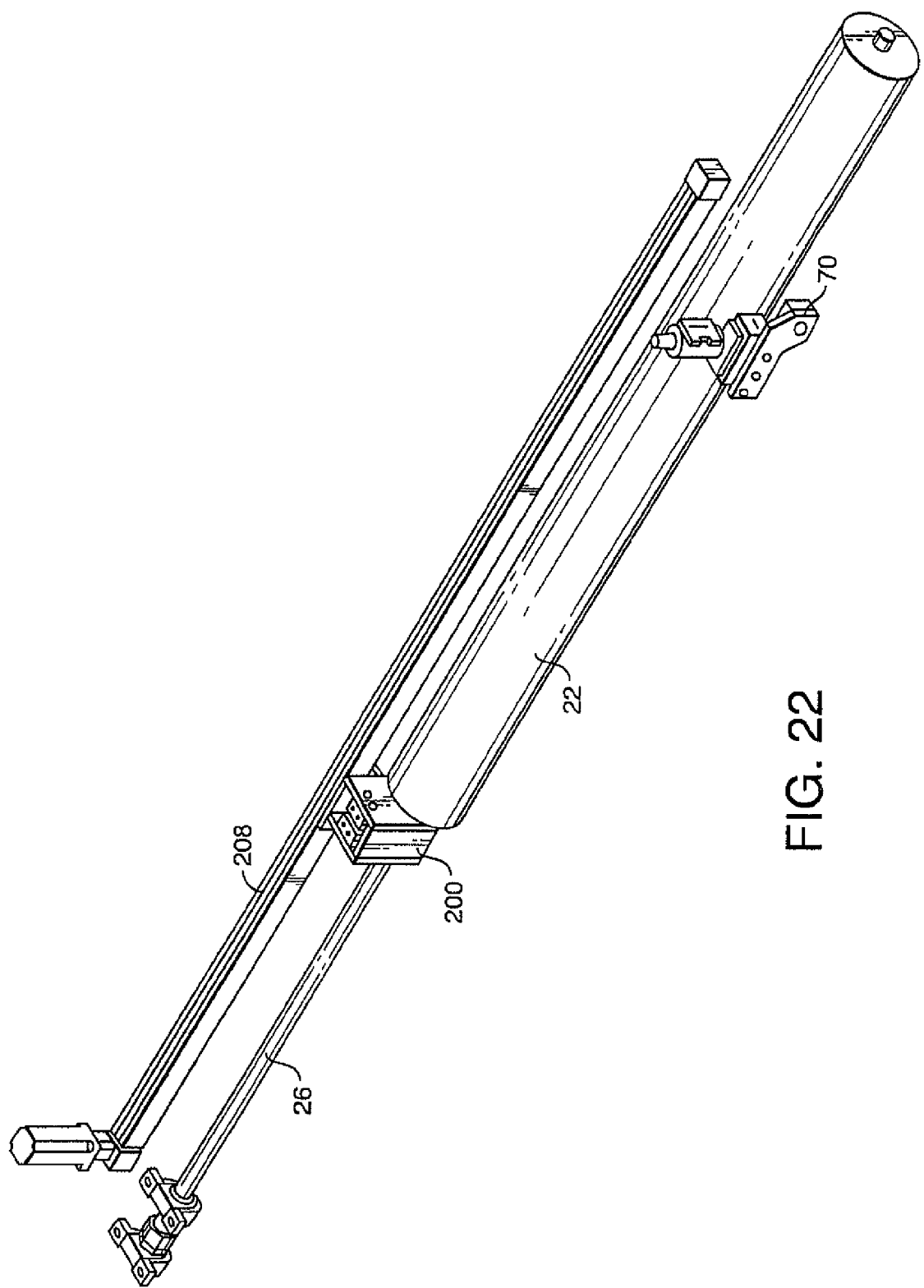
Figure 23:
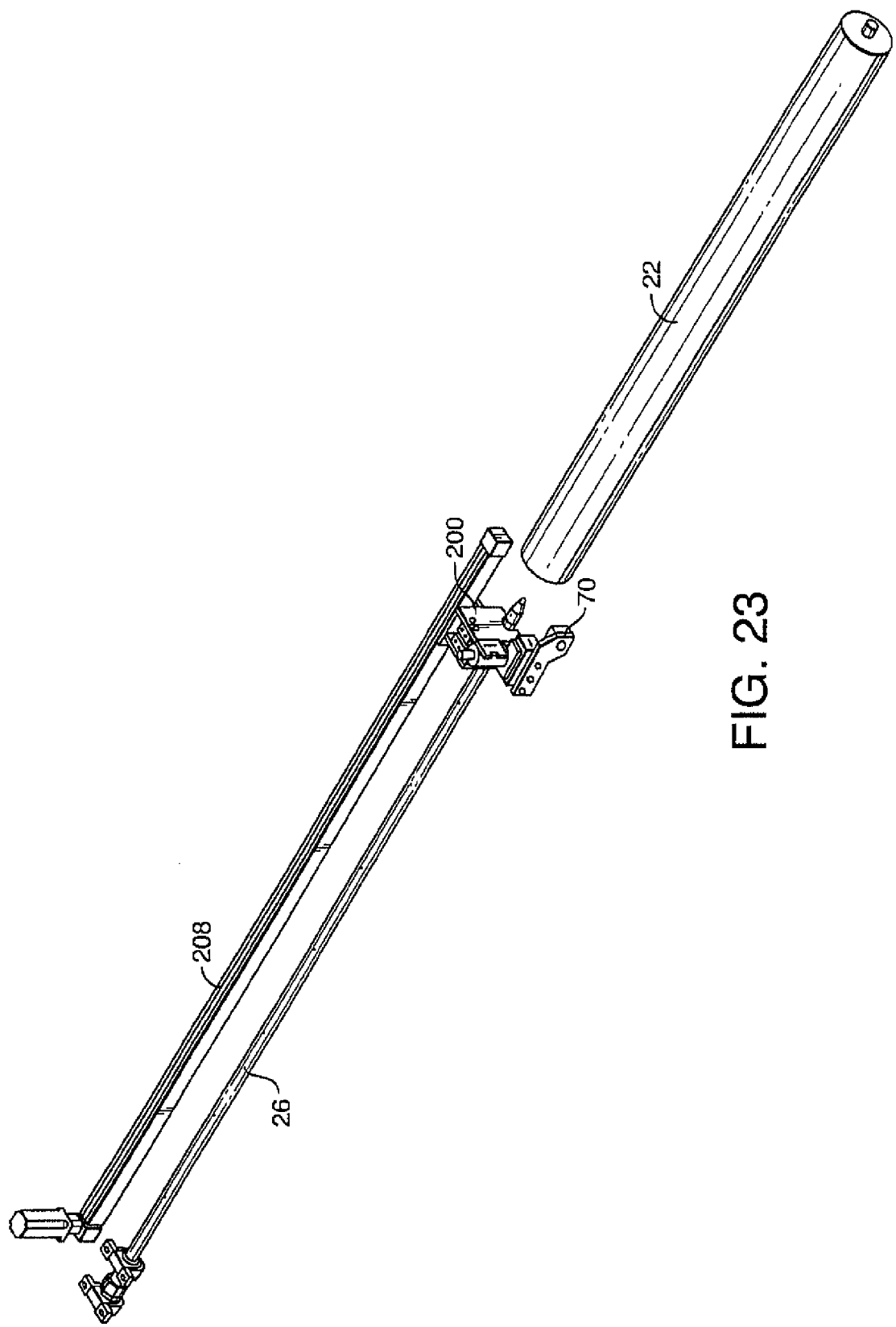
Figure 24:
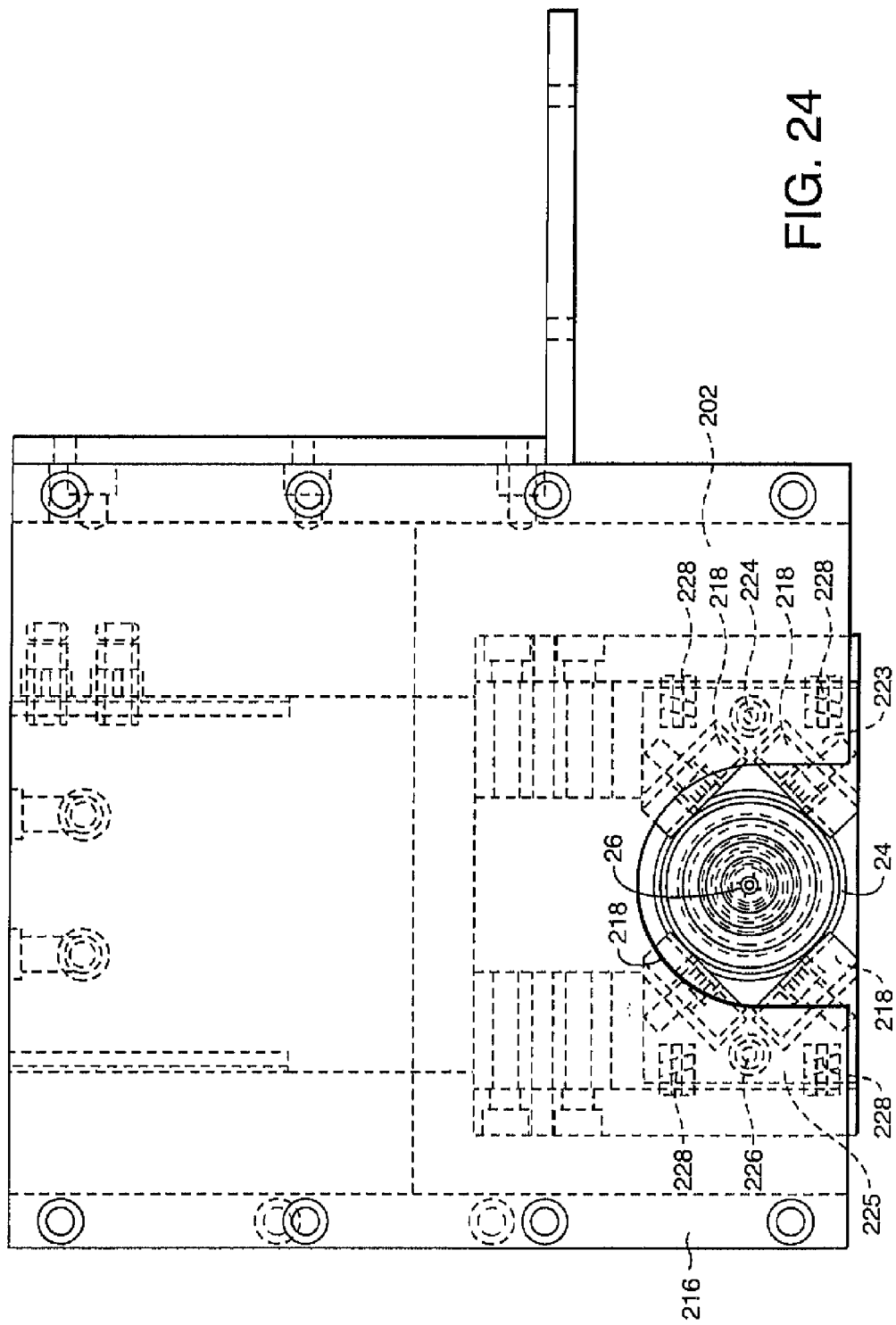
FIG. 24 is a side view of the core loading assembly illustrated in FIGS. 16 through 23.

Once the core 24 is loaded onto the mandrel 26 as shown in FIG. 20, a rolled product 22 is formed on the mandrel as shown in FIG. 21. Of particular advantage, in this embodiment, the core loading assembly 200 can also be used to strip the rolled product 22 from the mandrel 26. For instance, as shown in FIG. 22, once the rolled product 22 is formed, the actuator 208 can move the core loading assembly 200 into engagement with the rolled product for sliding the rolled product off the mandrel 26 as shown in FIG. 23. The rolled product 22 once stripped from the mandrel 26 can then be fed to a rolled product transfer apparatus. Of particular advantage, the core loading assembly 200 stabilizes the mandrel as it pushes the rolled product off of the mandrel. In particular, the core loading assembly 200 holds the open free end of the mandrel which reduces the whip of the mandrel and therefore prevents against misalignments. Further, once the rolled product is stripped from the mandrel, the core loading assembly 200 is in a position for engaging and pulling a new core onto the mandrel.

Referring back to FIG. 2, winding module 2 is shown as having removed the rolled product 22 from its mandrel 26. The rolled product 22 is placed onto a rolled product transport apparatus 20. In this case, the rolled product 22 is a rolled product with a core 38. Such a rolled product with a core 38 is a rolled product 22 that is formed by having the web 36 being spirally wrapped around a core 24. It is to be understood that the rolled product 22 may also be a rolled product that does not have a core 24 and instead is simply a solid roll of wound web 36. It may also be the case that the rolled product 22 does not include a core 24, but has a cavity in the center of the rolled product 22. Various configurations of rolled product 22 may thus be formed.

Winding module 4 is shown as being in the process of winding the web 36 in order to form the rolled product 22. This winding process may be center winding, surface winding, or a combination of center and surface winding. These processes will be explained in greater detail below.

Winding module 5 is shown in a position where it is ready to wind the web 36 once the winding module 4 finishes winding the web 36 to produce a rolled product 22. In other words, winding module 5 is in a "ready to wind" position.

Winding module 6 is shown in FIG. 1 in a "racked out" position. It may be the case that winding module 6 has either faulted or is in need of routine maintenance and is therefore moved substantially out of frame 14 for access by maintenance or operations personnel. As such, winding module 6 is not in a position to wind the web 36 to produce rolled product 22, but the other five winding modules 1-5 are still able to function without interruption to produce the rolled product 22. By acting as individual winders, the plurality of independent winding modules 12 allow for uninterrupted production even when one or more of the winding modules becomes disabled. As will be discussed in further detail below, operation of each winding module may be based on the value of a winding module virtual master signal which can be synchronized to a system virtual master signal as desired. When one or more modules become disabled, the virtual master(s) of the disabled module(s) can be de-synchronized so that the module(s) cease operation while the remaining modules (if any) continue operation.

Figure 4:
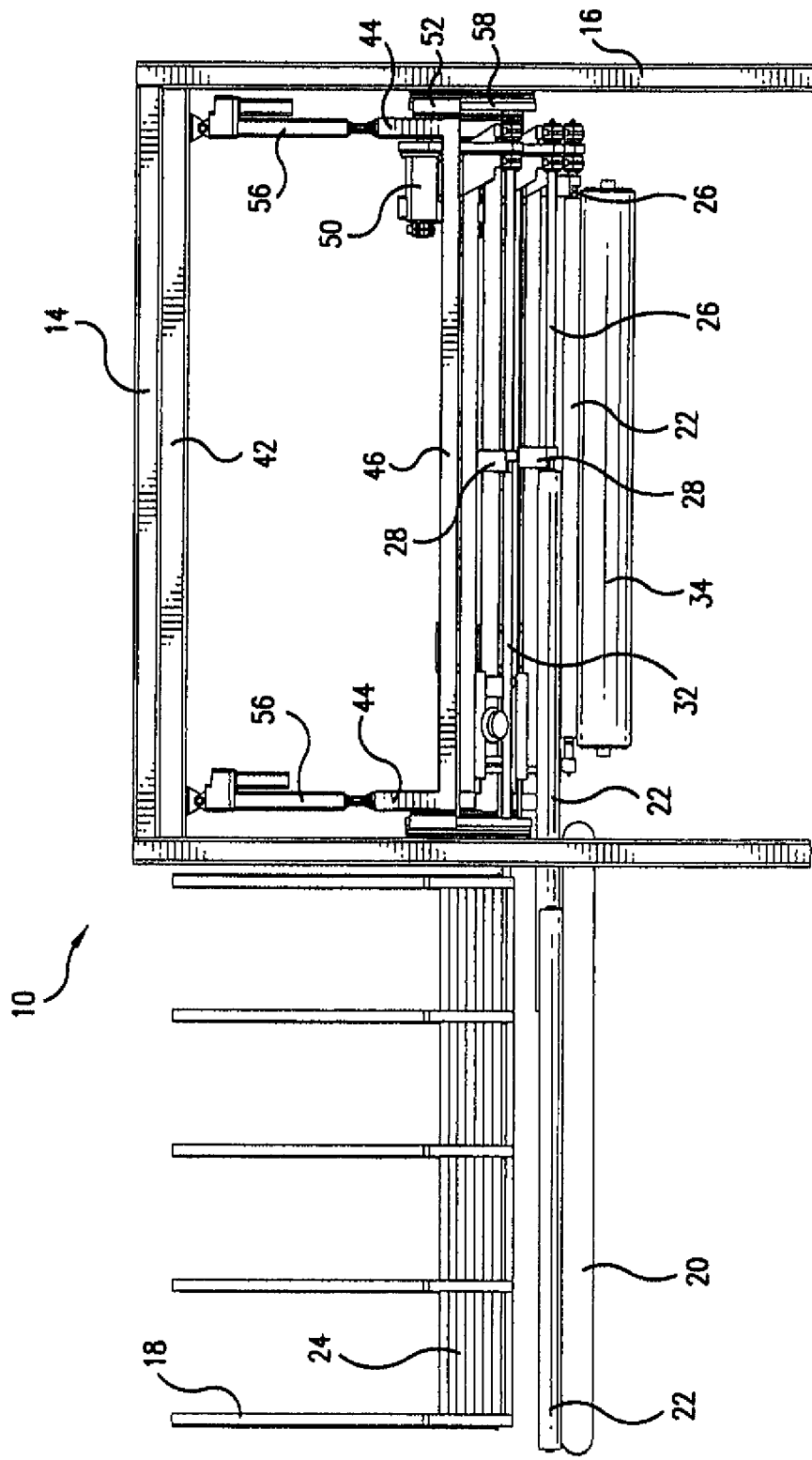
FIG. 4 is a front elevation view of an exemplary embodiment of a winder. The drawing shows a plurality of independent winding modules linearly situated with respect to one another and performing the various functions of a log winding cycle.

Each winding module 12 may have a positioning apparatus 56 (FIG. 4). The positioning apparatus 56 moves the winding module perpendicularly with respect to web transport apparatus 34, and in and out of engagement with web 36. Although the modules 12 are shown as being moved in a substantially vertical direction, other exemplary embodiments of a winder may have the modules 12 moved horizontally or even rotated into position with respect to web 36. Other ways of positioning the modules 12 can be envisioned.

Therefore, each of the plurality of independent winding modules 12 may be a self-contained unit and may perform the functions as described with respect to the winding modules 1-6. Winding module 1 may load a core 24 onto the mandrel 26 if a core 24 is desired for the particular rolled product 22 being produced. Next, the winding module 1 may be linearly positioned so as to be in a "ready to wind" position. Further, the mandrel 26 may be rotated to a desired rotational speed and then positioned by the positioning apparatus 56 in order to initiate contact with the web 36. The rotational speed of the mandrel 26 and the position of the winding module 1 with respect to the web 36 may be controlled during the building of the rolled product 22. After completion of the wind, the position of the module 1 with respect to the web 36 will be varied so that the winding module 1 is in a position to effect removal of the rolled product 22. The rolled product 22 may be removed by the product stripping apparatus 28 such that the rolled product 22 is placed on the rolled product transport apparatus 20. Finally, the winding module 1 may be positioned such that it is capable of loading a core 24 onto the mandrel 26 if so desired. Again, if a coreless rolled product were to be produced as the rolled product 22, the step of loading a core 24 would be skipped. It is to be understood that other exemplary embodiments, the core 24 loading operation and the rolled product 22 stripping operation occur in the same or different positions with regard to the mandrel 26.

The plurality of independent winding modules 12 may be adjusted in order to accommodate for the building of the rolled product 22. For instance, if surface winding were desired, the pressure between the rolled product 22 as it is being built and the web transport apparatus 34 may be adjusted by the use of the positioning apparatus 56 during the building of the rolled product 22.

Utilizing a plurality of independent winding modules 12 allows for a rewinder 10 that is capable of simultaneously producing rolled product 22 having varying attributes. For instance, the rolled products 22 that are produced may be made such that they have different sheet counts. Also, the rewinder 10 can be run at both high and low cycle rates with the modules 12 being set up in the most efficient manner for the rolled product 22 being built. In order to use asynchronous control principles discussed herein, as noted above, the winding modules 12 may have winding controls specific to each module 12, with a common machine control. Real time changes may be made where different types of rolled products 22 are produced without having to significantly modify or stop the rewinder 10. Real time roll attributes can be measured and controlled, and in some embodiments, operation is not limited to the cycle rate.

A winder may be capable of producing a wide spectrum of rolled products 22, and is not limited towards a specific width of the web 36. Also, the plurality of independent winding modules 12 can be designed in such a way that maintenance may be performed on any one or more of the winding modules 1-6 without having to interrupt operation, as previously discussed with winding module 6. A winding module 12 may be removed and worked on while the rest keep running. Further, having a plurality of independent winding modules 12 allows for an increase in the time intervals available for the core 24 loading functions and the rolled product 22 stripping functions.

For example, as will be discussed below, the time intervals may be increased by implementing the core loading and rolled product stripping functions as timed operations that are not synchronized to a master count value. Allowing for an increase in these time intervals greatly reduces the occurrence of loading and stripping errors. Also, prior art apparatuses experiencing interruption of the winding operation will oftentimes produce a rolled product 22 that is not complete. This waste along with the waste created by the changing of a parent roll or product format change will be reduced as a result of the rewinder 10 using asynchronous control principles. Waste may be removed from the rewinder 10 by use of a waste removal apparatus 200 (FIG. 5) as is known in the art.

Figure 3:
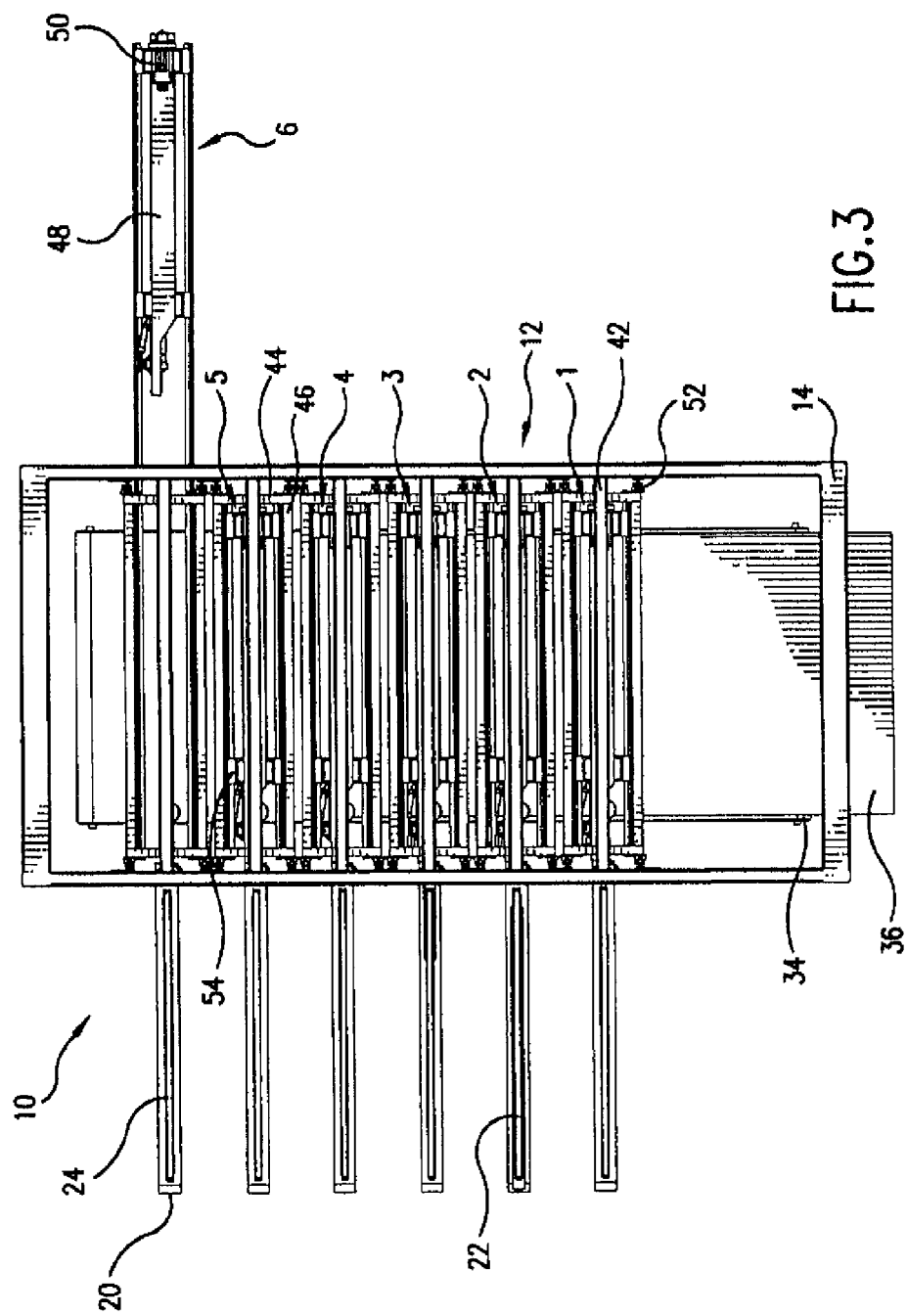
FIG. 3 is a plan view of an exemplary embodiment of a winder. The drawing shows a plurality of independent winding modules linearly situated with respect to one another and performing the various functions of a log winding cycle.

FIG. 3 shows a rewinder 10 having a frame 14 disposed about a plurality of independent winding modules 12. The positioning apparatus 56 that communicates with the winding modules 1-6 is engaged on one end to the cross members 42, as shown in FIG. 4. A vertical linear support member 44 is present on the plurality of independent winding modules 12 in order to provide an attachment mechanism for the positioning apparatus 56 and to provide for stability of the winding modules. The positioning apparatus 56 may be a driven roller screw actuator. However, other means of positioning the plurality of independent winding modules 12 may be utilized. A horizontal linear support member 46 is also present in the plurality of independent winding modules 12. The horizontal linear support member 46 may communicate with a horizontal linear slide 54 (as shown in FIG. 6) to allow some or all of the plurality of independent winding modules 12 to be moved outside of the frame 14.

Figure 6:
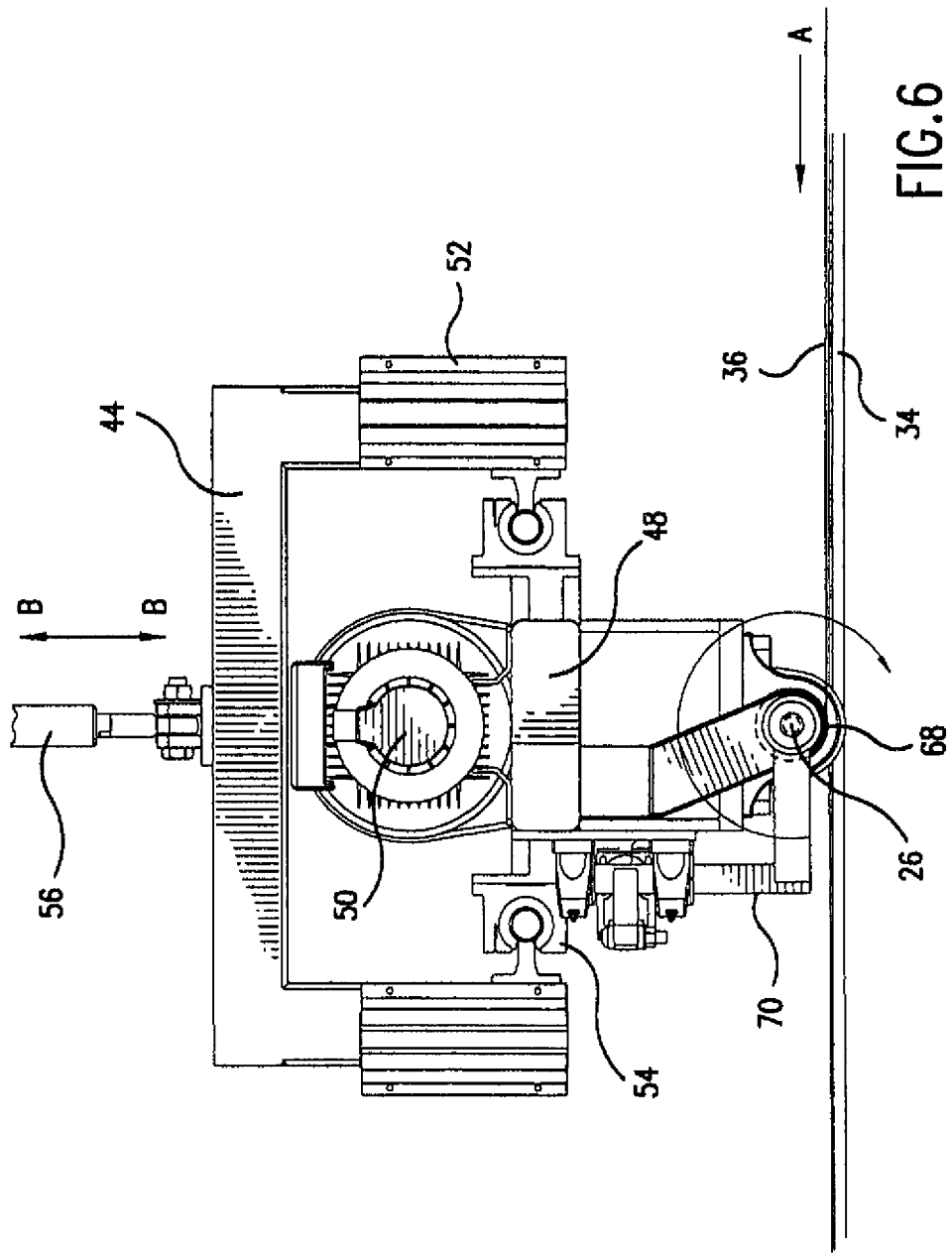
FIG. 6 is a side elevation view of an exemplary embodiment of an independent winding module. The drawing shows the winding module engaging a web and forming a rolled product via center and surface winding.
Figure 7:
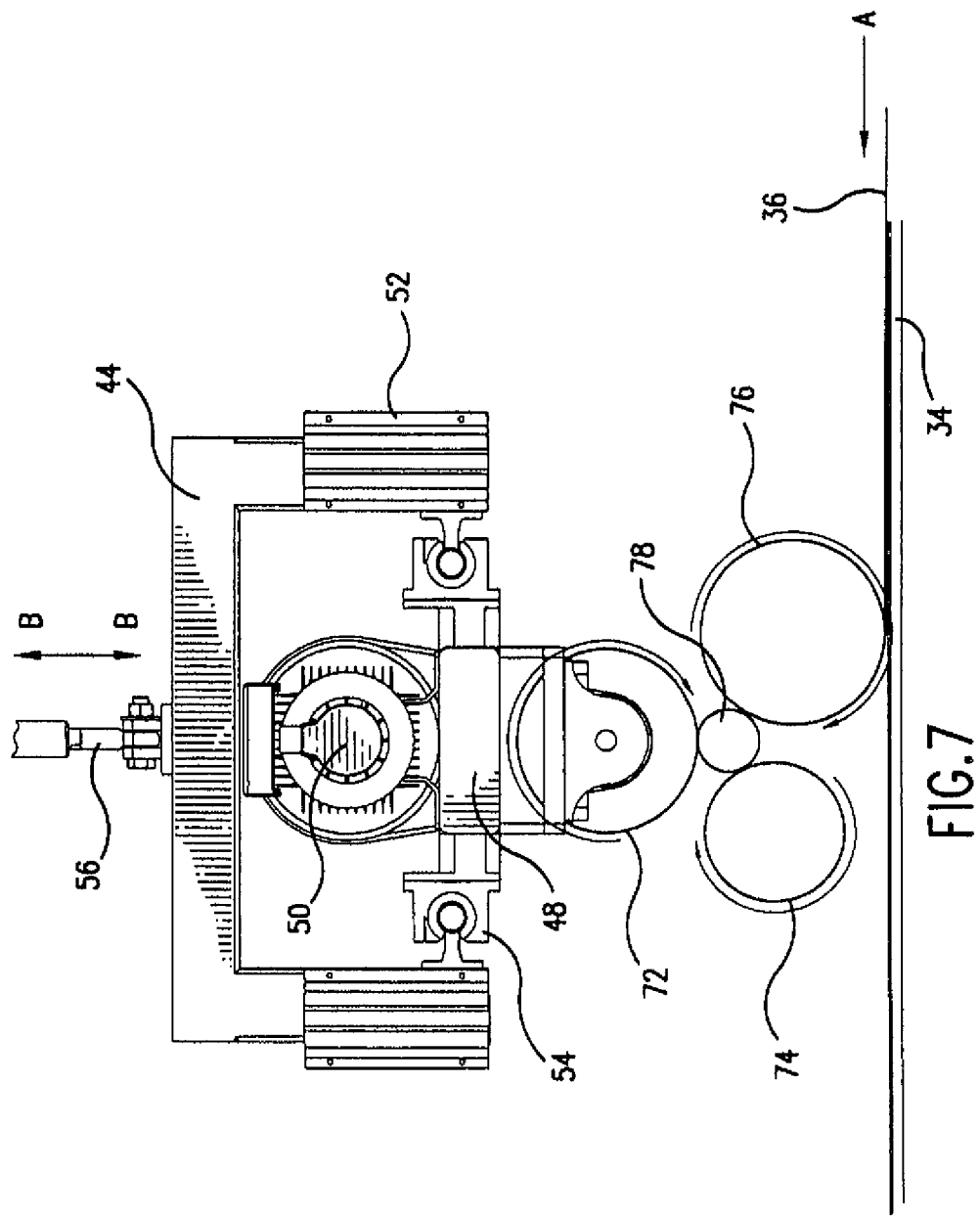
FIG. 7 is a side elevation view of an exemplary embodiment of a winding module. The drawing shows the winding module using rolls to form a rolled product via surface winding only.

FIG. 6 shows a close up view of an exemplary embodiment of a winding module. The servomotor 50 can be supported by the module frame 48 onto which a mandrel cupping arm 70 is configured. As can be seen, the positioning apparatus 56 may move the winding module for engagement onto the web 36 as the web 36 is transported by the web transport apparatus 34. Doing so will produce a nip 68 at the point of contact between the mandrel 26 and the transport apparatus 34, with the web 36 thereafter being wound onto the mandrel 26 to produce a rolled product 22.

It will be understood that each module can have a different physical configuration and may wind using different principles. For instance, in the same machine, one module may comprise a surface winder, another module may use core winding, and another module may use a vacuum mandrel. Additionally, production of a rolled product 22 having a core 24 or a coreless cavity in the rolled product 22 can be achieved in any other suitable fashion.

The plurality of winding modules 12 may also be modified such that additional improvements are realized. For instance, a tail sealing apparatus 30 may be included on the plurality of independent winding modules 12. As shown in FIG. 2, the tail sealing apparatus 30 is located on the underside of the plate 48. The tail sealing apparatus 30 may be a series of holes from which an adhesive is sprayed onto the rolled product 22 as the final lengths of the web 36 are wound onto the rolled product 22. The adhesive causes the tailing end of the web 36 to be adhered to the rolled product 22. It is therefore possible to seal the tail of the rolled product 22 before being unloaded to the rolled product transport apparatus 20. Of course, it may also be possible to provide adhesive to the web 36 at a point other than at the plurality of independent winding modules 12. As stated, for example, adhesive may be applied by the tail sealing module 62 as shown in FIG. 5. Also, it may also be the case that sealing of the tail of the web 36 onto the rolled product 22 may be done offline, beyond the winder.

In order to get the web 36 onto the mandrel 26, the mandrel 26 as shown in FIG. 6, may be a vacuum supplied mandrel. Such a vacuum mandrel 26 will pull the web 36 onto the mandrel 26 by means of a vacuum supplied through all or parts of the vacuum mandrel 26. Other ways of assisting the transfer of the web 36 onto the mandrel 26 are also possible. For instance, an air blast may be provided under the surface of the web transport apparatus 34 or a camming apparatus may be placed under the web transport apparatus 34 to propel the web 36 into contact with the mandrel 26. Further, the positioning apparatus 56 may be used to push the winding module down onto the web 36 to effect the winding. Again, the rewinder 10 is thus capable of producing a rolled product 22 which has a core, which is solid without a core or cavity therethrough, or which does not have a core but does have a cavity therethrough. Such a rolled product 22 that is produced without a core 24, yet having a cavity therethrough could be produced by using a vacuum supplied mandrel 26.

FIG. 5 shows an exemplary embodiment of a rewinder 10 that makes use of several modules upstream from the plurality of independent winding modules 12. For instance, a cut-off module 60 is utilized that severs the web 36 once a desired amount of web 36 is transported for the production of a rolled product 22. This severing creates a new leading edge for the next available winding module 1-6 to engage. However, it is to be understood that a cut-off module 60 may be utilized at locations immediately adjacent to or at the nip 68 of the plurality of independent winding modules 12. Also, FIG. 5 shows an adhesive application module 62 on the web transport apparatus 34 for applying adhesive or an adhesive tape onto the web 36. A perforation module 64 is also provided in order to perforate the web 36.

One particular embodiment of a cut-off module 60 that is particularly well suited to breaking the web 36 while moving is shown in FIG. 15. In particular, the cut-off module 60 as illustrated in FIG. 15 can form a break in the web 36 without having to stop or decelerate the web during the winding process.

As shown, the cut-off module 60 includes a rotating roll 300, such as a vacuum roll that rotates with the web 36 and defines a conveying surface 302. In this embodiment, the vacuum roll 300 is placed adjacent to a guide roll 304 which can receive the web 36 from a parent roll or directly from a papermaking process. Not shown is a perforation module 64. The web 36, however, can be perforated as it is unwound or can be pre-perforated Also shown in FIG. 5 is a waste removal apparatus 200 for removing extra web 36 that results from faults such, as web breaks, and machine start ups. This waste is moved to the end of the web transfer apparatus 34 and then removed. The asynchronous control of a plurality of individual modules 12 reduces the amount of waste because once a fault is detected, the affected module 12 can be shut down before the rolled product is completely wound. The web may then be severed on the fly and a new leading edge transferred to the next available module. Any waste is moved to the end of the web transfer apparatus 34 and then removed.

As was noted above, through use of asynchronous control, each of the winder modules 1-6 of the plurality of independent winding modules 12 do not rely on the successful operation of any of the other modules 1-6. This allows the rewinder 10 to operate whenever commonly occurring problems during the winding process arise. Such problems could include for instance web breaks, ballooned rolls, missed transfers, and core loading errors. The rewinder 10 therefore will not have to shut down whenever one or more of these problems occurs because the winding modules 1-6 can be programmed to sense a problem and work around the particular problem without shutting down. For instance, if a web break problem occurs, the rewinder 10 may perform a web cut by a cut-off module 60 and then initiate a new transfer sequence in order to start a new winding about the next available winding module 1-6.

For example, the module that is winding when the web breaks can discontinue operation, either due to its own detection of a fault or in response to a command from a machine central controller. Simultaneously or shortly thereafter, the machine central controller can determine the next available point of engagement for the web based on the timing of the web cut and known data regarding the minimum lead time (expressed as count values) for a "ready" module to engage the web. A ready module could be commanded to engage its virtual master at an appropriate system master count so as to begin operation at the newly-cut edge. Depending on the lead time, the web may be cut again to provide a leading edge to be engaged by the winding module. Of course, in other embodiments, the module could engage the web at a point other than an edge, depending on the type of winding that is used.

Any portion of the web 36 that was not wound would travel to the end of the web transport apparatus 34 where a waste removal apparatus 200 could be used to remove and transport the waste to a location remote from the rewinder 10. The waste removal apparatus 200 could be for instance an air conveying system. The winding module 1-6 whose winding cycle was interrupted due to the web break could then be positioned accordingly and initiate removal of the improperly formed rolled product 22. Subsequently, the winding module 1-6 could resume normal operation. During this entire time, the rewinder 10 would not have to shut down. Instead, the operational sequence could be modified to proceed without the faulted module. Once the fault is cleared, the module could be returned to "ready" status and then included in the operational sequence at any suitable point (if needed).

Another exemplary embodiment of winding involves the use of a slit web. Here, the web 36 is cut one or more times in the machine direction and each slit section is routed to a plurality of winding modules 12. It is therefore possible to wind the web 36 by two or more modules 12 at the same time.

In some embodiments, the winding process can be performed at an end of a tissue machine. In this way, the tissue web 36 could be directly converted to product sized rolls 22 which in turn would bypass the need to first wind a parent roll during the manufacturing and subsequent rewinding process.

The plurality of independent winding modules 12 of FIG. 5 are arranged in a substantially linear direction. In addition, the web transport apparatus 34 is also linear in orientation at the location proximate to the plurality of independent winding modules 12. The embodiments depicted are of an orientation of the web transport device in a substantially horizontal plane. However, it should be realized that any orientation other than horizontal could be utilized. Furthermore, the embodiments depicted utilize modules that only engage one side of the web transport apparatus. It should be understood that a winder could be configured where the winding modules engage more than one side of the web transport apparatus.

Figure 8:
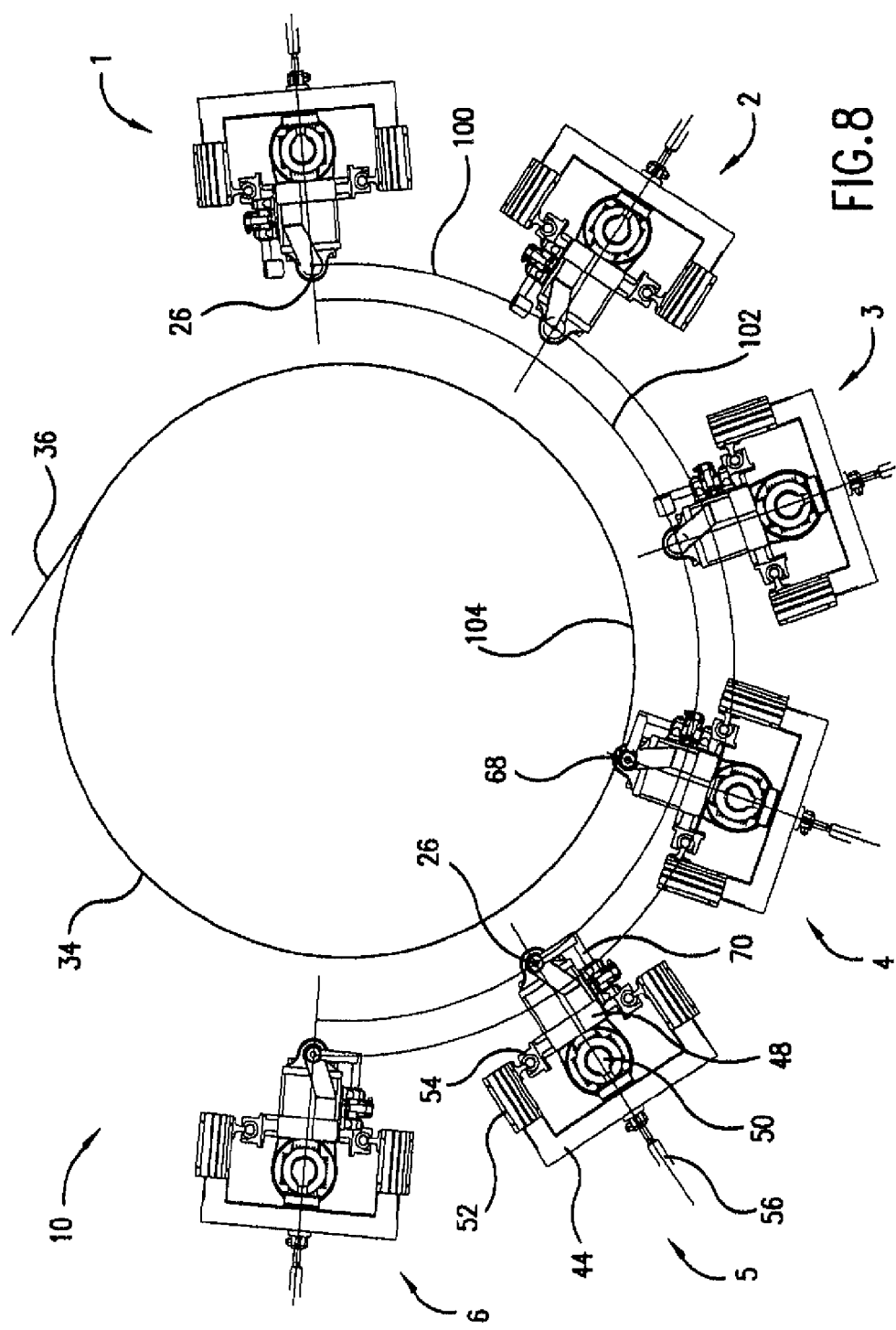
FIG. 8 is a side elevation of an exemplary embodiment of a winder. The drawing shows a plurality of independent winding modules being radially situated with respect to one another and interacting with a circular web transport apparatus.

FIG. 8 shows an alternative configuration of both the web transport apparatus 34 and the plurality of independent winding modules 12. The exemplary embodiment shown in FIG. 8 is a plurality of winding modules 12 that are radially disposed with respect to one another, and a web transport apparatus 34 that is cylindrical in shape. The web transport apparatus 34 in this case can be, for instance, a vacuum roll. Each of the winding modules 1-6 are arranged about the web transport apparatus 34 such that the winding modules 1-6 are moved towards and away from the web transport apparatus 34 by the positioning apparatus 56.

Figure 9:
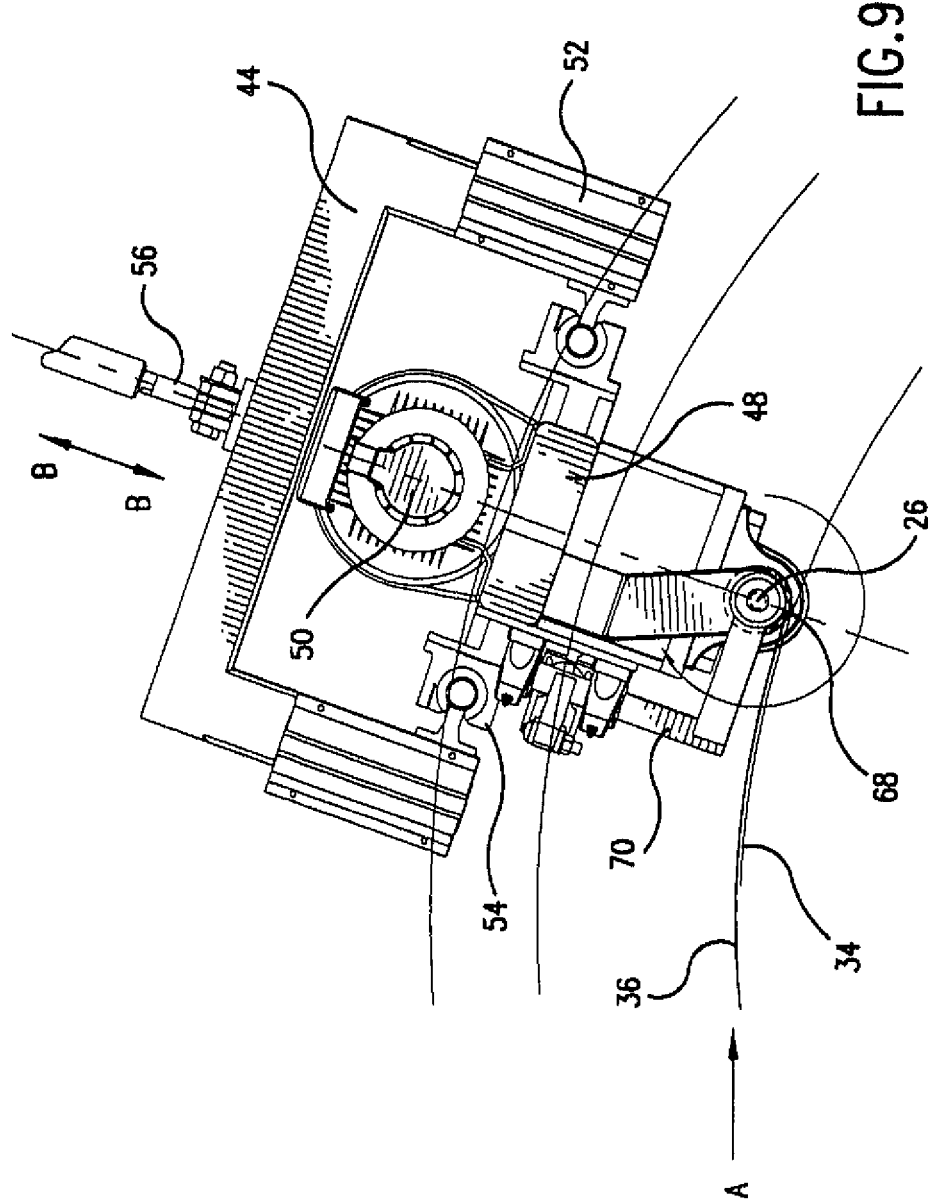
FIG. 9 is a side elevation view of an exemplary embodiment of an independent winding module. The drawing shows a winding module that interacts with a circular web transport apparatus.

FIG. 9 discloses an exemplary embodiment of a winding module that is used in the configuration disclosed in FIG. 8. The winding module of FIG. 9 is substantially the same as the winding module shown in FIG. 6, although configured for a circular array configuration as opposed to a linear array configuration.

II. General Principles of Asynchronous Control

As was discussed above, a winder/rewinder can comprise a plurality of independent modules. Winding (and other) controls may be configured specifically for each module in a manner so that modules do not necessarily rely on successful operation of other modules. In some embodiments, this may be achieved through use of a distributed control system that allows for asynchronous control of the various modules in the system. Although some of the following examples discussed later below relate to a modular winder/rewinder, it will be appreciated that the control principles may be applicable to any type of machine or tool comprising a plurality of modules configurable for independent operation.

Figure 25:
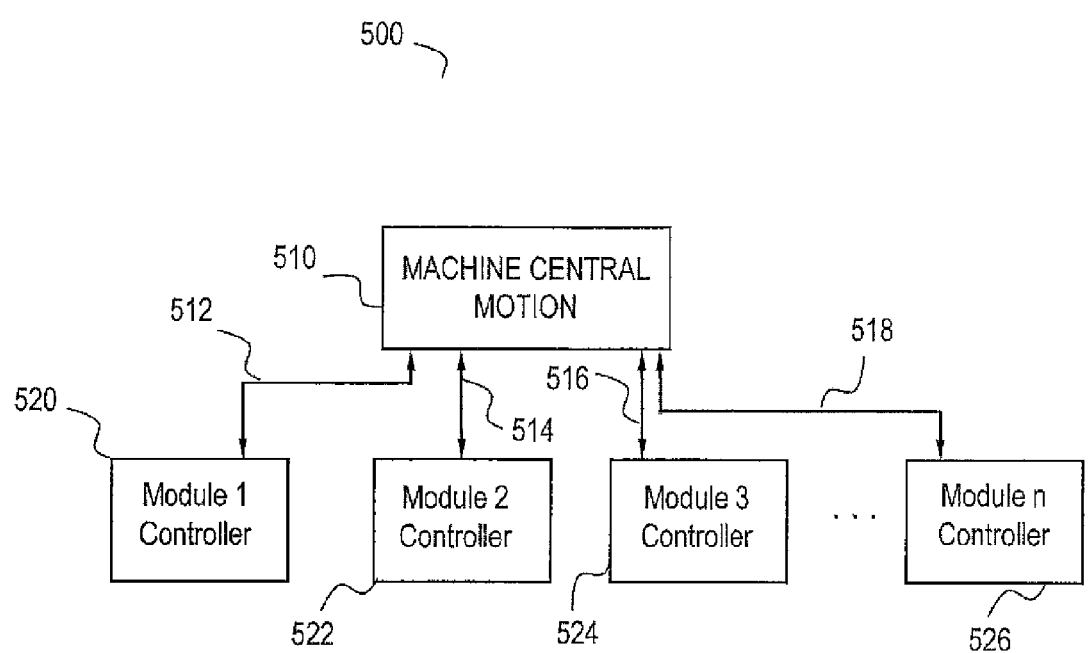
FIG. 25 is a block diagram illustrating an exemplary hardware architecture for implementing an asynchronous control system.

FIG. 25 is a block diagram illustrating an exemplary hardware architecture 500 for implementing an asynchronous control system. Machine central motion controller 510 is linked to controllers for various modules comprising the machine. In this example, machine central motion controller 510 is linked to module 1 controller 520, module 2 controller 522, module 3 controller 524, and module n controller 526. Although four module controllers are shown in FIG. 25, it will be understood that more or fewer module controllers can be used depending on the particular machine and control system implementation. For example, in a machine comprising six winding modules 12, the hardware architecture could comprise six respective winding module controllers, along with one or more other module controllers for cut-off, adhesive application, and perforation. Returning to the example of FIG. 25, machine central motion controller 510 and module controllers 520, 522, 524, and 526 may each comprise any suitable type or arrangement of computing devices, such as general-purpose computers, specialized microprocessor-based hardware controllers, and the like. In some embodiments, some or all of aspects of the module controllers and/or central motion controller may be implemented as separate logical units using the same computing device or devices. Some aspects of the control system may be implemented by software or specialized hardware (such as application-specific integrated circuits).

Generally speaking, connections 512, 514, 516, and 518 may comprise any suitable type or combination of types of data connections. For instance, the connections may comprise Ethernet connections, control net connections, and/or any other suitable connection types. Furthermore, in this example, individual links are shown between central motion controller 510 and each module. However, in other embodiments, the modules and central motion controller 510 are connected to a network and/or to one another via peer connections.

In operation, machine central motion controller 510 sends commands and inquiries to the various module controllers to implement a sequence of operation for the machine and receives status data from the modules. For example, if the various module controllers correspond to parts of a winder/rewinder, then central motion controller 510 can send commands to winding and cutting modules to cut material and carry out winding operations. If one or more modules provide a message indicating a fault, machine central motion controller 510 can adjust operation of the machine to address the fault and attempt to continue operation.

Regardless of the underlying hardware architecture, machine control can be distributed for asynchronous operation by using at least a system master and one sub-system virtual master, with at least some machine components synchronized to the sub-system virtual master. For instance, in some embodiments, a control system for a modular machine can provide, produce, or otherwise generate a system virtual master and at least one module virtual master, with module components synchronized directly or indirectly to the module virtual master. Machine central motion controller 510 can provide a signal representing the system virtual master and commands to one or more module controllers. Central motion controller 510 can access one or more control programs that define one or more sequences of operation. Based on the sequences of operation, central motion controller can calculate required timings and send commands to the module controller(s) to properly synchronize the module virtual master(s) to respective given points on the system virtual master to implement the desired operations. Moreover, the given point for each module can change between system virtual master operational cycles while the other portions of the machine or system remain in motion.

Figure 26:
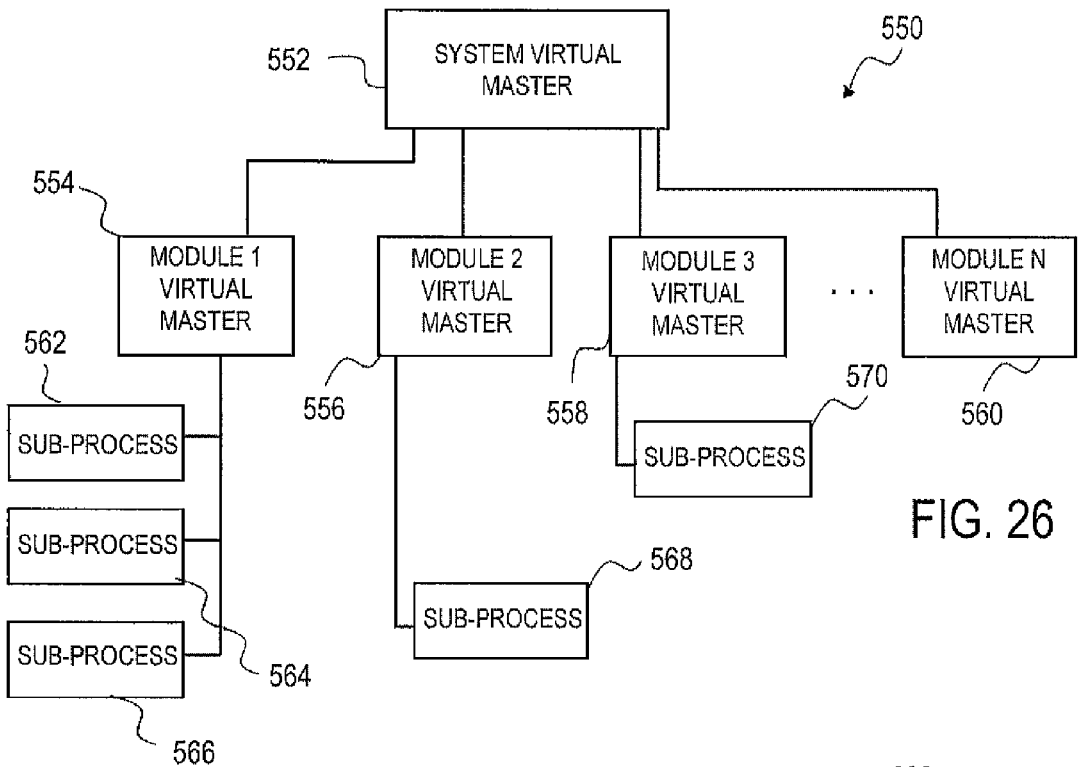
FIG. 26 is a block diagram of the overall control system architecture of an exemplary, generalized, embodiment of a distributed asynchronous control system.

FIG. 26 illustrates a block diagram of the overall control system architecture of an exemplary embodiment of a distributed asynchronous control system for components of, for example, a machine, in a generalized form. Block 552 represents the system master. For instance, block 552 may represent a system virtual master or system master signal provided by a central motion controller. Alternatively, in some embodiments, the system master may comprise a master signal, such as an encoder generated based on a physical master axis. The control system further comprises additional virtual masters 554, 556, 558, and 560 each corresponding to a respective module 1, 2, 3, and n. For instance, the module virtual master signals may be provided by respective module controllers.

Although four virtual masters corresponding to four modules are explicitly identified and discussed, the reference to module n is meant to indicate that the control system may comprise many more modules and the present subject matter is not intended to be limited by the number of modules. Of course, a control system could comprise fewer modules, as well. Additionally, in some embodiments, a module may comprise components that are synchronized to one or more sub-process virtual masters, with each sub-process virtual master synchronized to the module virtual master.

As was noted above, some machine components may be synchronized to the system master directly in a conventional manner. However, such components (for example, a machine conveyor) are not addressed in detail herein.

Each module can comprise components used in one or more sub-systems/sub-processes, and each module may be configured to perform one or more actions, steps, or other activities involved in the task(s) and/or function(s) performed by the machine. Module controllers may provide one or more signals or indicators that cause the components to perform as desired, such as by sending electrical, hydraulic, or other signals.

A generalized arrangement of sub-processes carried out by a machine are shown in FIG. 26 as sub-processes 562, 564, 566, which are associated with module 1, sub-process 568, which is associated with module 2, and at sub process 570 which is associated with module 3. For example, as noted above, a winder/re-winder may comprise modules configured to perform tasks including loading cores, positioning a mandrel, winding a roll, removing the finished log, and cutting material in anticipation of another winding operation. As another example, a robotic assembly system may be configured so that the system positions components, fastens the components together, and then paints the assembly. Each task could be handled by a different module and could comprise a number of sub-processes. Generally speaking, the particular organization of tasks and functions may vary according to particular circumstances of a machine, depending on factors such as the purpose of the machine, materials produced by/operated on by the machine, the machine location, intensity of use, and other factors. As will be discussed below, in some embodiments, a sub-process carried out by a module may be implemented by components coordinated by a virtual master devoted to the sub-process. The sub-process virtual master may be synchronized to the module virtual master at an appropriate time.

The modules may be configured to perform tasks in any suitable manner. For example, in some embodiments, sub-processes may be carried out by providing physical motion to one or more machine components through the use of servo and other controls with electronic cam profile capability. A cam profile can be defined and motion imparted through the use of servo motors, actuators, and the like, so that the motion of the machine component(s) follows the cam profile. For instance, positioning apparatus 56 of the examples above may control the vertical position of a mandrel or other component based on a cam profile defined for a winding operation. As another example, a group of servos and corresponding cam profiles may control the position and motion of a robotic arm while another group of servos and corresponding cam profiles direct the operation of a component, such as a paint nozzle, handled by the arm. In some embodiments, the cam profile can be calculated based on other data specifying the desired motion, which may advantageously allow for re-definition of cam profiles by specifying alternative data, such as alternative profiles for different tasks or variations on tasks.

Alternatively or additionally to changing cam profiles, component motion may be varied in other ways, as well. For instance, as will be discussed later below, motion can be adjusted during an operation based on feedback such as sensor data and/or user input by varying the rate of one or more sub-system virtual master counts. As an example, during a winding operation, a roll may be biased while winding is in progress in order to account for variations in material thickness and other properties.

Generally speaking, when utilizing presently-known methods (i.e. "synchronous control"), the components of the system responsible for performing different tasks are slaved to a virtual or real master axis or encoder. For instance, a first process could operate on a material, followed by a second process, and then a third process. The positioning of the components for each process are dependent upon cam profiles of the master axis. For example, the first process can begin at a first time/position on the master axis, followed by the second process at a second time/position, and then by the third process at a third time/position. However, numerous problems could develop in the event of a fault or error. For example, if a fault were to occur during the second process, then the entire machine would likely need to be stopped to clear the fault. Furthermore, if all three processes were physically synchronized to the master axis, then the machine could not successfully begin operation until it had cycled through to the beginning of the first process. In systems using a virtual master axis and electronic cams, rather than running the virtual master to reset the components, the master could be reset. However, the machine would still have to be stopped in order to reset the virtual master axis to the initial position, since otherwise the machine could be damaged were the virtual master to be reset while the machine was in motion.

FIG. 28 illustrates several exemplary hypothetical timing diagrams for a machine. The time scale is arbitrary, and the designations of time are included for relative reference and example only. The horizontal axis is represented as "t" and time values are discussed; however, a control system may be implemented on the basis of count values rather than time values, which are used here for convenience. In these examples, generalized sub-processes carried out by the machine are associated with three different modules. For example, module 1 may comprise components that perform preliminary operations on a material, module 2 may comprise components that perform finishing operations, while module 3 comprises components that clean up waste and prepares new material for manipulation by module 1.

Figure 28A:
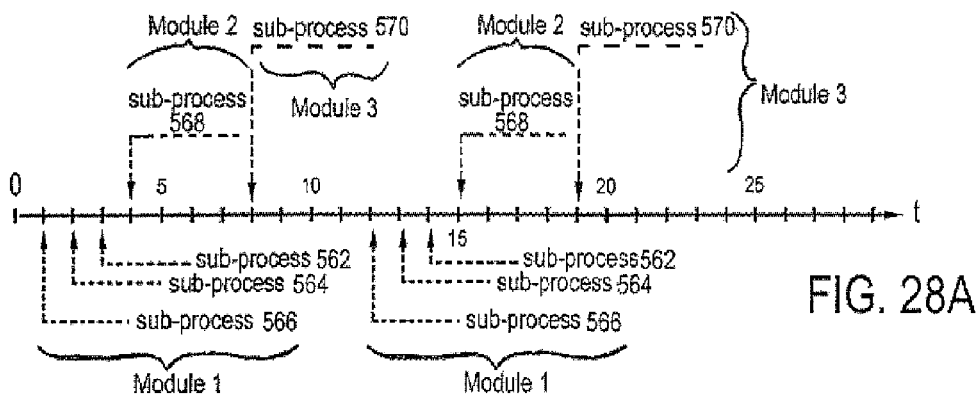
FIGS. 28A-28C illustrate several exemplary hypothetical timing diagrams for a generalized machine.

FIG. 28A illustrates the ideal operation of the machine. At t=1, the components comprising module 1 engage in sequence, namely performing sub-process 566 at t=1, sub-process 564 at t=2, and sub-process 562 at t=3. Next, the components of module 2 engage at t=4 to carry out sub-process 568 at t=4 after the sub-processes of module 1 are complete. At t=8, sub-process 570 is carried out by engaging the components comprising module 3. At t=12, the components of module 1 are again engaged and the machine begins another operational cycle.

Figure 28B:
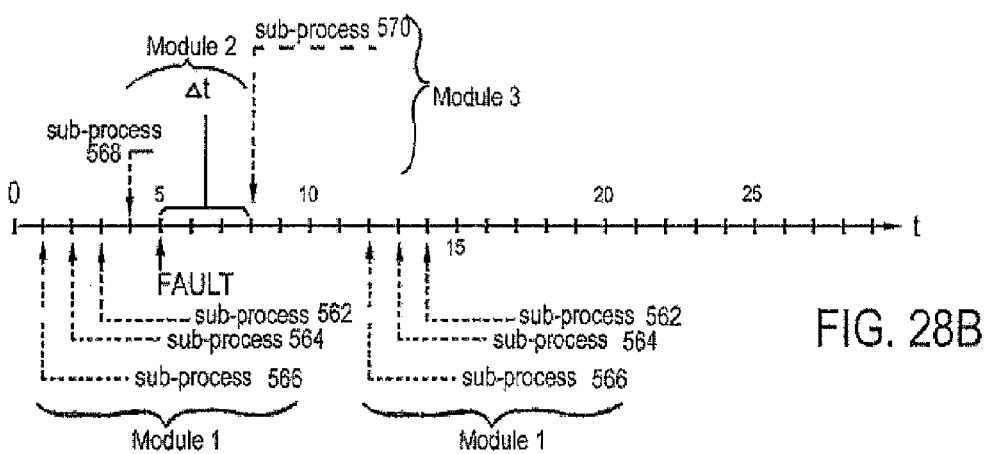

FIG. 28B illustrates an example of the occurrence of a fault and handling thereof in a system using conventional "synchronous control." At t=1, the components of module 1 are engaged and operate properly in sequence, with the components of module 2 engaged at t=4. However, in this example, a fault occurs at t=5. For example, module 2 may fail to perform the finishing operations due to a hardware failure. If the modules are operating on a material in sequence, then the partially-processed material may need to be discarded and the process re-initialized by clearing the material using module 3 (or otherwise cleared). Then, the machine operation will need to be re-started with module 1, likely involving re-homing of the machine. However, if the components of the machine are synchronized to a system (virtual) master, then the process may not begin anew in a timely manner and significant waste may be generated in the interim.

First, the machine may need to be stopped to clear the fault in module 2. Even if the machine is constructed with replaceable modules, a machine with a synchronized control system cannot "drop" a new module into the sequence without resetting the virtual master, which entails stopping the machine as noted above to avoid damage. If the machine is operating on a material moving through the machine at a high speed, starting and stopping the machine may result in appreciable amounts of waste as material moves through the machine during the startup and shutdown sequence. Even if the fault is cleared while avoiding stopping the machine, though, since the components of module 3 are synchronized to the system virtual master in this example, then module 3 will not engage until t=8, resulting in a delay of At=3. An operational delay of t=3 could result in extensive waste as material continues through the machine unprocessed or processed improperly. Additionally, time and energy are wasted while running the machine without producing the desired output.

In embodiments of the present subject matter, however, at least some of the sub-processes are not directly synchronized to the system virtual master. Instead, the system virtual master is used as a timing base for coordinating the operation of at least some of the machine components via one or more other sub-system virtual masters selectively synchronized to the system virtual master. One or more modules may comprise the components, with the one or more modules each having its own virtual master. Each module virtual master may be locked-in to the system virtual master when needed and as directed, with the sub-processes for each module timed relative to the module virtual master and not the system virtual master. Thus, the sub-processes of each module are not directly synchronized to the system virtual master, and so the components of the machine can be controlled "asynchronously." Additionally, as will be discussed below, the time involved in re-calculation of cam profiles may be advantageously reduced since the cam profiles will depend on the module virtual master rather than the system virtual master. Furthermore, some components can be operated completely independently of any master count value in some embodiments.

Figure 28C:
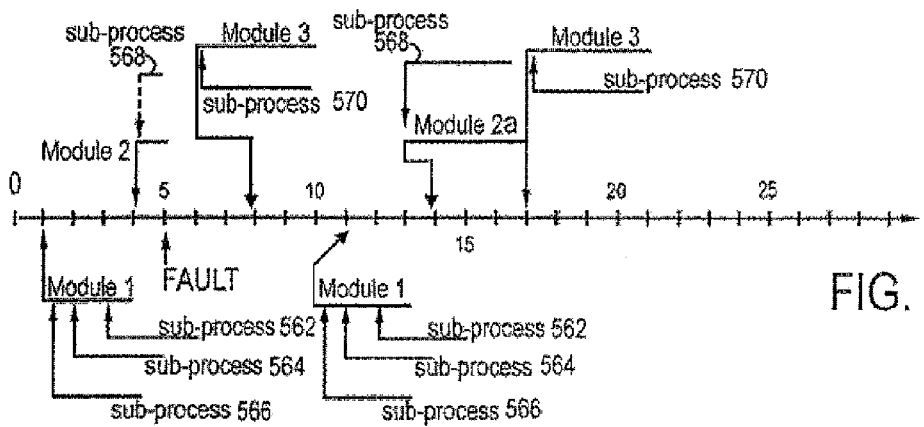

FIG. 28C illustrates the fault scenario of FIG. 28B, but in this example, the machine is configured so that the module sub-processes are synchronized to module virtual masters. For instance, sub-processes 566, 564, and 562 engage at t=0, 1, and 2 relative to the timing of module 1 virtual master. The respective sub-processes comprising modules 2 and 3 engage at t=0 relative to their respective module virtual masters. In this example, the module 1 virtual master is instructed to synchronize with the system virtual master at t=1. Thus, the first time the sub-processes of module 1 are executed, the sub-processes engage at the same times relative to the system virtual master as in the examples above. For example, since sub-process 564 is set to engage at t=1 relative to module 1 virtual master, and t=0 of module virtual master corresponds to t=1 of the system virtual master, then sub-process 564 will engage at t=2 relative to the system virtual master. Similarly, the module 2 virtual master is synchronized to the system virtual master at t=4 and the module 3 virtual master is initially planned to be synchronized to the system virtual master at, for instance, t=8.

As in the example of FIG. 28B, however, the components of module 2 develop a fault at t=5. In this example, though, the asynchronous distributed control configuration allows for the machine to continue operation.

First, module 3 is instructed to lock on to the system virtual master at t=8 or as soon as possible after the fault, such as at t=6. For instance, a machine central motion controller may receive a fault indication from module 2 and, as part of a control program, determine that module 3 is to be brought into operation as soon as possible to clear the fault. Module 3 may need some time before it can be brought into operation though. For example, module 3 may require time to be positioned and/or brought up to operating speed. Based on the operating speed of the machine, the known preparation time for module 3, and/or other parameters, central motion controller may determine that module 3 can be brought into operation at t=8 and therefore the central motion controller can send appropriate commands to module 3 to lock on at that time. Additionally, the central motion controller may attempt to clear module 2 from the machine, for example, by commanding module 2 to return to an inactive or offline position.

Furthermore, the machine central motion controller can adjust the timing for other operations. For example, module 1 is directed to lock on to the system virtual master at t=10 (rather than at t=12 as originally planned) so that its operations begin as soon as module 3 has completed operation. This can represent a substantial improvement in machine operation. For instance, if the components of module 1 were directly synchronized to the system virtual master, then each individual component would need to be re-synchronized. For example, cams corresponding to sub-processes 562, 564, and 566 would each need to be re-calculated so their respective components would be positioned to "begin" at t=10, 11, and 12, respectively, rather than at t=12, 13, and 14. However, since the sub-processes are synchronized to the module 1 virtual master, no re-calculation is required. Instead, the module 1 virtual master is directed to start at a different time based on the lock-on commands received from the machine central motion controller.

Continuing the example of FIG. 28C, a substitute module 2*a* is directed to lock on to the system virtual master at t=13 so the machine can continue operation while the fault in module 2 is investigated and cleared. For instance, the machine may comprise a plurality of modules capable of performing the sub-process 568 of module 2. Once module 2's fault condition is confirmed, machine central motion controller 10 may access data indicating which (if any) modules equivalent to module 2 have provided a "ready" signal. Assuming module 2*a* is an equivalent module and has provided a "ready" signal (for example, after having earlier completed an operational sequence), module 2*a* can be selected and directed to synchronize to the system virtual master at t=13.

In the above generalized examples, the particular aspects of the control sequences were presented in a simplified manner. For instance, when implementing the sub-processes and virtual masters, it may be preferable to configure sub-process timing and/or subsystem virtual master counts to avoid mechanical stresses involved in sudden starts/stops of components. For example, sub-processes of a module may be timed to module virtual masters in a manner to avoid engaging the sub-processes instantaneously when the virtual master begins, such as by avoiding commands requiring components to be at full operational speed at t=0. Exemplary ways of timing/synchronizing components and virtual masters to one another will be discussed below in conjunction with more detailed examples relating to the operation of an exemplary winder/rewinder.

III. Exemplary Aspects of Asynchronous Control Principles as Applied to a Modular Winding Machine Turning back to FIG. 27, an illustration is shown of an exemplary control architecture for a modular winder/rewinder such as discussed earlier in the present specification. System virtual master 600 provides overall process control and a timing base for the remaining components. In this example, the control system includes two module virtual masters 602*a* and 602*b*, each for a respective winding module. In this example, each winding module further comprises virtual masters for mandrel rotation (604*a* and 604*b*), mandrel lift (608*a* and 608*b*), and log strip/core load operations (606*a*, 606*b*), respectively. The exemplary control architecture of FIG. 27 further includes a cutoff virtual master 610, although specific sub-tasks for that module are not depicted in this illustration. Depending on the machine, other virtual masters may be used, such as for additional modules that provide perforation, apply adhesives or additives, or provide other functionality. A module "n" is also depicted to indicate that the architecture can comprise one or more additional module virtual masters.

Mandrel rotation virtual masters 604*a* and 604*b* may each coordinate a number of respective components involved in winding of a roll as discussed above. For instance, the characteristics of the rolled product will depend on factors such as the winding speed, tightness of the wind, and other characteristics. The behavior of the system components responsible for regulating winding speed, tightness, and other characteristics may be controlled through specification of differing cam profiles. For example, different cam profiles can be defined for different types of desired winds and for materials with different characteristics. For example, different cams may be defined for different sheet counts or desired roll diameters. As another example, different cams may be defined for different substrates, such as a different profiles for winding textile products, steel products, plastic products, and composite products. When a module is off-line (i.e. not engaged in a winding operation), the new cam profiles can be selected in order for the module to perform differently in its next operation.

In some embodiments, a sub-system virtual master, such as mandrel rotation virtual master 604*a* (or 604*b*) can be configured to respond to feedback during a winding operation. For example, as noted above, wind characteristics can be adjusted through specifying different cam profiles. However, additional, fine-grained control can be achieved by changing the count rate for a sub-system virtual master relative to the virtual master which it is synchronized to (e.g. the system virtual master or another sub-system virtual master).

Generally speaking, a first virtual master will count from a starting value to a final value over an operational cycle. The starting and final values for the first virtual master will correspond to a first and second count for another virtual master. In some embodiments, the rate of the first virtual master count can be adjusted during the count. For example, the count may initially proceed at a first rate and then be slowed to a second rate based on feedback. Before the end of the count, the rate may be increased to a third rate in order to bring the first virtual master count back into phase with the other virtual master count. The feedback may be provided, for example, based on sensor data regarding material inputs and/or finished products, and additionally or alternatively may be based on user input during operation.

In this example, the mandrel rotation virtual master begins counting at a specified time relative to the value of the module virtual master (which is itself timed relative to the system virtual master). By varying the rate of, for instance, the mandrel rotation virtual master count, the roll velocity may be changed on-the-fly in response to data, such as thickness variations or inhomogeneities in the source roll for the material being wound. Additionally or alternatively, similar results could be achieved by varying the rate of the module virtual master count. However, changing the rate of the module virtual master count would affect all other components/virtual masters timed to the module virtual master, which may or may not be desired depending on the circumstances.

Mandrel lift virtual masters 608a and 608b each coordinate respective components related to the vertical position of the mandrels, such as positioning apparatus 56 in the exemplary modules discussed above. For instance, at the start of a wind, the mandrel can be positioned proximate to the web and then moved away from the web as the product is wound. If mandrels are placed on a web from above, then the mandrel position will start close to the web and move vertically upward; the required motion will depend, of course, on the arrangement of the machine. The characteristics of the wind will depend on factors such as the amount of resistance or nip pressure imparted by the mandrel on the wound material, which will in turn depend on its vertical position (and other factors as well). Thus, different motion profiles for the mandrel lift components may be defined for different phases of the winding operation and different desired characteristics.

Figure 27:
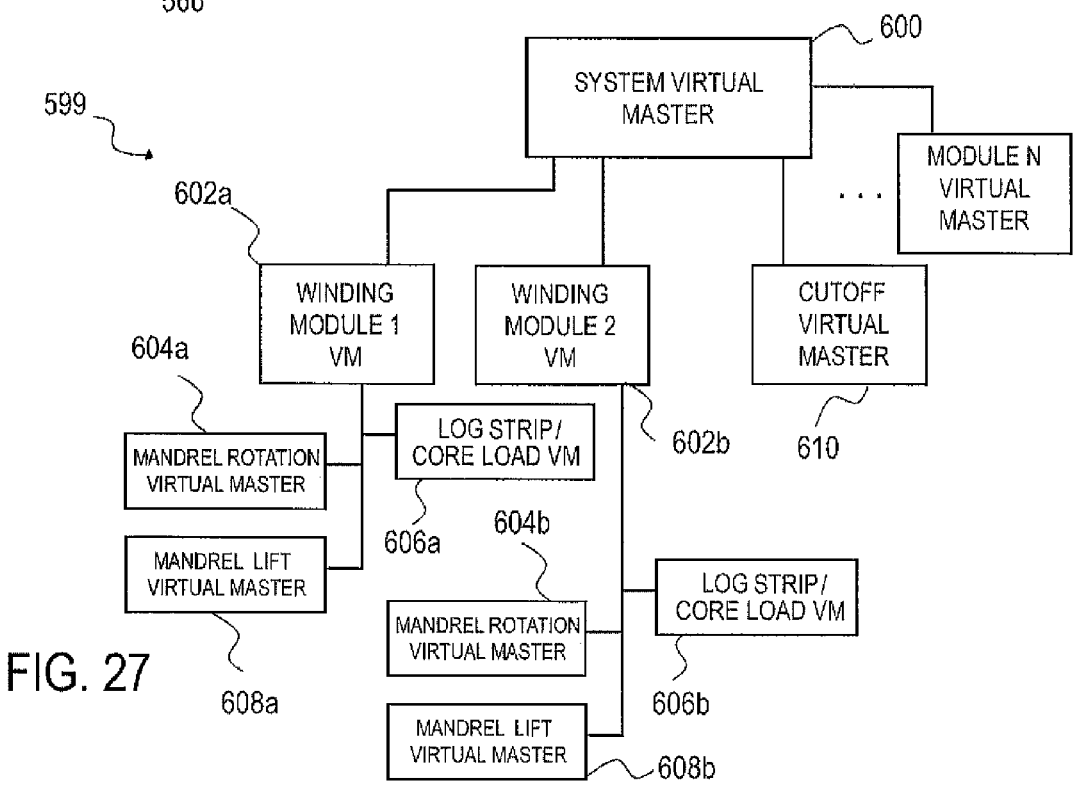
FIG. 27 is a block diagram of an exemplary control architecture for a modular winder/rewinder machine.

The cutoff virtual master 610 may provide control for one or more components used to separate the web for the beginning of a new winding operation. For example, a cutoff module may comprise components such as discussed above in conjunction with FIG. 15. However, in the following examples, an alternate embodiment, namely a cutoff bar configured to provide a pinch cut, is used for ease of explanation. Log strip/core load virtual master is also shown in FIG. 27. In some embodiments, as will be discussed below, actions such as core loading and log stripping may not be synchronized to any master counts and may, instead, rely on other signals such as the presence of a completed log or command that triggers the stripping and loading operation, which can proceed as a timed function.

Figure 29A:
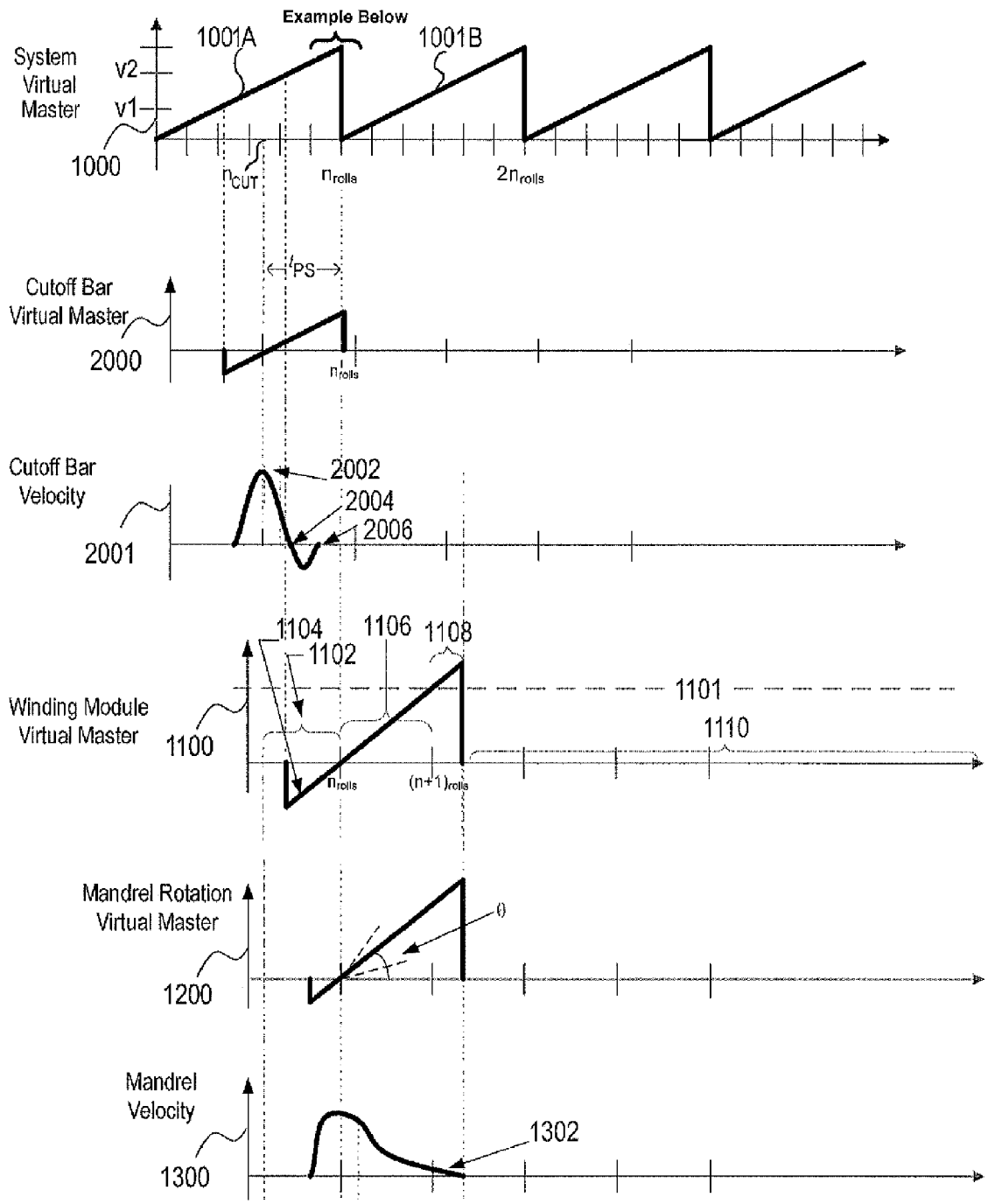
FIGS. 29A and 29B represent exemplary timing diagrams for components in an asynchronously-controlled winder/rewinder machine.
Figure 29B:
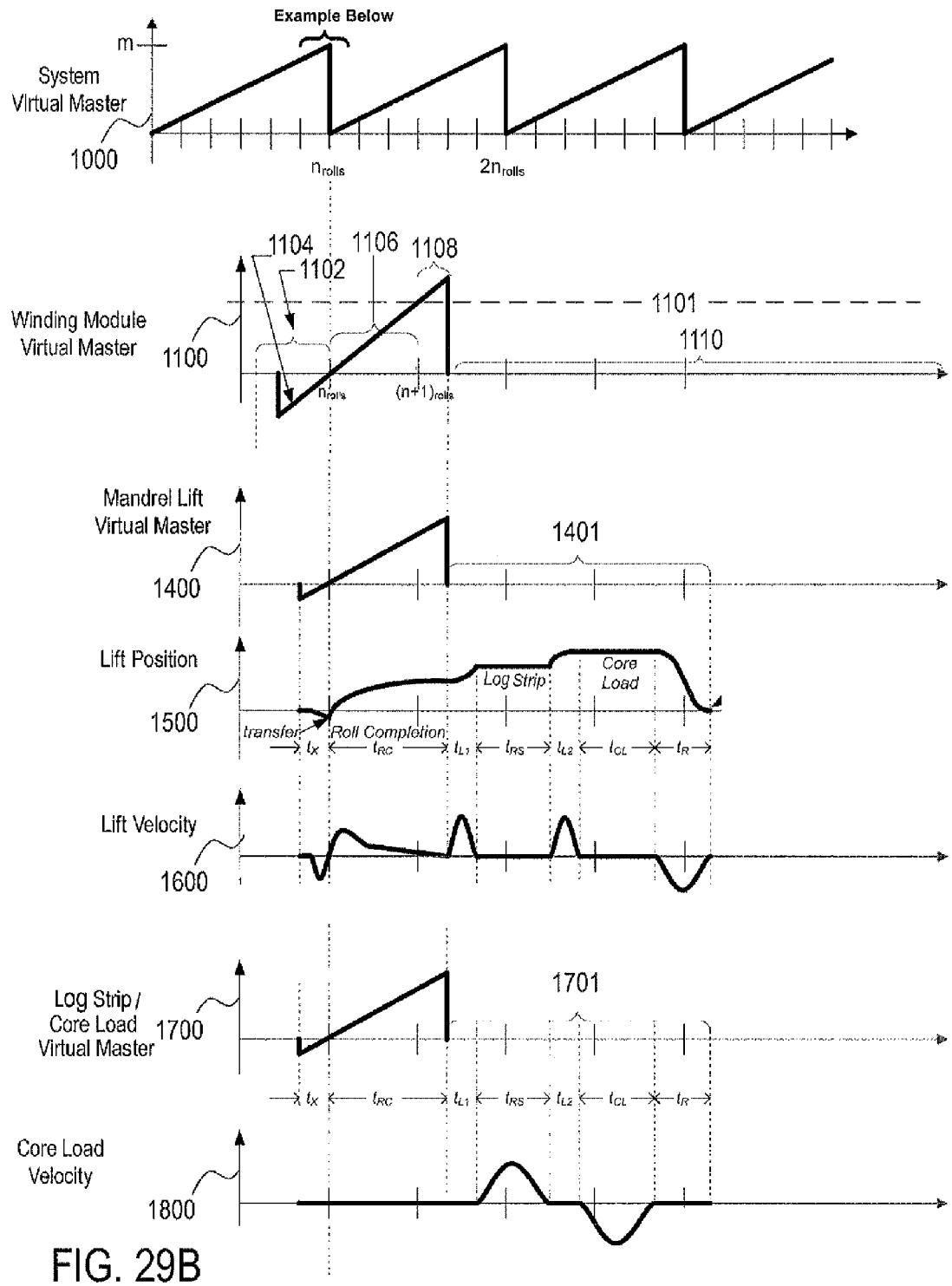

FIGS. 29A and 29B represent exemplary timing diagrams for components in an asynchronously-controlled winder/rewinder machine. The timing diagrams are not intended to present an exhaustive illustration of every component and operational scenario, but rather are hypothetical examples for use in illustrating the principles of the present subject matter. The horizontal axis generally represents time (per run speed), while the vertical axis for each graph is discussed in turn below.

Diagram 1000 illustrates an example of a system virtual master which may be generated by a control system in a machine configured for asynchronous control in accordance with the present subject matter. For example, the system virtual master may be generated by a machine central controller, either as an independent signal or based on the position of a master axis in the machine. As was noted above, the horizontal axis of diagram 1000 represents arbitrary units of time per run speed, since the present principles may be applied regardless of the speed of operation. The vertical axis represents the count value for the system virtual master illustrated generally as "m."

In operation, modules can be directed to operate in any suitable sequence by defining synchronization points which are based on the value of the virtual master. For instance, the count value of the virtual master can be selected to reach "m" at a time of $t=n_{rolls}$ on the horizontal axis. $n_{rolls}$ can define the end of a completed winding operational cycle 1001a wherein "n" rolls have been completed as well as defining the beginning of the next cycle 1001b. The number of modules and rolls used in an operational cycle will depend on the capabilities and other configuration parameters for the machine. For example, if a winding module can wind six rolls per cycle, then the operational cycle beginning at $t=n_{rolls}$ will involve winding the seventh through twelfth rolls.

The following examples discuss lock-on and other exemplary functionality involved in an exemplary winding operation that begins at $t=n_{rolls}$, which represents the point at which winding actually begins in the next cycle. However, it is important to note that the following examples relate to a single winding operation and that other winding, pre-winding, and/or post-winding operations associated with different modules may already be in progress, beginning, and/or ending during the time interval discussed in the following examples. Additionally, the relative scale of diagram 1000 differs from the remaining timing diagrams. Also, as was mentioned above, the actual time intervals may vary according to the speed of a machine. Diagrams 1100 through 2001 represent "zoomed in" views of particular portions which may occur within a single operational cycle, and so diagram 1000 is meant to be "to scale" with regard to count values as compared to the other diagrams.

Prior to the exemplary winding operation that begins at $t=n_{rolls}$ the material(s) being wound may need to be cut. Timing diagram 2000 illustrates a cutoff bar virtual master count value, while timing diagram 2001 illustrates the cutoff bar velocity as provided by one or more components of the cutoff bar that are synched to the cutoff bar virtual master. The cutoff bar virtual master itself is synchronized to the system virtual master so that at a certain system virtual master count the cutoff bar virtual master count begins. In this example, the cutoff module is directed to begin the cutoff bar virtual master count when the system virtual master is at value V1.

In this example, the cutoff bar virtual master in this example includes a portion where the count is a negative value. As was noted above, although asynchronous control allows for insertion and removal of components on the fly, mechanical stresses associated with starts and stops are generally to be avoided. For instance, module components are generally brought up to machine speed and then moved into full action. In general, this "startup" time frame can be accounted for in multiple ways. For instance, a virtual master count can be timed to start at a point sufficiently in advance of the time when the module needs to be at full speed. For example, if a module needs to be at full speed at a system virtual master count corresponding to $t=x$ and requires a time interval of $\Delta t$ to accelerate to machine speed, then the module virtual master can be directed to initialize at a system virtual master count corresponding to $t=(x-\Delta t)$, with the module components synchronized to begin accelerating once the module virtual master begins counting.

However, in other embodiments, system resources (such as CPU cycles of the machine central motion controller) can be conserved by avoiding the need to calculate the time interval $\Delta t$. Instead, the module virtual master can be configured to begin counting at a negative value and end counting at a positive value, with the components of the module timed so that the zero crossing corresponds to the point at which the component(s) are no longer in a pre-operational phase. Thus, the negative count values can correspond to the pre-operation activities (e.g. accelerating to a needed speed, bringing components into a ready position, etc.), while the positive count values correspond to actual operation in a process. The machine central motion controller can then specify synchronization points by identifying a system master count when a module is to be in full operation, with the module(s) determining the count value at which the module virtual master count should begin. For instance, in these examples, the zero crossing is correlated to the time at which a component or module first makes contact with material being wound (e.g. point at which a cut is made, when winding begins, etc.).

In this example, the negative count values for cutoff bar virtual master correspond to acceleration of the cutoff bar to make the cut (indicated at point 2002 in cutoff bar velocity diagram 2001) when the cutoff bar module virtual master count crosses zero (i.e. at $t=n_{cut}$). Furthermore, the timing of the zero crossing for the cutoff bar virtual master is phase shifted by an amount $t_{PS}$ from $t=n_{rolls}$. This is due to the fact that, in this example, the cutoff bar needs to cut material prior to the beginning of a wind. In this example, the cutoff bar velocity increases to a point shown at 2002 for the desired velocity for a pinch cut, decelerates to zero at 2004 after the cut is made, and then reverses to return to the "ready" position at 2006. Although this example has discussed a single pinch cut, the cutoff bar can be configured to cut the material at any time or at a number of times using any appropriate style of cut. The phase difference between the cut and the start of a wind will depend on the speed of material through the machine, the desired point of engagement, amount of tail desired, distance from the perforator, operator-desired offset, and the like. Furthermore, based on information including the position of the cut, the machine central controller will direct a ready winding module or modules to synchronize its virtual master to a point on the system virtual master to engage the newly-cut material.

Product differentiation may be possible based on phasing cutoff and the point of engagement for various winding modules. For example, a first product with a first sheet count may be obtained by cutting material at a first number of system master counts (corresponding to a time period $t_{PS1}$) preceding the master count at which the first module virtual master crosses zero. Then, a second product with a second, greater, sheet count can be obtained by phasing the cutoff from the zero crossing for the second module virtual master by a second number of system virtual master counts (corresponding to a longer time period $t_{PS2}$).

Timing diagram 1100 illustrates a winding module virtual master. For instance, winding module 1 virtual master 602a and/or winding module 2 virtual master 602b of FIG. 27 may comprise a generated signal such as shown in diagram 1100. In this example, the vertical axis represents a module count value. The actual counts may comprise any suitable numeric (or other) representation, and the present subject matter is not intended to be limited to a specific data type or format for the counts. The module count value is used by the components of the module as a basis for performing functions. Additionally, in these examples, the modules may each comprise sub-processes which utilize their own respective sub-process virtual masters that are timed to the module virtual master. The module virtual master can be directed to lock on to the system virtual master at any desired point based on the desired position of the module in the machine sequence of operation, without regard to the speed of the machine, condition of the other modules, operator phasing, or the last lock-on position used by the module. The desired position may be defined as part of control program data that specifies one or more sequences of operation. For instance, the control program data may specify multiple operational sequences that include both normal operation and operation under specified circumstances, such as in the event of different fault conditions. In this example, the winding module virtual master is directed so that it locks on to the system virtual master at count V2, which corresponds to a time shortly before $n_{rolls}$.

The module count also begins at a value that is less than zero (i.e. a negative count value) shown at 1104. Use of a negative count value may advantageously reduce calculation time and otherwise provide for easier synchronization of modules in some embodiments. In this example, the initial count value is selected so that the count value remains negative during the period between initiating the module virtual master and the beginning of the actual winding operation at $n_{rolls}$. Time interval 1102 illustrates the a phase shift $t_{PS}$ between the beginning of winding and the cut (at $t=n_{cut}$) for the roll by the cutoff bar. The distance from cutoff will depend on the desired point of engagement, amount of tail, and so on, and is determined by the difference in timing between the module virtual master and the cutoff bar virtual master.

In FIGS. 29A-29B, the time interval over which winding occurs is represented at 1106. The time interval labeled as $t_{RC}$ in FIG. 29B includes time interval 1106 and additional post-winding time period 1108 for deceleration and the like. Functions and actions performed prior to the winding operation, such as lowering the mandrel and accelerating the mandrel to a desired velocity, may be timed to the negative module virtual master count values. Once the winding operation is completed, it continues until the roll is complete at $t=(n+1)_{rolls}$ or until an event (such as a fault) occurs that otherwise ends the winding operation on that particular module.

Time period 1108 may also be included during which the module virtual master continues counting beyond 100% of a roll wind (with the module count corresponding to a completed wind illustrated at the dashed line 1101). This additional time period may be used in some embodiments for post-wind operations performed by the mandrel and other winding components, such as deceleration, tail rotation, draw, and the like.

Additionally, the additional time period may allow for on-the-fly adjustments to module operation. For instance, as was noted above, fine tuning of winding (or other) operations can be accomplished through increasing and/or decreasing the count rate of a virtual master. For example, if the count rate for a mandrel rotation virtual master is changed in operation, the rotation rate of the mandrel can be varied. However, if the count rate is decreased, then there is a risk that the decrease could affect the timing of subsequent operations by making the winding operation take longer than was planned. Therefore, the module virtual master can, in some embodiments, include additional count values as a cushion for such adjustments.

Time period 1110 represents the time during which additional operations occur after the roll is produced by the winding module. During this time period, the module is not synchronized to the rest of the machine and is thus operating asynchronously. For instance, as will be discussed below, the log can be stripped and a new core loaded for use at some point after winding is complete. However, in some embodiments, these operations occur independently and are not dependent on a virtual master count value. For instance, depending on the configuration of the winder, the particular winding module following the virtual master timing shown in 1100 may produce a log and then enter a standby state while the winder/rewinder produces several other rolls using other winding modules.

Although in the exemplary timing diagrams of FIGS. 29A-29B, the post-winding operations occupy a time interval approximately equal to that used for the winding operations, this may not always be the case. As an example, the system virtual master (and thus the components and other virtual masters synchronized thereto) may count at a very high rate per unit of time in some cases. For example, actual winding operation for a paper product may occur at a high rate of speed with, $t_{RC}$ in some embodiments, comprises about 1 to 4 seconds. If the machine attempts to remove the completed log and load a core over that time frame (when, for instance, the minimum time frame for safe removal/loading is five seconds), damage to the machine and/or product could occur. Thus, as will be noted below, in some embodiments, the core loading/roll stripping aspects are decoupled from any system master through use of asynchronous control functions.

Timing diagram 1200 of FIG. 29A represents a mandrel virtual master that is slaved to a module virtual master. For instance, diagram 1200 may represent a straight-line "cam" to achieve specified winding characteristics using the mandrel based on the mandrel rotation virtual master count. Diagram 1300 represents the resulting velocity profile using a position cam that is based on the mandrel virtual master count value. In this example, a larger value for $\Theta$ will result in a tighter wind, while a smaller value for $\Theta$ will result in a looser wind. For instance, if $\Theta$ is higher, then the mandrel will advance through its position cam faster and will therefore rotate at a higher r.p.m. for a given length of material moving through the machine, resulting in a tighter roll.

The mandrel virtual master count is initialized when the winding module virtual master count reaches a specified value. As was the case with the module virtual master, the mandrel virtual master itself features an initial negative count which, in this example, is used to accelerate the mandrel so that the mandrel reaches the desired rotational velocity at $t=n_{rolls}$. Then, based on the mandrel count and as shown in diagram 1300, the mandrel velocity is decreased as the roll is wound and eventually nears or reaches zero. For instance, one or more electronic cam profiles can be developed to control the speed, braking, and torque of the motor(s) or other devices controlling the spin of the mandrel, with the positioning of the cam(s) calculated based on the mandrel virtual master count. In this example, time period 1108 represents the post-wind motion of the mandrel. If desired, the deceleration and tail positioning can occur completely independent of virtual master time.

As noted above, the use of independent module virtual masters and sub-process master such as mandrel rotation masters, can be used to define different motion profiles so that products made by modules can have different characteristics (e.g. tighter or looser winds, different sheet counts, different roll diameters, etc.). However, the same principles can also be used to obtain the same characteristics by modules that utilize different components.

For example, a first winding module may utilize a motor with a faster torque response than the motor in a second winding module. Thus, the motor in the second winding module may require a greater pre-operational time period to reach machine speed. The mandrel rotation virtual master for the second module may differ from that of the first module in order for the second module to provide the same operational performance. For example, the mandrel rotation virtual master for the second module may begin at a lower negative count value and end at a higher positive count value relative to the values of the mandrel rotation virtual master in the first module. Thus, the second module mandrel motor will begin start-up at an appropriate time given its slower torque response. However, from the point of view of the machine central motion controller (and related control programs), the two modules can be commanded in the same manner by simply specifying a system master count values at which each module should engage without the need to calculate or otherwise account for the different pre-operational time intervals.

As was mentioned above, in some embodiments, on-the-fly adjustment of machine motion can be accomplished by varying the mandrel virtual master count rate. For instance, different winding velocity profiles can be defined as electronic cams to correlate mandrel velocity to the mandrel rotation virtual master count. However, with many motion controllers, the different cams are recalculated while the module is not in motion. Accordingly, once a module is in motion, no alterations can be made to the cam profile itself. However, by varying the gear ratio representing the ratio of a module virtual master count value to a system virtual master count value, variable winding profiles can be implemented. Of course, if the cams themselves can be modified while the module is in operation, then variable winding profiles may be implemented using a combination of varying count rates and cam characteristics.

As an example of changing winding profiles without changing cam characteristics, a tighter wind at the core of a roll can be obtained by initially increasing the mandrel rotation virtual master count rate and then decreasing the rate later on in the wind to loosen the wind at the outer portion of the roll. If the increase and decreased rates balance out, then the wind will occur over the same range of time (relative to the system virtual master) as a non-varied wind. However, if the decreased rate is not balanced out by the increased rate (e.g. the wind is looser), then a post-winding "cushion" in the module virtual master count may be desired to avoid synchronization troubles.

Turning to FIG. 29B, the mandrel lift virtual master represents another subsystem virtual master that is slaved to the module virtual master. Thus, the mandrel rotation and lift can be controlled independently of one another in this example. The vertical axis of diagram 1400 represents the mandrel lift virtual master count. As was the case of the mandrel virtual master and system virtual master, the lift virtual master count begins at a negative value selected so that the lift count reaches zero at the time that the roll wind begins. The mandrel lift virtual master count value is used as a basis for controlling the position/motion of the various lift positioning components. For example, one or more cam profiles can be developed to control the servos, actuators, and other components that change the vertical position of the mandrel, with the cam position based on the mandrel lift virtual master count. The lift position is illustrated at the vertical axis of diagram 1500 and lift velocity at the vertical axis of 1600, with lift velocity being the derivative of the position graph.

Based on the lift virtual master count, during time period $t_X$, the lift is lowered until the approximate engagement of the mandrel to the sheet of material (i.e. roll transfer). Then, the lift position is controlled to impinge into the sheet after transfer in order to deform the fabric and move web around the roll to begin the winding process. Once winding has begun, the lift position is controlled to rise according to desired roll characteristics during time period $t_{RC}$. In this example, time period 1401 represents operations after the mandrel lift count has ended and the lift virtual master is decoupled from the module virtual master.

Another advantageous application of on-the-fly adjustment can be found in varying the lift position during a winding operation. For example, a lift position motion profile may be defined based on a specified caliper of material, such as tissue that is being wound. Winding of a thicker material will result in a faster required rate of lift than a thinner material, assuming a constant winding rate and tightness. However, material, such as tissue, may vary from specifications. For example, when re-winding tissue that is being unwound from a parent roll, the wind requirements can change due to changing compressive stresses on the tissue as the parent roll decreases in size. Namely, tissue from different parts of the parent roll, which may for example have a diameter of twelve feet, can have varying caliper. Therefore, sensors can be included to determine the actual caliper of the incoming tissue, with the gear ratio of the mandrel lift virtual master adjusted based on the sensor data to increase or decrease the count rate for the mandrel lift virtual master and thereby allow for a faster or slower lift rate.

As shown in diagrams 1500 and 1600, after winding has completed, the lift is positioned for core loading and stripping operations. These operations represent asynchronous operations carried out independently of other machine functions. For instance, during time period $t_{L1}$, the lift is positioned for the log to be stripped, which occurs during $t_{RS}$. In this example, the core loading position is above the stripping position, so in time period $t_{CL}$ the lift is positioned for a new core to be loaded. Finally, during time period $t_R$, the lift is returned to "ready" status. The indication of "ready" status may also be used to indicate that the mandrel is ready to lock on to the module virtual master to begin a new winding operation and may further be used as an indication that the module virtual master is available to lock on to the system virtual master. Of course, the module preferably does not report back "ready" status to the machine central motion controller until all other components are also ready.

Timing diagram 1700 represents a log strip/core load virtual master count. The log strip/core load virtual master may be slaved to the system or subsystem virtual master at a suitable point so that a core may be loaded onto a mandrel and a roll stripped from the mandrel after winding is complete (or is otherwise halted). As with the other virtual masters, the log strip/core load virtual master count can begin at a negative initial count value so that the count equals zero at the time the winding operation begins. In this example, timing diagram 1800 illustrates the velocity of the core loading apparatus.

Furthermore, in this example, the core load velocity shows that the core loading and roll stripping maneuvers occur after the log strip/core load strip virtual master has completed a full count. This is because, in this embodiment, the load/strip operations are timed functions that occur independent of the count value of any master. Instead, once the log strip/core load virtual master reaches its maximum count value, the core strip operation is triggered and occurs during $t_{RS}$ following period $t_{L1}$. As noted above, $t_{L1}$ may represent a waiting period to allow for the mandrel lift to enter the log strip position. However, rather than a timed function, the subsequent motion actually is based on receiving commands from the module controller. For instance, the module controller may provide a command to the log strip/core load apparatus once the lift reaches a suitable position, among other prerequisites. After the log is stripped, another waiting period $t_{L2}$ occurs while the mandrel lift enters the core loading position. Then, during $t_{CL}$, the core is loaded and the log strip apparatus is returned to ready position.

By timing the core loading, log stripping, and related lift positioning functions independently of master counts, it is possible to avoid problems that may be encountered when the machine is operating at a speed that is incompatible with the desired handling of cores/finished products. Additionally, the remainder of the machine may continue to operate even in the event of a fault in the core loading/log stripping apparatus and/or core loading/log stripping can continue (if desired) even in the event of a fault during winding on other modules.

As was noted above, for example, if material is moving through the machine at a high rate of speed, then virtual master count rates (such as, for example, mandrel rotation count rates) generally will also be high. This may be advantageous, for example, in achieving a wind in a short amount of time. However, if core loading and roll stripping operations are synchronized at such speeds, then product damage and/or component damage can result. For instance, if a winding operation takes approximately 1 to 4 seconds and the roll stripping/core loading operation is synchronized to that speed, the completed rolls may be "slammed" around by too-rapid of a motion, which can dent or tear the rolls and/or possibly knock components out of alignment due to the momentum of the moving roll impacting the stripping components. As another example, a winding operation for a high sheet count may take longer than the optimal loading/unloading speed; thus, if the core load/log strip operation is timed, it is not unduly slowed by the timing of the winding operation. Accordingly, in such a case, the available utilization of a given module can be increased and the overall number of required modules may be reduced since modules can return to winding sooner.

Instead, modules, such as the log strip/core load module, can support master-independent timed functions in addition to functions timed from a virtual master. For example, the module controller may access a profile that defines motion over fixed time intervals and execute the profile upon occurrence of one or more events, such as a "log strip" or "core load" command from the machine central motion controller. As another example, the timed functions may begin once the module virtual master count reaches its final value. In any event, once the timed functions begin, the module controller can then control the lift position and actions of the core load and roll stripping apparatus independent of the rate of the functions synchronized to the system or subsystem virtual master counts.

Of course, in other embodiments, components responsible for core loading and/or log stripping can be synchronized to one or more masters. Additionally, any suitable component(s) can be controlled by timed functions or by a combination of timed functions and synchronized functions. Although the example above discussed timed functions regarding core loading and log stripping, it is to be understood that other functions can be timed and/or commanded independently of master count values, whether at the module level or at the system level. Additionally, although in this example no log strip/core load apparatus motion is synchronized to the log strip/core load virtual master count value, this may not always be so. For instance, different winding characteristics can be achieved by varying the position of the core/partially wound roll during a winding operation. For example, by using the load/strip apparatus to oscillate the core in a transverse direction relative to the direction of the material being wound, spiral, cone, and other characteristics can be introduced.

A winder/rewinder may include other modules that can be selectively engaged to provide for different products during different winds. For example, an applicator module can comprise one or more components that apply an additive or additives, such as a lotion or antibacterial compound, to a web. For instance, one or more electronic cams may control a spray or other actuator. The additive(s) can be applied to certain lengths of material when winding a premium product, but not to other lengths of material. For example, the machine central motion controller may direct the cutoff module to provide a new leading edge and apply lotion to a length of web. The edge may be engaged and the material may be wound by a first module. Once the desired sheet length is reached, the web may be cut again to define a new leading edge. However, in the next wound log, no lotion or other additives are applied. The new leading edge is engaged by the next available winding module.

In some embodiments, the control system can support on-the-fly redefinition of the virtual master position. For instance, in the event of a fault, as noted above, a module may be de-synchronized and disengaged and the control system can determine which (if any) module is available to begin operation in place of the disengaged module(s). Rather than changing the lock-on point of the next available module(s), it may be advantageous to redefine the system virtual master count to a value just short of the next available module's lock-on point. For example, relatively speaking, a control system may require a significant time interval to recalculate and re-command winding modules to engage at different points in the event of a fault. During the time interval in which the module lock-on positions are re-calculated, significant amounts of material may move through the machine and such materials may be wasted if not operated upon. For example, in a winder/rewinder, product may continue to move through the machine on a conveyor that is not synchronized to any virtual master count. Therefore, by redefining the position of the virtual master instantaneously, waste can be reduced.

As was noted earlier, the principles of asynchronous control discussed herein can be scaled upward or downward. For instance, a system virtual master may correspond to a signal base for a machine comprising a plurality of modules, with some or all of the modules having virtual masters which begin counting at respective system master lock-on values. Each module may comprise components or sub-assemblies which each operate based on a component virtual master and/or sub-assembly virtual master which begin counting at respective module virtual master lock-on values.

However, in some embodiments, the control system may be used with multiple machines selectively synchronized to the same system virtual master. In such embodiments, each machine would be treated in the same manner as a module is treated in a single-machine embodiment.

IV. Registration and Inspection System and Methods

As was discussed above, a winder can include a plurality of independent modules with winding and other controls configured specifically for each module in a manner so that modules do not necessarily rely on successful operation of other modules. During the winding process, one or more defects can occur during the winding process. These defects need to be monitored to determine whether to cull defective products from the winder and to take necessary steps to remedy the cause of the defect and/or initiate an immediate cutoff of the web and transfer to the next available winding module.

To monitor and track defects, the winder can include a registration and inspection system that includes fast scan capabilities and hardware capable of defect detection, task scheduling, and product registration during the high speed and continuous manufacture and winding of finished rolled products. The registration and inspection system can accommodate the modular and asynchronous winder with run through fault capabilities. Use of the registration and inspection system with the winder enables low defect rates, rapid development cycles and the gathering of process data to drive efficiency improvements. Precision and accuracy at defect recognition and in culling defective products allows sustained high speed operation without risking defective products reaching the consumer. In addition, the registration and inspection system according to certain exemplary embodiments of the present disclosure can be implemented using inexpensive photo-eye technology that provides for superior process data when compared to typical inspection systems.

Although some of the following examples discussed later relate to a modular or flex winder, it will be appreciated that the registration and inspection principles discussed herein can be equally applicable to any type of machine or toll that includes a winding module for winding a web into a rolled product.

Figure 30:
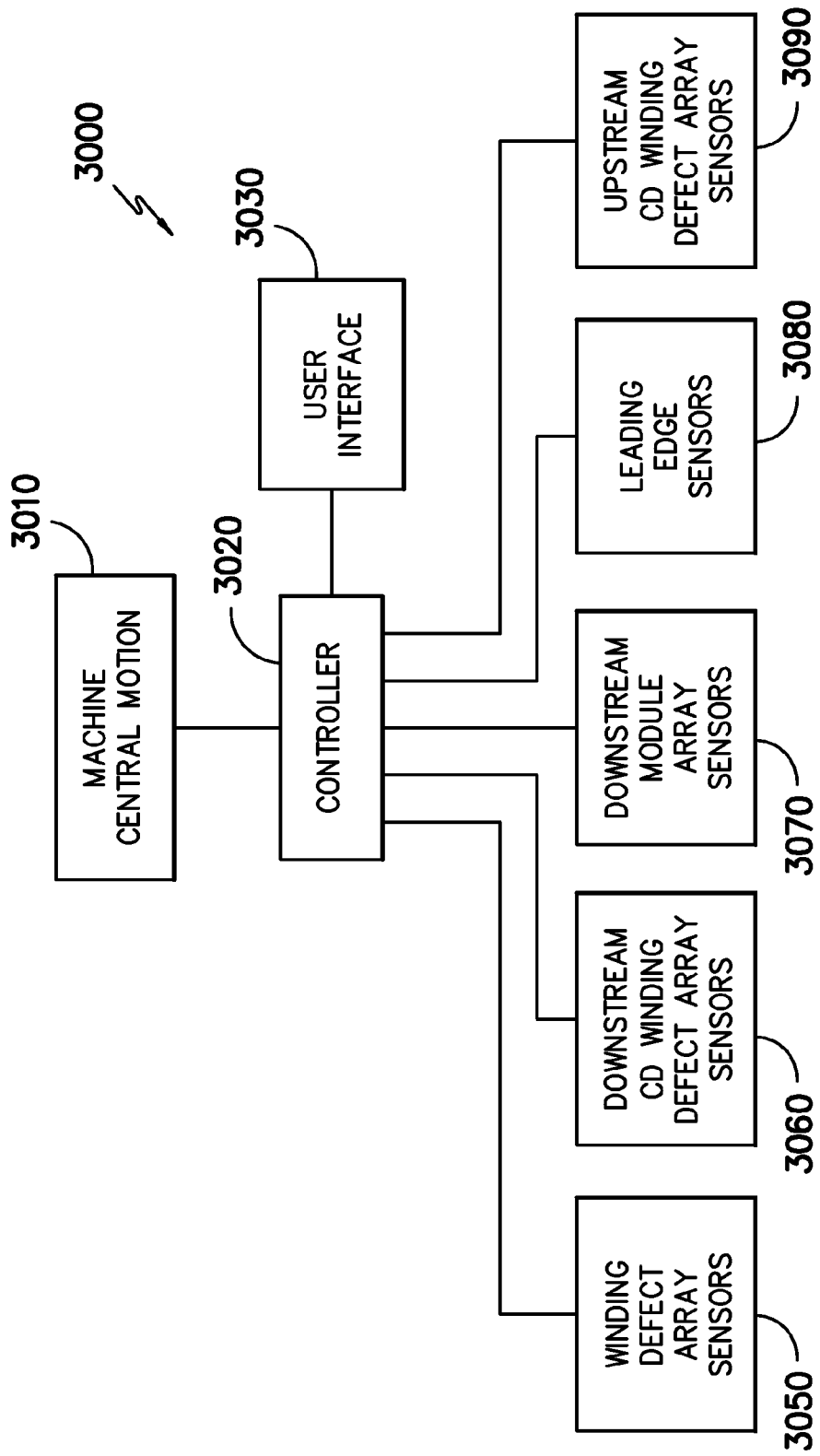
FIG. 30 is a block diagram illustrating an exemplary inspection system according to an exemplary embodiment of the present disclosure.

FIG. 30 is a block diagram of an exemplary inspection system 3000 according to an exemplary embodiment of the present disclosure. Inspection system 3000 includes a controller 3020 coupled to a variety of sensor configurations, including winding defect array sensors 3050, downstream cross-direction winding defect sensors 3060, downstream module array sensors 3070, leading edge sensors 3080 and upstream cross-direction winding defect sensors 3090. Controller 3020 can further be coupled to a user interface 3030 and a machine central motion controller 3010. Machine central motion controller 3010 can be part of an asynchronous or central control system for providing winding and other controls for the winder.

Controller 3020 and machine central motion controller 3010 can include any suitable type or arrangement of computing devices, such as general-purpose computers, specialized microprocessor-based hardware controllers, programmable logic controllers (PLCs), and the like. In some embodiments, some or all aspects of controller 3020 and/or machine central motion controller 3010 can be implemented as separate logical units using the same computing device or devices. Some aspects of controller 3020 and/or central motion controller 3010 may be implemented by software or specialized hardware (such as application-specific integrated circuits).

Controller 3020 can be coupled to various components of system 3000 through any suitable type or combination of types of data connections. For instance, connection can include Ethernet connections, control net connections, and/or any other suitable connection types. Furthermore, in this example, individual links are shown between controller 3020 and the various components of system 3000. However, in other embodiments, the components and controller 3020 can be connected to a network and/or to each other via peer connections.

In operation, winding defect array sensors 3050, downstream cross-direction winding defect sensors 3060, upstream cross-direction winding defect sensors 3090, and downstream module array sensors 3070 are used to detect defects that occur during the winding process. Defects can be any deviations from expected process parameters for the winding process. Defects can be detected by determining the lack or presence of a web in a particular region of the winder for a period of scans, time, or web distance. The sensitivity of winding defect array sensors 3050, downstream cross-direction winding defect sensors 3060, upstream cross-direction winding defect sensors 3090, and downstream module array sensors 3070 can be adjusted to ensure the capturing of all defects that require culling of the rolled product, but not so sensitive that saleable products are culled from the winding process.

Controller 3020 monitors defects detected by the various sensors and processes, analyzes and reports information associated with the defects as will be discussed in more detail below. In particular embodiments, controller 3020 can have a fast scan rate, such as less than about 3 ms, to provide enhanced precision and accuracy in the detection of defects. In addition to providing defect monitoring and analysis capabilities, controller 3020 can be configured to control various aspects of the winder. Registration capabilities of system 3000 can be implemented using leading edge sensors 3080. For instance, leading edge sensors 3080 can be positioned in the winder to verify the presence of web, leading edge position of the web, and detection of leading edge defects on the web transport apparatus.

User interface 3030 can be used by an operator to manipulate and control various aspects of system 3000 through one or more input devices, such as a keyboard, mouse, voice interface, touch screen, key pad, etc. Manipulation may include optimization of sensor position relative to the moving web, teaching the sensor, configuring cull characteristics for the sensor, enabling/disabling the sensor, and troubleshooting operation of the sensor. User interface 3030 can provide a graphic user interface, examples of which will be set forth below, that provides information gathered and processed by inspection system 3000 and that allows for set-up, configuration, and reporting functions of system 3000.

Figure 31:
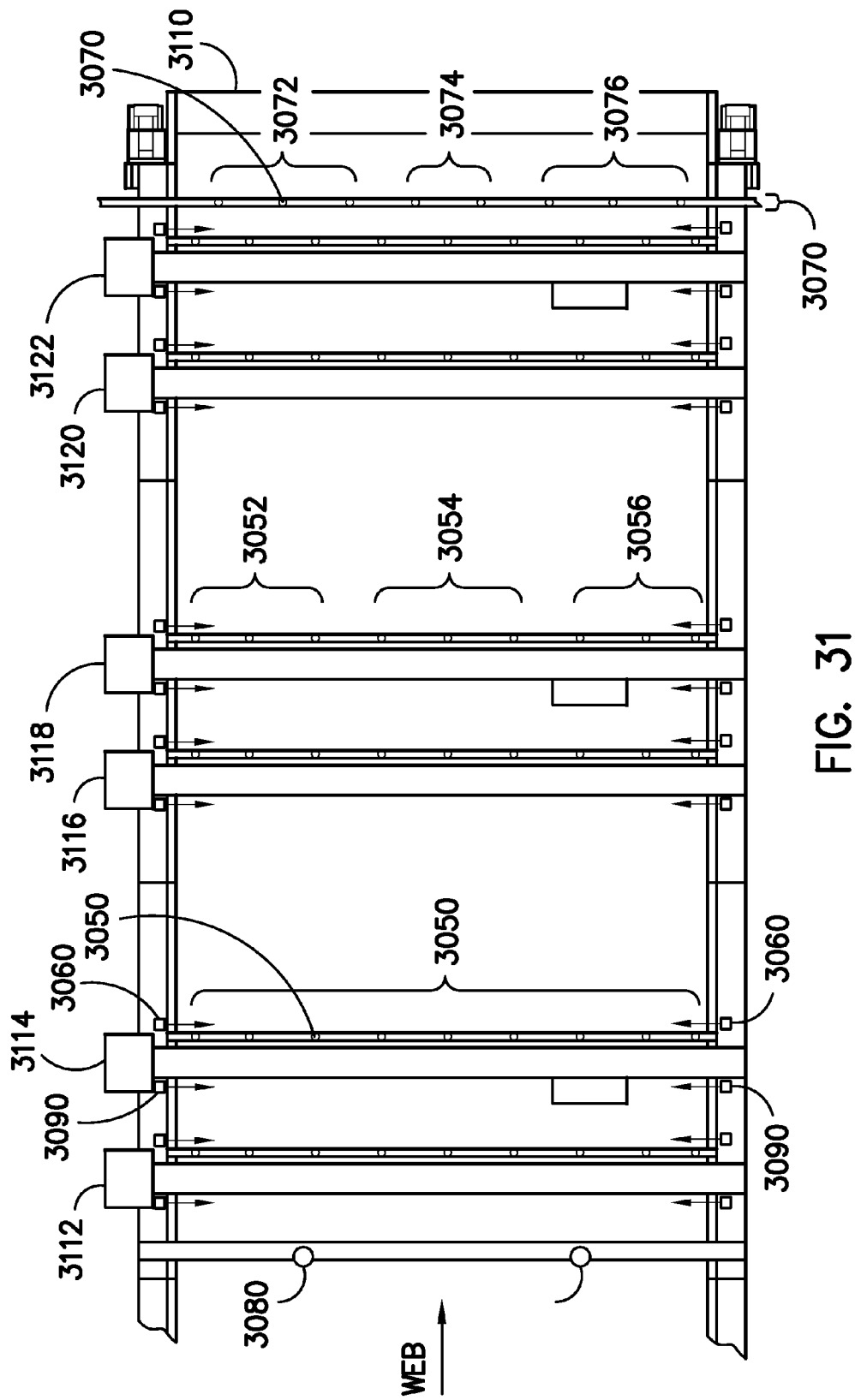
FIG. 31 is a plan view of an exemplary winder illustrating an exemplary sensor layout for an exemplary inspection system according to an exemplary embodiment of the present disclosure.

With reference now to FIG. 31, the positioning and configuration of the various sensor groups of system 3000 within an exemplary winder will be discussed. FIG. 31 illustrates an exemplary winder that includes a web transport apparatus 3110 and six exemplary winding modules 3112, 3114, 3116, 3118, 3120, and 3122. While the winder illustrated in FIG. 31 includes six independent winding modules 3112, 3114, 3116, 3118, 3120, and 3122, it will be understood that more or fewer winding modules can be used depending on the particular winder and application of system 3000.

As illustrated, leading edge sensors 3080 are positioned upstream of the winding modules 3112, 3114, 3116, 3118, 3120, and 3122. Leading edge sensors 3080 are positioned to scan a section of the web that passes on the web transport apparatus beneath the leading edge sensors 3080. Leading edge sensors 3080 can be photo-eye sensors or other suitable sensors used to verify the presence or lack of presence of the web on the web transport apparatus, to identify a leading edge of the web, to detect leading edge defects on the web transport apparatus or to perform other suitable functions.

Precision and accuracy of inspection and defect detection of inspection system 3000 are achieved, at least in part, by associating multiple sensor groups per winding module 3112, 3114, 3116, 3118, 3120, and 3122. A first group of sensors, discussed with respect to their position and configuration with relation to winding module 3114, is the winding defect array sensors 3050. Winding defect array sensors 3050 are mounted downstream of each winding module 3112, 3114, 3116, 3118, 3120, and 3122, and are disposed across a width of web transport apparatus 3110. In FIG. 31, nine winding defect array sensors 3050 are associated with each winding module 3112, 3114, 3116, 3118, 31120, and 3120. However those of ordinary skill in the art, using the disclosures provided herein, will understand that more or fewer winding defect array sensors 3050 can be associated with each winding module 3112, 3114, 3116, 3118, 3120, and 3122 as desired.

Winding defect array sensors 3050 are positioned to scan a region of the web transport apparatus 3110 at a location downstream of winding module 3114. Each winding defect array sensor 3050 is discrete and scans a cross section of a portion of the web transport apparatus 3110 that passes beneath the winding defect array sensor 3050. Winding defect array sensors 3050 can be photo-eye sensors or other suitable sensors configured to look for defects via presence or lack of web on the web transport apparatus at specified intervals. As will be discussed in more detail below, winding defect array sensors 3050 can be segmented into inspection sensor segments to classify defects into a defect profile. For instance, winding defect array sensors 3050 can be segmented into an operator side sensor segment 3052, a middle sensor segment 3054, and a drive side sensor segment 3056.

A second sensor group includes downstream cross-direction winding defect sensor 3060. Each winding module 3112, 3114, 3116, 3118, 3120, and 3122 is associated with a cross-direction winding defect sensor 3060. However the position and configuration of cross-direction winding defect sensor 3060 will be discussed with reference to winding module 3114. Downstream cross-direction winding defect sensor 3060 is positioned to scan across a cross direction of the winding module 3114 at a location proximate and downstream of winding module 3114. Downstream cross-direction winding defect sensor 3060 can be an emitter/receiver type photo-eye sensor or other suitable sensor configured to look for defects via presence or lack of web across the full cross-direction width of winding module 3114. Defects detected by downstream cross-direction winding defect sensor 3060 can be classified into a defect profile based on inspection window segments as will be discussed in detail below.

A third sensor group includes upstream cross-direction winding defect sensor 3090. Each winding module 3112, 3114, 3116, 3118, 3120, and 3122 is associated with a cross-direction winding defect sensor 3090. However the position and configuration of cross-direction winding defect sensor 3090 will be discussed with reference to winding module 3114. Upstream cross-direction winding defect sensor 3060 is positioned to scan across a cross direction of the winding module 3114 at a location proximate and upstream of winding module 3114. Upstream cross-direction winding defect sensor 3090 can be an emitter/receiver type photo-eye sensor configured to look for defects via presence or lack of web across the full cross-direction width of winding module 3114. For instance, the upstream cross-direction winding defect sensor 3090 can detect or monitor bunching of the web upstream of the winding module. Defects detected by cross-direction winding defect sensor 3090 can be classified into a defect profile based on inspection window segments as will be discussed in detail below.

A fourth group of sensors includes downstream module array sensors 3070. Downstream module array sensors 3070 are mounted downstream of all winding modules 3112, 3114, 3116, 3118, 3120, and 3122, and are disposed across a width of web transport apparatus 3110. Eight downstream module array sensors 3070 are illustrated in FIG. 31, however those of ordinary skill in the art, using the disclosures provided herein, will understand that more or fewer downstream module array sensors 3070 can be used as desired.

Downstream module array sensors 3070 are positioned to scan a region of the web transport apparatus 3110 at a location downstream of all winding modules 3112, 3114, 3116, 3118, 3120, and 3122. Each downstream module array sensor 3070 is discrete and scans a cross section of a portion of the web transport apparatus 3110 that passes beneath the downstream module array sensor 3070. Downstream module array sensors 3070 can be photo-eye sensors configured to look for defects via presence or lack of web on the web transport apparatus at specified intervals. The downstream module array sensors 3070 can serve as a back up to the winding defect array sensors 3050. As will be discussed in more detail below, downstream module array sensors 3070 can be segmented into downstream module inspection sensor segments to classify defects into a defect profile. For instance, downstream module array sensors 3070 can be segmented into an operator side sensor segment 3072, a middle sensor segment 3074, and a drive side sensor segment 3076.

Figure 32:
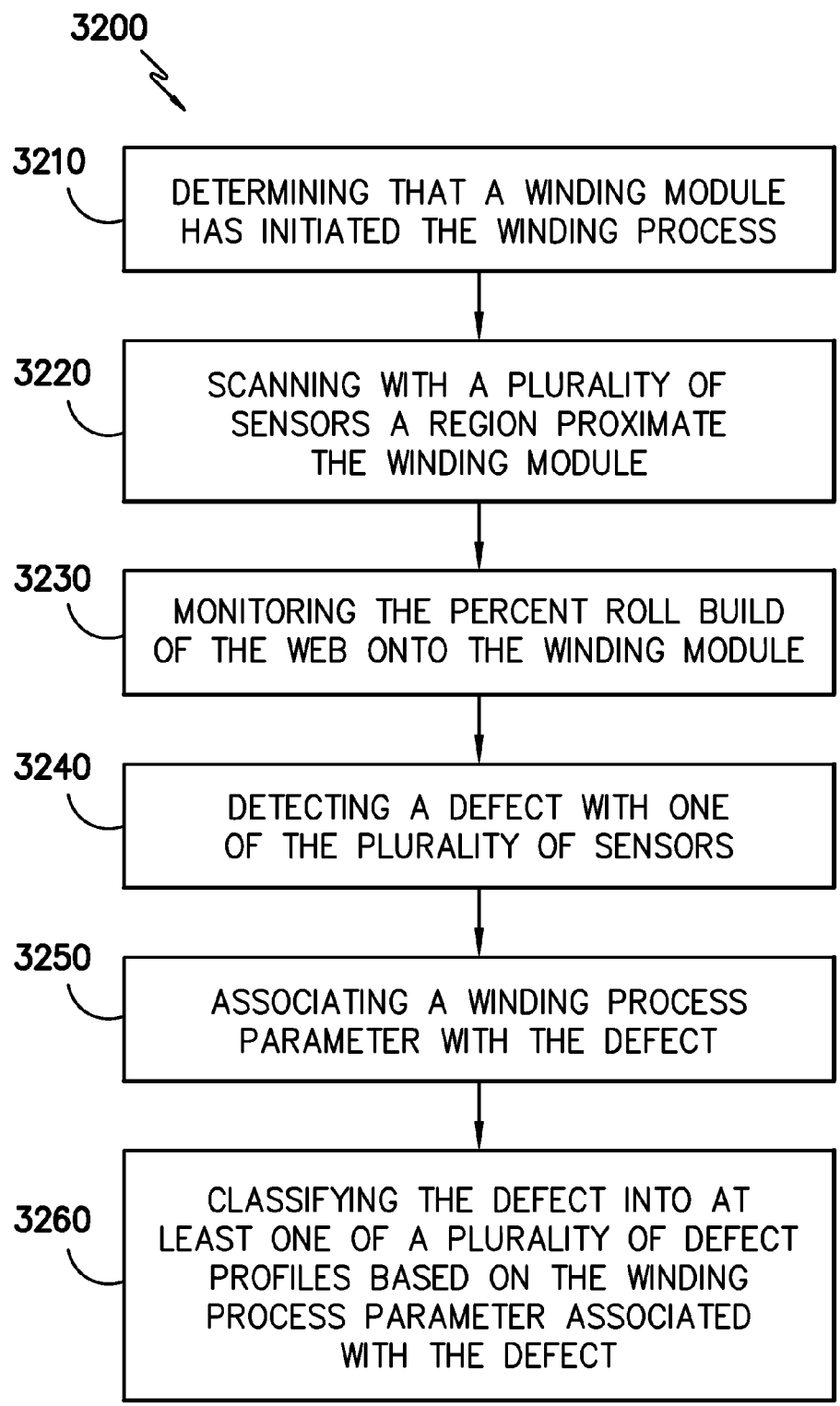
FIG. 32 is a flow diagram of an exemplary inspection method according to an exemplary embodiment of the present disclosure.

FIG. 32 provides a block diagram of exemplary method steps that can be performed by one or more components of system 3000. At 3210, controller 3020 can be configured to determine that a particular winding module, such as one of winding modules 3112, 3114, 3116, 3118, 3120, and 3122, has initiated the winding process. Controller 3020 can determine that a particular winding module has initiated the winding process by receiving information from machine central motion controller 3010 or by monitoring web transfer using one or more sensors used in inspection system 3000.

At 3220, controller 3020 directs a plurality of sensors to scan a region proximate the winding module that has initiated the winding process. The sensors can include winding defect array sensors 3050, downstream cross-direction winding defect sensors 3060, upstream cross-direction winding defect sensors 3090, or downstream module array sensors 3070. The position and configuration of these sensors in relation to an exemplary winding module was discussed with reference to FIG. 31. The sensors, which can be photo-eye sensors or other suitable sensors, scan a region proximate the winding module to determine the presence or lack of presence of a web.

At 3230, the system 3000 monitors the percent roll build of the web onto the winding module. Percent roll build of a web can be monitored and measured as a percentage of total roll build for a finished rolled log or as web distance with zero distance being the point at which the web is transferred to the winding module. Percent roll build information can be received at controller 3020 from machine central motion controller 3010 or from one or more sensors used in system 3000.

According to embodiments of the present disclosure, percent roll build of the web can be used as a winding process parameter for several purposes. For instance, controller 3020 interfaces with machine central motion controller 3010 based at least in part on percent roll build of the web onto the winding module. In addition, percent roll build can be used as a winding process parameter associated with the defect to classify the defect into one or more defect profiles or as an absolute tag to identify the precise position in a finished log in which the defect occurs.

At 3240, one of the plurality of sensors of system 3000 detects a defect. A defect is detected when one of the sensors, which can be a photo-eye sensor or other suitable sensor, detects the presence or lack of a web for a defined number of scans, known as the scan filter count for the sensor. The scan filter count for the sensors can be adjusted to make the sensors more sensitive or less sensitive as desired. For instance, in a particular implementation, the scan filter count for sensors used in system 3000 can be adjusted independently in the various window segments defined by percent of roll build. The scan filter count can be specified as a number of scans or as web distance. Specifying the scan filter count as web distance allows sensor sensitivity to be configured independent of varying machine speeds.

At 3250, controller 3020 associates a winding process parameter with the defect. For instance, in particular implementations, controller 3020 associates the percent roll build of the web with the defect in addition to the identity of the specific sensor(s) which first detected the defect to break down the defect into specific categories for further analysis. If a sensor detects a defect, controller 3020 reports the specific sensors that detected the defect and the percent roll build at which the sensor detected the defect. Percent roll build reporting allows a histogram to be generated showing defect frequency in relation to length of web wound on product rolls.

At 3260, controller 3020 classifies the defect into at least one of a plurality of defect profiles based on the winding process parameter associated with the defect. In this manner, the system 3000 can provide enhanced feed back via defect profiling and is different from other registration and inspection systems which simply report that a defect occurred. According to exemplary embodiments of the present disclosure, defect profiling can occur through one or more of three primary methods, including segmentation of the roll build of a web onto a winding module into discrete inspection windows, segmentation of winding defect array sensors and/or downstream module array sensors into inspection sensor segments, and configuration of sensor sensitivity to defect sizes based on the number of sensing scans of the sensors or web distance.

In particular embodiments, defect profiling occurs by segmenting roll build into a plurality of inspection window segments for the winding defect array sensors 3050, the downstream cross-direction winding defect sensors 3060, and the upstream winding defect array sensors 3090. The number and size of the inspection window segments can be customized based on product parameters or other factors. The inspection windows can be defined based on percent roll build of the product or in terms of web distances, with zero distance being the point at which the web is transferred to the winding module.

In a particular embodiment, the roll build of a web onto a winding module is segmented into three inspection windows defined as follows:

Roll transfer window: Window 1<% roll build (web distance) <Window 2;

Roll build window: Window 2<% roll build (web distance) <Window 3

Post roll build window: Window 3<% roll build (web distance)<Window 4.

Window 1 can be defined to be a specified percent roll build or web distance to exclude the start of the wind following sheet transfer. This setting compensates for the offset distance between the winding module centerline and sensor positions. In addition, this setting provides a specific tolerance limit for acceptable transfer defect size. This can be an important feature due to the variation of roll transfer attributes based on various process conditions. Window 2 can be a specified percent roll build or web distance to distinguish roll transfer defects versus roll build defects. Window 3 can be a specified distance to exclude the end of the wind. Window 4 can define a post winding inspection window to detect defects that can occur once the winding is complete and the rolled product is in transit to the next operation.

Figure 33:
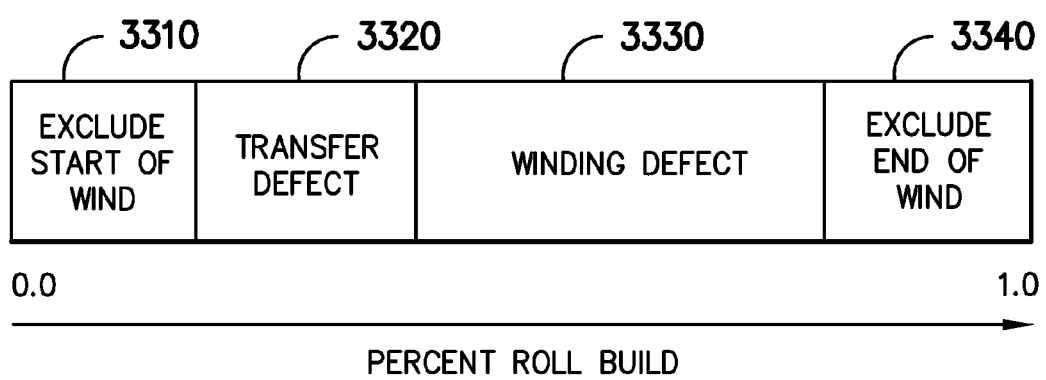
FIG. 33 is an exemplary inspection window segmentation based on roll build according to an exemplary embodiment of the present disclosure.

FIG. 33 provides a graphical representation of an exemplary segmentation of a roll build into a roll transfer inspection window and a roll build inspection window. As illustrated, FIG. 33 has segmented the roll build into four segments 3310, 3320, 3330, and 3340. Two of the segments, namely 3320 and 3330, define active inspection window segments in which sensors are actively scanning for defects during the winding process. The other two segments, namely 3310 and 3340, define periods of exclusion in which sensors may not be actively scanning for defects or during which defects are not reported or recognized as possible cull events. In particular, segment 3310 is defined to exclude the start of the wind following web transfer. Segment 3320 defines a roll transfer inspection window. Segment 3330 defines a roll build inspection window. Segment 3340 is defined to exclude the end of the wind.

In operation, controller 3020 of system 3000 monitors percent roll build of a web onto a winding module. The system 3000 segments the roll build into a plurality of inspection windows, such as a roll transfer inspection window, a roll build inspection window, and a post roll transfer inspection window as discussed above. When a defect is detected, the percent roll build of the web onto the winding module is associated with the defect. The defect can then be classified into one of a plurality of defect profiles defined at least in part by the plurality of inspection windows based on the percent roll build of web when the defect occurred. For instance, if the defect occurred at a percent roll build that is in the roll transfer inspection window, the defect can be classified as a roll transfer defect. If the defect occurred at a percent roll build that is in the roll build transfer inspection window, the defect can be classified as a roll build defect. If the defect occurred at a percent roll build that is in the post roll build transfer inspection window, the defect can be classified as a post roll build defect. In this manner, enhanced feedback concerning defects can be provided above and beyond reporting that a defect has occurred.

Alternatively or in addition to defect profiling based on inspection windows, defect profiling can also be accomplished by segmenting sensors used in system 3000 into a plurality of inspection sensor segments. For instance, winding module array sensors 3050 and downstream module array sensors 3070 can be segmented into a plurality of inspection sensor segments. As can be seen in FIG. 31, winding module array sensors 3050 have been segmented into an operator side sensor segment 3052, a middle sensor segment 3054, and a drive side sensor segment 3056. Similarly, downstream module array sensors have been segmented into an operator side sensor segment 3072, a middle sensor segment 3074, and a drive side sensor segment 3076.

Controller 3020 can classify a defect into one of the inspection sensor segments based at least in part on the identity of the sensor or sensors that first detected the defect. For instance, if winding defect array sensors 3050 associated with the operator side sensor segment 3052 first detected the defect, the defect can be classified as an operator side defect. If winding defect array sensors 3050 associated with the middle sensor segment 3054 first detected the defect, the defect can be classified as a middle defect. If winding defect array sensors 3050 associated with drive side sensor segment 3056 first detected the defect, the defect can be classified as a drive side defect.

Similarly with respect to downstream module array sensors 3070, if downstream module array sensors 3070 associated with operator side sensor segment 3072 first detected the defect, the defect can be classified as an operator side defect. If downstream winding defect array sensors 3070 associated with middle sensor segment 3074 first detected the defect, the defect can be classified as a middle defect. If winding defect array sensors 3070 associated with drive side sensor segment 3076 first detected the defect, the defect can be classified as a drive side defect.

In a particular embodiment, defects can be classified into defect profiles based at least in part on both inspection window segments and inspection sensor segments and based on the particular group of sensors to detect the defect. For instance, in a particular embodiment, the total number of defect profiles for a defect can be eighteen defect profiles. This includes nine defect profiles associated with winding module array sensors 3050, three defect profiles associated with downstream cross-direction winding defect sensors 3060, three defect profiles associated with upstream cross-direction winding defect sensors 3090, and three defect profiles associated with downstream module array sensors 3070 as follows:

Winding Module Array Sensor Defect Profiles
Winding Module Array Operator Side Roll Transfer Defect (% roll build in roll transfer window and first sensor in operator side sensor segment 3052);
Winding Module Array Operator Side Roll Build Defect (% roll build in roll build window and first sensor in operator side sensor segment 3052);
Winding Module Array Operator Side Post-Roll Build Defect (% roll build in post-roll build inspection window and first sensor in operator side sensor segment 3052);
Winding Module Array Middle Roll Transfer Defect (% roll build in roll transfer window and first sensor in middle sensor segment 3054);
Winding Module Array Middle Roll Build Defect (% roll build in roll build window and first sensor in middle sensor segment 3054);
Winding Module Array Middle Post-Roll Build Defect (% roll build in post-roll build inspection window and first sensor in middle sensor segment 3054);
Winding Module Array Drive Side Roll Transfer Defect (% roll build in roll transfer window and first sensor in drive side sensor segment 3056);
Winding Module Array Drive Side Roll Build Defect (% roll build in roll build window and first sensor in drive side sensor segment 3056);
Winding Module Array Drive Side Post-Roll Build Defect (% roll build in post-roll build inspection window and first sensor in drive side sensor segment 3056);
Downstream Cross-Direction Winding Defect Sensor
Downstream Cross-Direction Roll Transfer Defect (% roll build in roll transfer window and first sensor being a downstream cross-direction winding defect sensor 3060);
Downstream Cross-Direction Roll Build Defect (% roll build in roll build window and first sensor being a downstream cross-direction winding defect sensor 3060);
Downstream Cross-Direction Post-Roll Build Defect (% roll build in post-roll build window and first sensor being a downstream cross-direction winding defect sensor 3060).
Upstream Cross-Direction Winding Defect Sensor
Upstream Cross-Direction Roll Transfer Defect (% roll build in roll transfer window and first sensor being an upstream cross-direction winding defect sensor 3090);
Upstream Cross-Direction Roll Build Defect (% roll build in roll build window and first sensor being an upstream cross-direction winding defect sensor 3060);
Upstream Cross-Direction Post-Roll Build Defect (% roll build in post-roll build window and first sensor being an upstream cross-direction winding defect sensor 3060).
Downstream Module Array Sensors
Downstream Module Operator Side Defect (first sensor in operator side sensor segment 3072);
Downstream Module Middle Defect (first sensor in middle sensor segment 3074);
Downstream Module Drive Side Defect (first sensor in drive side sensor segment 3076);

The sensitivity of inspection system 3000 to various defects can be adjusted by configuring controller 3020 and/or the detection sensitivities of the various sensors used in system 3000. For instance, sensitivities can be adjusted by varying the number of scans or web distance for each inspection window by product, grade, and sensor type. This provides the capability to provide precise tolerances for defects based on process steps. In addition, detection sensitivity for the various winding defect array sensors 3050, cross-direction winding defect sensors 3060, and downstream module array sensors 3070 can be adjusted by adjusting the scan filter count for the various sensors. The scan filter count defines the number of scans or web distance for the sensor to detect the presence or lack of web before detecting a defect. The lower the scan filter count for the sensor, the greater the sensitivity of the sensor to defects.

In a particular embodiment, controller 3020 can adjust the scan filter count for the winding defect array sensors 3050, cross-direction winding defect sensors 3060, and downstream module array sensors 3070 based on inspection windows. For instance, the scan filter count for the sensor during the roll build inspection window can be greater than the scan filter count for the sensor during the roll transfer inspection window to reduce false positives. The flexibility in configuring the sensitivity of system 3000 to defects provides numerous advantages over existing technologies known in the art.

The incorporation of web transfer and roll build dynamics to associate defects with winding locations in the cross-direction orientation of winding modules (i.e. defect profiling via segmentation of the winding process) provides numerous advantages. For instance, defect types can be inferred by knowing cross-direction position and region of the roll build where the defect occurred. In addition, defect profile information can be used in the development of the winding process to eliminate product risks and rejectable defects to provide run-through fault capability. Configuration of defect sensitivity provides a key process control tool for controlling waste by ensuring the registration and inspection system captures rejectable defects but does not result in the culling of saleable products. Importantly, defect profiling and scan capabilities to detect defects within the first web wrap during roll transfer provides data to categorize and determine root causes of defects caused by reliability, housekeeping, set-up and other areas contributing to variability. Existing inspection systems and methods do not allow this kind of variability because they typically require a web break or other large defect to trigger the system.

Figure 34:
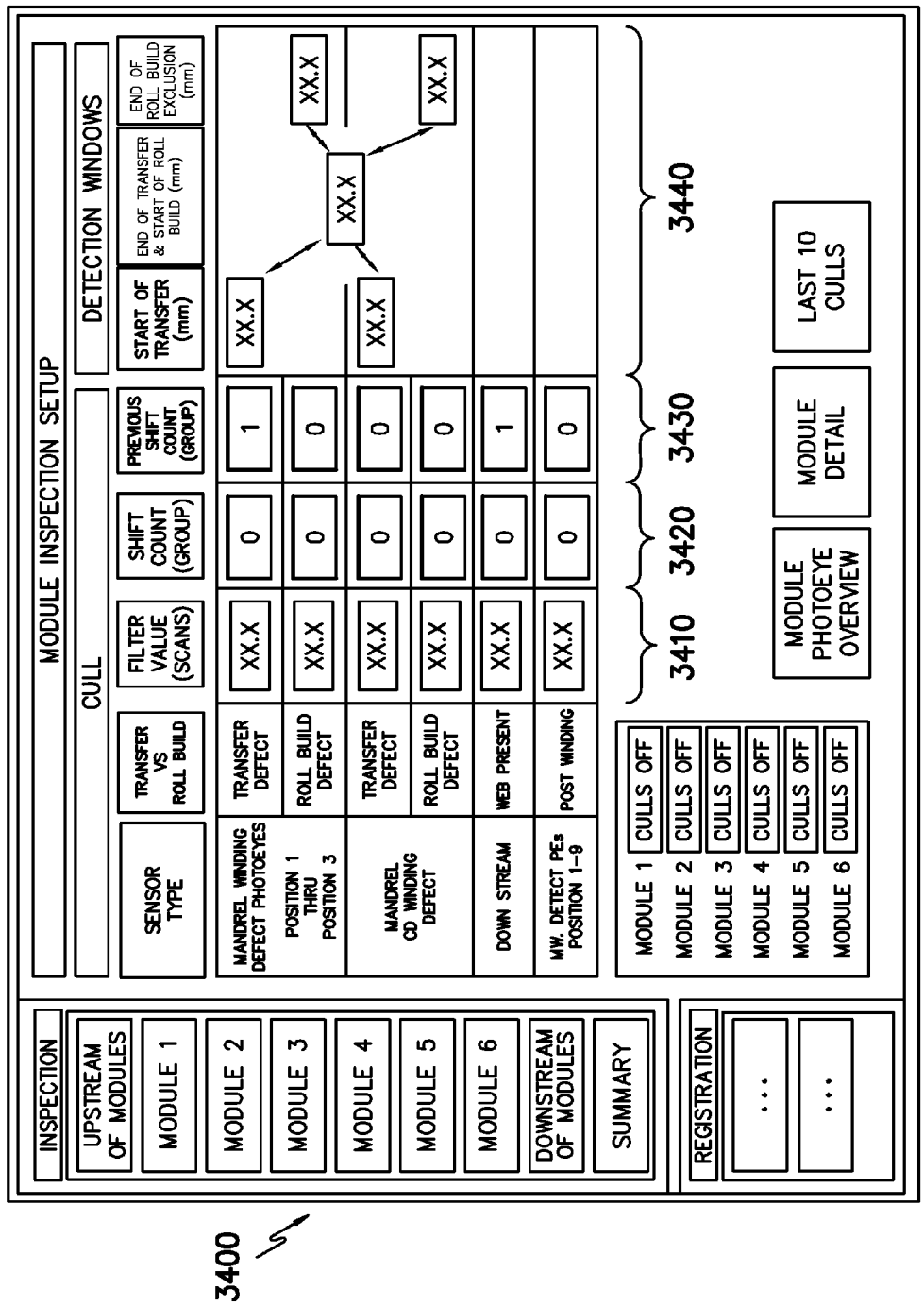

FIGS. 34-37 illustrate exemplary display information for display on a user interface associated with an exemplary embodiment of the present disclosure. With reference to FIG. 34, display screen 3400 provides a graphical interface that can be used by a user to set up module inspection parameters. As illustrated, display screen 3400 includes on the left hand side a plurality of options for allowing a user to select the particular winding module for set up and configuration. The display screen 3400 provides various different types of information to user, including sensor type and configuration settings for both the roll transfer inspection window and the roll build inspection window.

In fields 3410, a user can specify a scan filter count for a particular sensor to detect a defect. The scan filter count can be specified in terms of percent roll build or in terms of web distance. The scan filter count for the roll build inspection window can be configured by a user to be greater than the scan filter count for the roll transfer inspection window. Fields 3420 and 3430 provide a count of past detected defects for particular sensors for the current shift and the previous shift respectively. Field 3440 allows for user configuration of inspection windows. For instance, the user can specify values into field 3440 to configure the start and end of the roll transfer inspection window and roll build inspection window. The user can also specify that the roll transfer inspection window exclude a period of the roll build following the initiation of the winding process. Similarly, the user can specify that the roll build inspection window exclude a period of the roll build immediately preceding the termination of the winding process.

FIG. 35 illustrates exemplary display screen 3500 that can be used to provide information concerning individual sensors associated with a winding module. Display screen 3500 can provide a graphical interface enabling a user to teach and enable various sensors associated with a winding module. Field 3510 provides an indication to a user as to whether a particular sensor has been enabled and can be used to scan for defects. If a sensor is not enabled, the user can use this graphical interface to teach the sensor and enable the sensor for defect detection. Field 3520 can be used to provide indicia to a user that a particular sensor is currently detecting the presence or lack of web. For instance, the field 3520 can be colored white when a particular sensor is currently detecting the presence of a web and clear when a particular sensor does not currently detect the presence of a web. Other information provided by display screen 3500 includes sensor names, defect counts for particular sensors for current and previous shifts, as well as temporary defect counts.

Figure 36:
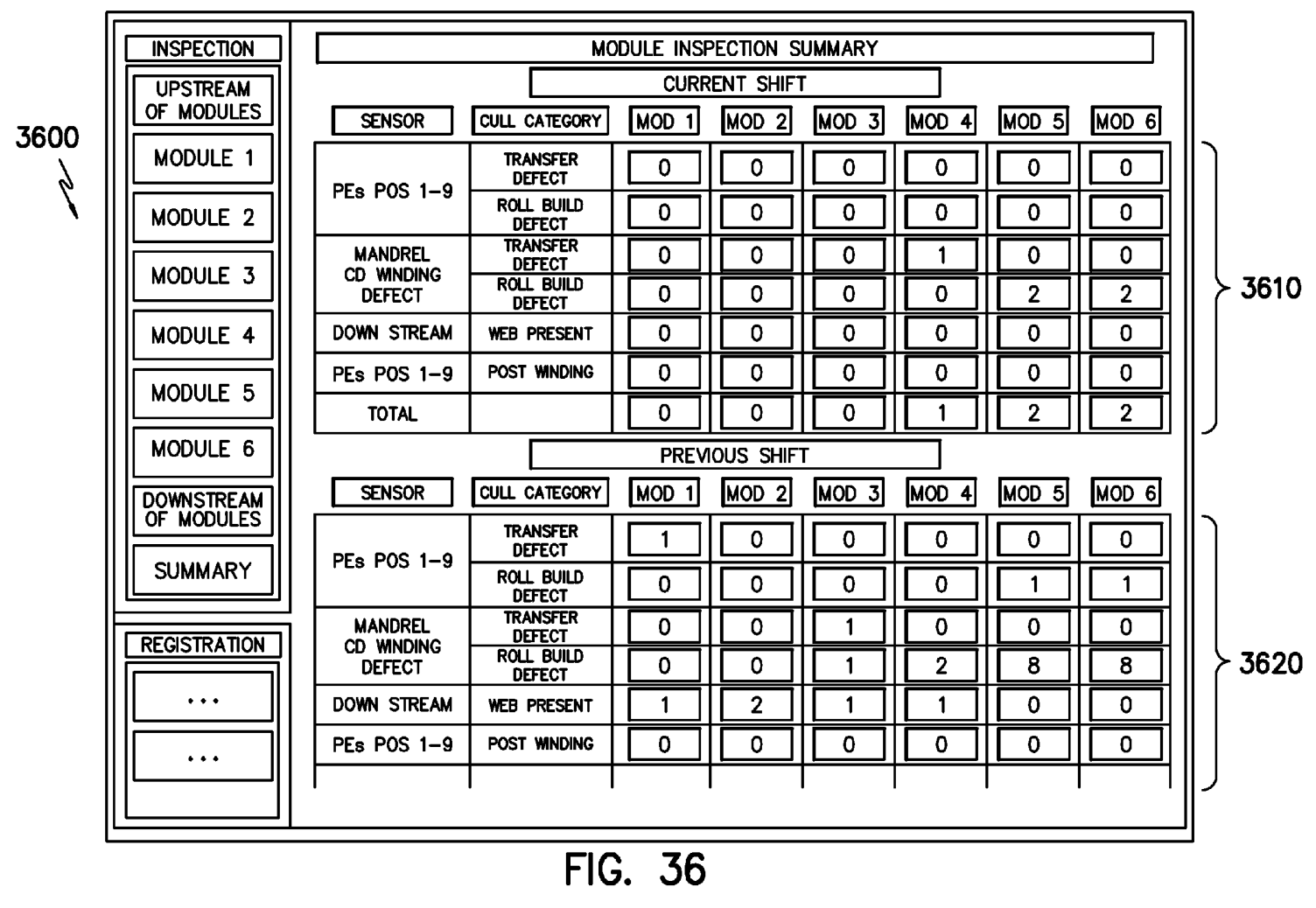

FIG. 36 illustrates exemplary display screen 3600 that can be used to provide a module inspection summary for all winding modules to a user. Fields 3610 provide defect count information for particular sensors associated with individual winding modules during a current shift. Fields 3620 provide defect count information for particular sensors associated with individual winding modules during a previous shift. FIG. 37 illustrates exemplary display screen 3700 that can be used to provide historical information concerning the last ten defects detected by the inspection system. Fields 3710 provide information concerning the last ten detected defects, including a defect profile for the defect and the time the defect was detected.

A surprising result of the flex winder operation is the ability of the winder to wind logs with worse web transfer characteristics than a conventional center or surface winder and the ability to continue winding without stopping the machine if the web breaks during roll build or at a region of the log in the machine cross direction. A conventional center or surface winder will normally break-out the web due to a very poor transfer or web break during winding, causing shut down of the machine so that the defective product can be stripped from the machine and the web rethreaded before restarting the machine.

Use of asynchronous motion control techniques and the registration and inspection techniques for detection of winding faults disclosed herein, culling of defective product and initiation of an early cut-off of the web can be achieved. For instance, in a particular implementation, a defective product can be culled from a particular winding module while the web is being transferred to the next available winding module for winding on the next available winding module. This leads to reduced waste and increased productivity. Defective web or web that was not wound into a log due to a web break can be carried down the web transport apparatus to the waste handling web transport apparatus.

The material particularly shown and described above is not meant to be limiting, but instead serves to show and teach various exemplary implementations of the present subject matter. As set forth in the attached claims, the scope of the present invention includes both combinations and sub-combinations of various features discussed herein, along with such variations and modifications as would occur to a person of skill in the art.

What is claimed:

1. An inspection method, suitable for use in connection with a winder producing a rolled product from a web, the winder comprising a web transport apparatus for conveying a web and at least one winding module onto which the web is rolled to form the robed product during a winding process, the winding module defining a cross direction generally perpendicular to the direction the web is conveyed by the web transport apparatus, the method comprising:

scanning with at least one sensor a region proximate the winding module;

detecting a defect with the at least one sensor;

associating a winding process parameter with the defect; and classifying the defect into at least one of a plurality of defect profiles based on the winding process parameter associated with the defect.

2. The inspection method of claim 1, wherein the winding process parameter comprises a percent roll build of the web.

3. The inspection method of claim 2, wherein the percent roll build is measured as web distance.

4. The inspection method of claim 2, wherein classifying the defect into at least one of a plurality of defect profiles comprises;

segmenting a roll build of the web onto a winding module into a plurality of inspection windows;

classifying the defect into one of the plurality of inspection windows based at least in part on the percent roll build associated with the defect.

5. The inspection method of claim 4, wherein the roll build is segmented into a roll transfer inspection window, a roll build inspection window, and a post roll build inspection window.

6. The inspection method of claim 5, wherein the roll transfer inspection window is defined to exclude a period of roll build following the time at which the winding process is initiated.

7. The inspection method of claim 4, wherein the method comprises adjusting the sensitivity of the at least one sensor so that the sensitivity of the sensor during one of the plurality of inspection windows is different than the sensitivity of the sensor during another one of the plurality of inspection windows.

8. The inspection method of claim 1, wherein the at least one sensor comprises a cross-direction winding sensor, the cross-direction winding sensor scanning across the cross-direction of the winding module at a location proximate the winding module.

9. The inspection method of claim 1, wherein the at least one sensor comprises a plurality of winding defect array sensors, the winding defect array sensors scanning a region across a width of the web transport apparatus at a location downstream of the winding module.

10. The inspection method of claim 9, wherein the winding process parameter comprises the winding defect array sensor to first detect the defect.

11. The inspection method of claim 10, wherein classifying the defect into at least one of a plurality of defect profiles comprises:

segmenting the plurality of winding defect array sensors into a plurality of inspection sensor segments; and classifying the defect into one of the plurality of inspection sensor segments based on the winding defect array sensor to first detect the defect.

12. The inspection method of claim 11, wherein the plurality of inspection sensor segments comprises an operator side sensor segment, a middle sensor segment, and a drive side sensor segment.

13. The inspection method of claim 1, wherein the at least one sensor comprises one of a photo-eye sensor, proximity switch, photo eye array, camera, or laser.

14. The inspection method of claim 1, wherein the method further comprises controlling the at least one winding module based at least in part on the defect.

15. The inspection method of claim 1, wherein the method further comprises:

initiating a cut-off for the winding module when a defect is detected;

culling the rolled product from the winding module; and transferring the web to a different winding module while the rolled product is being culled from the winding module.

16. A system for monitoring defects suitable for use in connection with a winder producing a rolled product from a web, the winder comprising a web transport apparatus for conveying a web and at least one winding module onto which the web is rolled to form the rolled product during a winding process, the winding module defining a cross direction generally perpendicular to the direction the web is conveyed by the web transport apparatus, the system comprising:

a plurality of sensors configured to scan a region proximate the winding module, each of the plurality of sensors configured to detect a defect during the winding process;

a controller coupled to the plurality of sensors, wherein the controller is configured to:

associate a winding process parameter with the defect; and classify the defect into at least one of a plurality of defect profiles based at least in part on the winding process parameter associated with the defect.

17. The system of claim 16, wherein the winding process parameter comprises at least one of a percent roll build of the web or the identity of the sensor to first detect the defect.

18. The system of claim 16, wherein the plurality of defect profiles are based at least in part on segmenting a roll build of the web into a roll transfer inspection window, a roll build inspection window, and a post roll build inspection window.

19. The system of claim 16, wherein the plurality of defect profiles are based at least in part on segmenting the plurality of sensors into an operator side sensor segment, a middle sensor segment, and a drive side sensor segment.

20. The system of claim 16, wherein the plurality of sensors comprises an upstream cross-direction winding sensor positioned to scan across the cross-direction of the winding module at a location proximate upstream of the winding module.

21. The system of claim 16, wherein the plurality of sensor comprises a downstream cross-direction winding sensor positioned to scan across the cross-direction of the winding module at a location proximate downstream of the winding module.

22. The system of claim 16, wherein the plurality of sensors comprises a plurality of winding defect array sensors positioned to scan across a width of the web transport apparatus at a location downstream of the winding module.

23. The system of claim 22, wherein the plurality of sensors further comprises a plurality of downstream module array sensors positioned to scan across a width of the web transport apparatus at a location downstream of the plurality of winding defect array sensors.

24. The system of claim 16, wherein the plurality of sensors comprise photo-eye sensors, proximity switches, photo eye arrays, cameras, or lasers.

25. The system of claim 16, wherein the system is coupled to a winder control system configured to control the winding module.

\* \* \* \* \*

UNITED STATES PATENT AND TRADEMARK OFFICE
CERTIFICATE OF CORRECTION

PATENT NO. : 8,714,472 B2
APPLICATION NO. : 12/750331
DATED : May 6, 2014
INVENTOR(S) : Schoenberg et al.

Page 1 of 1

It is certified that error appears in the above-identified patent and that said Letters Patent is hereby corrected as shown below:

In the Claims

Column 41, line 1, claim 1 after the words "form the", delete "robed" and insert --rolled--

Signed and Sealed this
Twelfth Day of August, 2014

Michelle K. Lee
*Deputy Director of the United States Patent and Trademark Office*